(12) United States Patent
Frydman et al.

(10) Patent No.: US 7,312,244 B2
(45) Date of Patent: Dec. 25, 2007

(54) POLYAMINE ANALOG-AMINO ACID CONJUGATES USEFUL AS ANTICANCER AGENTS

(75) Inventors: Benjamin Frydman, deceased, late of Madison, WI (US); by Linda Clifford, legal representative, Madison, WI (US); Laurence J. Marton, Palo Alto, CA (US); Aldonia L. Valasinas, Buenos Aires (AR); Venodhar K. Reddy, Madison, WI (US)

(73) Assignee: Cellgate, Inc., Redwood City, CA (US)

( * ) Notice: Subject to any disclaimer, the term of this patent is extended or adjusted under 35 U.S.C. 154(b) by 0 days.

(21) Appl. No.: 10/415,377

(22) PCT Filed: Nov. 8, 2001

(86) PCT No.: PCT/US01/43585

§ 371 (c)(1),
(2), (4) Date: Feb. 13, 2004

(87) PCT Pub. No.: WO02/38105

PCT Pub. Date: May 16, 2002

(65) Prior Publication Data

US 2004/0133013 A1    Jul. 8, 2004

Related U.S. Application Data

(63) Continuation-in-part of application No. 09/561,172, filed on Apr. 27, 2000, now Pat. No. 6,649,587.

(60) Provisional application No. 60/246,804, filed on Nov. 8, 2000, provisional application No. 60/131,809, filed on Apr. 30, 1999, provisional application No. 60/131,779, filed on Apr. 30, 1999, provisional application No. 60/131,842, filed on Apr. 30, 1999.

(51) Int. Cl.
*A61K 31/27* (2006.01)
*C07C 205/00* (2006.01)
*C07C 261/00* (2006.01)

(52) U.S. Cl. .................. 514/477; 514/478; 514/479; 514/642; 514/740; 560/23; 560/25

(58) Field of Classification Search ............ 514/477, 514/478, 479, 642, 740
See application file for complete search history.

(56) References Cited

U.S. PATENT DOCUMENTS

| | | | |
|---|---|---|---|
| 2,440,724 A | 5/1948 | Morey | |
| 3,008,993 A | 11/1961 | Lesslie et al. | |
| 3,397,223 A | 8/1968 | Payne | |
| 3,773,833 A | 11/1973 | Henrici et al. | |
| 4,035,174 A | 7/1977 | Grier et al. | |
| 4,092,432 A | 5/1978 | Bjorklund et al. | |
| 4,153,567 A | 5/1979 | Kluger et al. | |
| 4,273,706 A | 6/1981 | Chapman et al. | |
| 4,443,604 A | 4/1984 | Lee | |
| 4,491,651 A | 1/1985 | Naiman | |
| 4,537,601 A | 8/1985 | Naiman | |
| 4,551,550 A | 11/1985 | Bey | |
| 4,577,636 A | 3/1986 | Spears | |
| 4,590,288 A | 5/1986 | Klemann | |
| 4,642,344 A | 2/1987 | Hajek et al. | |
| 4,658,023 A | 4/1987 | Shudo | |
| 4,661,509 A | 4/1987 | Gordon et al. | |
| 4,698,446 A | 10/1987 | Lai et al. | |
| 4,767,611 A | 8/1988 | Gordon | |
| 4,784,736 A | 11/1988 | Lonsdale et al. | |
| 4,849,207 A | 7/1989 | Sakata et al. | |
| 4,868,219 A | 9/1989 | Thornfeldt | |
| 4,898,870 A | 2/1990 | Narutomi et al. | |
| 4,935,449 A | 6/1990 | Bey et al. | |
| 4,959,356 A | 9/1990 | Miura et al. | |
| 4,963,565 A | 10/1990 | Gangadharam | |
| 4,996,312 A | 2/1991 | Sakata et al. | |
| 5,007,437 A | 4/1991 | Sterzer | |
| 5,021,409 A | 6/1991 | Murrer et al. | |
| 5,021,571 A | 6/1991 | Mease et al. | |
| 5,080,998 A | 1/1992 | Irving et al. | |
| 5,091,576 A | 2/1992 | Bergeron | |
| 5,120,843 A | 6/1992 | McCall et al. | |
| 5,132,425 A | 7/1992 | Sotoya et al. | |
| 5,210,239 A | 5/1993 | Abe et al. | |

(Continued)

FOREIGN PATENT DOCUMENTS

DE    1 295 826 B    5/1969

(Continued)

OTHER PUBLICATIONS

Weeks et al. Novel Lysine-Spermine Conjugate Inhibits Polyamine Transport and Inhibits Cell Growth When Given with DFMO. Experimental Cell Research, 261, 2000, p. 293-302.*

(Continued)

*Primary Examiner*—Sikarl A. Witherspoon
(74) *Attorney, Agent, or Firm*—Morrison & Foerster LLP

(57) ABSTRACT

Conjugates in which polyamine analogs are conjugated to an amino acid are provided, as well as compositions comprising these conjugates. Methods of using these conjugates as anticancer treatments are also provided.

24 Claims, 11 Drawing Sheets

U.S. PATENT DOCUMENTS

| | | | |
|---|---|---|---|
| 5,217,964 A | 6/1993 | Edwards et al. | |
| 5,242,684 A | 9/1993 | Merianos | |
| 5,274,090 A | 12/1993 | Zhang et al. | |
| 5,283,367 A | 2/1994 | Babiarz et al. | |
| 5,284,647 A | 2/1994 | Niedballa et al. | |
| 5,344,435 A | 9/1994 | Turner et al. | |
| 5,354,782 A | 10/1994 | Edwards et al. | |
| 5,354,858 A | 10/1994 | Morgan et al. | |
| 5,374,658 A | 12/1994 | Lau | |
| 5,385,942 A | 1/1995 | Abe et al. | |
| 5,401,443 A | 3/1995 | Nagano et al. | |
| 5,413,719 A | 5/1995 | Sivakumar et al. | |
| 5,424,305 A | 6/1995 | Skalkos et al. | |
| 5,434,145 A | 7/1995 | Edwards et al. | |
| 5,498,522 A | 3/1996 | Porter | |
| 5,512,559 A | 4/1996 | Skalkos et al. | |
| 5,512,597 A | 4/1996 | Kyba et al. | |
| 5,516,807 A | 5/1996 | Hupe et al. | |
| 5,541,230 A | 7/1996 | Basu et al. | 514/642 |
| 5,563,262 A | 10/1996 | Morgan et al. | |
| 5,587,394 A | 12/1996 | Morgan et al. | |
| H1633 H | 2/1997 | Hiebert et al. | |
| 5,599,686 A | 2/1997 | DeFeo-Jones et al. | |
| 5,599,847 A | 2/1997 | Robins et al. | |
| 5,606,053 A | 2/1997 | Prashad et al. | |
| 5,607,574 A | 3/1997 | Hart | |
| 5,608,061 A | 3/1997 | Ciszewski et al. | |
| 5,608,086 A | 3/1997 | Hemmerle | |
| 5,612,478 A | 3/1997 | Xu et al. | |
| 5,627,215 A | 5/1997 | Frei et al. | |
| 5,633,230 A | 5/1997 | Twist et al. | 514/15 |
| 5,641,773 A | 6/1997 | Pardee et al. | |
| 5,646,188 A | 7/1997 | Gilad et al. | |
| 5,650,099 A | 7/1997 | Akhavan-Tafti et al. | |
| 5,654,287 A | 8/1997 | Prakash et al. | 514/49 |
| 5,654,484 A | 8/1997 | Prakash et al. | |
| 5,672,202 A | 9/1997 | Stirling et al. | |
| 5,674,900 A | 10/1997 | Ubillas et al. | |
| 5,677,349 A | 10/1997 | Gilad et al. | |
| 5,677,350 A | 10/1997 | Frydman | |
| 5,677,351 A | 10/1997 | Bergeron, Jr. | |
| 5,681,837 A | 10/1997 | Bergeron | |
| 5,693,632 A | 12/1997 | Morgan et al. | |
| 5,707,532 A | 1/1998 | Guerro et al. | |
| 5,719,193 A | 2/1998 | Bowlin et al. | |
| 5,744,453 A | 4/1998 | Mintz et al. | |
| 5,763,388 A | 6/1998 | Lightsey et al. | |
| 5,763,625 A | 6/1998 | Boothman et al. | |
| 5,776,458 A | 7/1998 | Angelucci et al. | |
| 5,780,514 A | 7/1998 | Gutteridge et al. | |
| 5,783,598 A | 7/1998 | Boyd et al. | |
| 5,824,700 A | 10/1998 | Frydman et al. | |
| 5,824,812 A | 10/1998 | Nantz et al. | |
| 5,843,865 A | 12/1998 | Del Corral et al. | |
| 5,843,959 A | 12/1998 | Bergeron, Jr. | |
| 5,849,259 A | 12/1998 | Hilger et al. | |
| 5,866,679 A | 2/1999 | DeFeo-Jones et al. | |
| 5,869,522 A | 2/1999 | Boyd et al. | |
| 5,877,165 A | 3/1999 | Miura et al. | |
| 5,880,161 A | 3/1999 | Basu et al. | |
| 5,883,270 A | 3/1999 | Frydman et al. | |
| 5,886,050 A | 3/1999 | Bergeron, Jr. | |
| 5,886,051 A | 3/1999 | Bergeron, Jr. et al. | |
| 5,886,173 A | 3/1999 | Hemmi et al. | |
| 5,889,061 A | 3/1999 | Frydman et al. | |
| 5,906,996 A | 5/1999 | Murphy | |
| 5,912,241 A | 6/1999 | Gottlieb et al. | |
| 5,932,201 A | 8/1999 | de Labbey et al. | |
| 5,958,397 A | 9/1999 | Smerbeck et al. | |
| 5,962,533 A | 10/1999 | Bergeron, Jr. | |
| 5,969,163 A | 10/1999 | Frydman et al. | |
| 5,977,187 A | 11/1999 | Frydman et al. | |
| 5,985,331 A | 11/1999 | Gottlieb et al. | |
| 5,998,362 A | 12/1999 | Feng et al. | |
| 6,001,573 A | 12/1999 | Roelant | |
| 6,025,351 A | 2/2000 | Morgan et al. | |
| 6,034,129 A | 3/2000 | Mandeville, III et al. | |
| 6,051,611 A | 4/2000 | Kyba et al. | |
| 6,066,628 A | 5/2000 | Stojiljkovic et al. | |
| 6,083,479 A | 7/2000 | Platzek et al. | |
| 6,100,430 A | 8/2000 | Yamamoto et al. | |
| 6,103,666 A | 8/2000 | Del Corral et al. | |
| 6,130,204 A | 10/2000 | DeFeo-Jones et al. | |
| 6,143,864 A | 11/2000 | DeFeo-Jones et al. | |
| 6,174,858 B1 | 1/2001 | Brady et al. | |
| 6,177,561 B1 | 1/2001 | Sinn et al. | |
| 6,184,232 B1 | 2/2001 | Bergeron, Jr. | |
| 6,207,660 B1 | 3/2001 | Sessler et al. | |
| 6,235,794 B1 | 5/2001 | Bergeron, Jr. | |
| 6,265,540 B1 | 7/2001 | Isaacs et al. | |
| 6,274,630 B1 | 8/2001 | Bergeron, Jr. | |
| 6,307,102 B1 | 10/2001 | Tokumoto et al. | |
| 6,319,956 B1 | 11/2001 | Iwata | |
| 6,342,534 B1 | 1/2002 | Bergeron, Jr. | |
| 6,384,097 B1 | 5/2002 | Tokumoto et al. | |
| 6,384,177 B1 | 5/2002 | Tokumoto et al. | |
| 6,392,098 B1 | 5/2002 | Frydman et al. | |
| 6,395,257 B1 | 5/2002 | Achilefu et al. | |
| 6,399,662 B1 | 6/2002 | Bergeron | |
| 6,444,707 B1 | 9/2002 | Lampe et al. | |
| 6,482,943 B1 | 11/2002 | Blokhin et al. | |
| 6,528,048 B1 | 3/2003 | Koike et al. | |
| 6,531,512 B1 | 3/2003 | Kramer et al. | |
| 6,605,645 B2 | 8/2003 | Iwata | |
| 6,641,655 B1 | 11/2003 | McElhinney et al. | |
| 6,646,149 B1 * | 11/2003 | Vermeulin et al. | 560/25 |
| 6,649,587 B1 | 11/2003 | Frydman et al. | |
| 6,664,270 B2 | 12/2003 | Bergeron, Jr. | |
| 6,673,890 B1 | 1/2004 | Boeckh et al. | |
| 6,706,922 B2 | 3/2004 | Wolff et al. | |
| 6,794,545 B1 | 9/2004 | Frydman et al. | |
| 6,809,176 B2 | 10/2004 | Blokhin et al. | |
| 2002/0004031 A1 | 1/2002 | Dinkelborg et al. | |
| 2002/0045780 A1 | 4/2002 | Bergeron, Jr. | |
| 2002/0061287 A1 | 5/2002 | Wolff et al. | |
| 2002/0061926 A1 | 5/2002 | Phillips | |
| 2002/0094990 A1 | 7/2002 | Bergeron | |
| 2002/0143068 A1 | 10/2002 | Bergeron, Jr. | |
| 2002/0155999 A1 | 10/2002 | Han | |
| 2003/0036538 A1 | 2/2003 | Rajagopalan et al. | |
| 2003/0045674 A1 | 3/2003 | Higley | |
| 2003/0055113 A1 | 3/2003 | Wang et al. | |
| 2003/0100615 A1 | 5/2003 | Bergeron, Jr. | |
| 2003/0130356 A1 | 7/2003 | Frydman et al. | |
| 2003/0130534 A1 | 7/2003 | Golden | |
| 2003/0143713 A1 | 7/2003 | Aghajari et al. | |
| 2003/0158262 A1 | 8/2003 | Ramesh et al. | |
| 2003/0185778 A1 | 10/2003 | Fahl et al. | |
| 2003/0195377 A1 | 10/2003 | Frydman et al. | |
| 2003/0232799 A1 | 12/2003 | Wang et al. | |
| 2004/0006049 A1 | 1/2004 | Frydman et al. | |
| 2004/0006055 A1 | 1/2004 | Winchell | |
| 2004/0019043 A1 | 1/2004 | Coucouvanis et al. | |
| 2004/0019087 A1 | 1/2004 | Ternansky et al. | |
| 2004/0039057 A1 | 2/2004 | Perlmutter et al. | |
| 2004/0047844 A1 | 3/2004 | Shepard | |
| 2004/0152687 A1 | 8/2004 | Frydman et al. | |
| 2004/0192665 A1 | 9/2004 | Frydman et al. | |
| 2004/0235962 A1 | 11/2004 | Frydman et al. | |

FOREIGN PATENT DOCUMENTS

| | | |
|---|---|---|
| EP | 0 723 772 A1 | 7/1996 |
| EP | 0 723 772 B1 | 7/1996 |

| | | |
|---|---|---|
| EP | 0 255 679 A2 | 2/1998 |
| EP | 0 255 679 A3 | 2/1998 |
| EP | 0 255 679 B1 | 2/1998 |
| JP | 05-032902 A | 2/1993 |
| JP | 07-277964 A | 10/1995 |
| JP | 09-235280 A | 9/1997 |
| WO | 91/00853 A1 | 1/1991 |
| WO | WO-94/07480 A1 | 4/1994 |
| WO | WO-94/07894 A1 | 4/1994 |
| WO | WO-94/08578 A2 | 4/1994 |
| WO | WO-95/18091 A1 | 7/1995 |
| WO | WO-96/22962 A1 | 8/1996 |
| WO | WO-96/33988 A1 | 10/1996 |
| WO | WO-96/40096 A1 | 12/1996 |
| WO | WO-97/02027 A1 | 1/1997 |
| WO | WO-97/02030 A1 | 1/1997 |
| WO | WO-97/08162 A1 | 3/1997 |
| WO | WO-97/29199 A2 | 8/1997 |
| WO | WO-97/29199 A3 | 8/1997 |
| WO | WO-97/30022 A1 | 8/1997 |
| WO | WO-97/31611 A2 | 9/1997 |
| WO | WO-97/31611 A3 | 9/1997 |
| WO | WO-97/31936 A2 | 9/1997 |
| WO | WO-97/31936 A3 | 9/1997 |
| WO | WO97/33560 | 9/1997 |
| WO | WO-98/10651 A1 | 3/1998 |
| WO | WO-98/14190 A1 | 4/1998 |
| WO | WO-98/17624 A1 | 4/1998 |
| WO | WO-98/25884 A1 | 6/1998 |
| WO | WO-98/32729 A1 | 7/1998 |
| WO | WO-98/33503 A1 | 8/1998 |
| WO | WO-98/37057 A1 | 8/1998 |
| WO | WO-98/52966 A1 | 11/1998 |
| WO | WO-98/56425 A1 | 12/1998 |
| WO | WO-99/13920 A2 | 3/1999 |
| WO | WO-99/13920 A3 | 3/1999 |
| WO | WO-99/16474 A1 | 4/1999 |
| WO | WO-99/16757 A1 | 4/1999 |
| WO | WO-99/21542 A2 | 5/1999 |
| WO | WO-99/21542 A3 | 5/1999 |
| WO | 99/31049 A1 | 6/1999 |
| WO | WO-99/54283 A1 | 10/1999 |
| WO | WO-99/62512 A1 | 12/1999 |
| WO | WO-00/01419 A1 | 1/2000 |
| WO | WO-00/05235 A1 | 2/2000 |
| WO | WO-00/17205 A2 | 3/2000 |
| WO | WO-00/17205 A3 | 3/2000 |
| WO | WO-00/18439 A2 | 4/2000 |
| WO | WO-00/18439 A3 | 4/2000 |
| WO | WO-00/66175 A2 | 11/2000 |
| WO | WO-00/66175 A3 | 11/2000 |
| WO | WO-00/66528 A2 | 11/2000 |
| WO | WO-00/66528 A3 | 11/2000 |
| WO | WO-00/66587 A2 | 11/2000 |
| WO | WO-00/66587 A3 | 11/2000 |
| WO | WO-02/10142 A1 | 2/2002 |
| WO | 02/38105 A2 | 5/2002 |
| WO | 02/38105 A3 | 5/2002 |
| WO | WO-02/062341 A1 | 8/2002 |
| WO | WO-02/091989 A2 | 11/2002 |
| WO | WO-02/091989 A3 | 11/2002 |
| WO | WO-03/004091 A2 | 1/2003 |
| WO | WO-03/004091 A3 | 1/2003 |
| WO | WO-03/004466 A2 | 1/2003 |
| WO | WO-03/004466 A3 | 1/2003 |
| WO | WO-03/033455 A1 | 4/2003 |
| WO | WO-03/050072 A1 | 6/2003 |
| WO | WO-03/051348 A2 | 6/2003 |
| WO | WO-03/051348 A3 | 6/2003 |
| WO | WO-2004/002991 A1 | 1/2004 |
| WO | WO-2004/041828 A1 | 5/2004 |

OTHER PUBLICATIONS

Marsh, B. H., "Changes in Soluble Amino Acid and Polyamine Composition Associated With Increasing Plant Density and the Onset of Sporulation in Azolla", Symbiosis, 1998, vol. 24, No. 3, pp. 315-326, Abstract.

Akgun, N. et al. (1996). "Phototoxicity, Darktoxicity and Uptake-Kinetics of Natural Hydrophilic and Hydrophobic Phorphyrins in Endothelial Cells," *Proc. SPIE-Int. Soc. Opt. Eng.* 2625:488-498.

Alfonso, I. et al. (1996). "Sequential Biocatalytic Resolution of (±)-*trans*-cyclohexane-1,2-diamine. Chemoenzymatic Synthesis of an Optically Active Polyamine," *Chem. Commun.* 21:2471-2472.

Allolio, B. et al. (1989). "Treatment of Metastasic Adrenal Carcinoma with Suramin," *Dtsch. Med. Woschenschr* 114(10):381-384. (In German with English abstract).

Ando, A. et al. (Aug. 1990). "Synthesis of Fluorine Analogues of Protoporphyrin Potentially Useful for Diagnosis and Therapy of Tumors," *Chemical and Pharmaceutical Bulletin* 38(8):2175-2178.

Ashraf, W. et al. (1994). "Comparative Effects of Intraduodenal Psyllium and Senna on Canine Small Bowel Motility," *Aliment. Pharmacol. Ther.* 8:329-336.

Ashton, W.T. et al. (1988). "Synthesis and Antiherpetic Activity of (±)-9-[[(Z)-2-(Hydroxymethyl)cyclopropyl]methyl]guanine and Related Compounds," *J. Med. Chem.* 31(12):2304-2315.

Bachmann, S. et al. (2001). "Cis-Selective Asymmetric Cyclopropanation of Olefins Catalyzed by Five-Coordinate [RuCl(PNNP)]+ Complexes," *Organometallics* 20(10):2102-2108.

Bachrach, U. et al. (1971). "Antivirus Action of Acrolein, Glutaraldehyde and Oxidized Spermine" *J. Gen. Virol.* 13:415-422.

Bachrach, U. et al. (1971). "Inactivation of Myxoviruses by Oxidized Polyamines" *J. Gen. Virol.* 11(1):1-9.

Bachrach, U. et al. (Feb. 1972). "Effect of Oxidized Spermine and Other Aldehydes on the Infectivity of Vaccinia Virus" *Appl. Microbiol.* 23(2):232-235.

Baez, S. et al. (1997). "Glutathione Transferases Catalyse the Detoxication of Oxidized Metabolites (o-quinones) of Catecholamines and May Serve as an Antioxidant System Preventing Degenerative Cellular Processes," *Biochem. J.* 324:25-28.

Bailey, S.M. et al. (1997). "Involvement of DT-Diaphorase (EC 1.6.99.2) in the DNA Cross-Linking and Sequence Selectivity of the Bioreductive Anti-Tumour Agent EO9," *Br. J. Cancer* 76(12):1596-1603.

Barluenga, J. et al. (2000). "Diastereoselective Intermolecular Cyclopropanation of Simple Alkenes by Fischer Alkenyl and Heteroaryl Carbene Complexes of Chromium: Scope and Limitations," *J. Am. Chem. Soc.* 122(34):8145-8154.

Basu, H.S. et al. (1990). "Effects of Variation in the Structure of Spermine on the Association with DNA and the Induction of DNA Conformational Changes" *Biochem. J.* 269:329-334.

Begleiter, A. et al. (1997). "Induction of DT-Diaphorase in Cancer Chemoprevention and Chemotherapy," *Oncol. Res.* 9:371-382.

Behe, M. et al. (Mar. 1981). "Effects of Methylation on a Synthetic Polynucleotide: The B-Z Transition in Poly(dG-m$^5$dC)·poly(dG-m$^5$dC)," *Proc. Natl. Acad. Sci. USA* 78(3):1619-1623.

Berchtold, C.M. et al. (1998). "Inhibition of Cell Growth in CaCO2 Cells by the Polyamine Analogue $N^1$, $N^{12}$-bis(ethyl)Spermine is Preceded by a Reduction in MYC Oncoprotein Levels," *J. Cell. Physiol.* 174:380-386.

Bergeron, R.J. et al. (1994). "Antiproliferative Properties of Polyamine Analogues: A Structure-Activity Study," *J. Med. Chem.* 37(21):3464-3476.

Bernacki, R.J. et al. (May 1, 1992). "Antitumor Activity of *N*, $N^1$-Bis(ethyl)spermine Homologues Against Human MALME-3 Melanoma Xenografts," *Cancer Res.* 52:2424-2430.

Bloomfield, V.A. et al. (1981). "Interactions of Polyamines with Polynucleotides," Chapter 10 *In Polyamines in Biology and Medicine*, Morris, D.R. et al. eds., Marcel Dekker, Inc.: New York, N.Y., pp. 183-206.

Boveris, A. et al. (1978). "Superoxide Anion Production and Trypanocidal Action of Naphthoquinones on *Trypanosoma cruzi*," *Comp. Biochem. Physiol.* 61C:327-329.

Bressoud, D., et al. (1992). "Dark Induction of Haem Oxygenase Messenger RNA by Haematoporphyrin Derivative and Zinc Phthalocyanine; Agents for Photodynamic Therapy," *J. Photochem. Photobiol. B: Biol.* 14:311-318.

Broder, S. et al. (Sep. 21, 1985). "Effects of Suramin on HTLV-III/LAV Infection Presenting as Kaposi's Sarcoma or AIDS-Related Complex: Clinical Pharmacology and Suppression of Virus Replication In Vivo," *The Lancet* 2:627-630.

Brunner, H. et al. (1994). "Platinum(II) Complexes With Porphyrin Ligands—Additive Cytotoxic and Photodynamic Effect," *Angew. Chem. Int. Ed. Engl.* 33(21):2214-2215.

Bullock, F.J. et al. (Jan. 1970). "Antiprotozoal Quinones. II. Synthesis of 4-Amino-1,2-naphthoquinones and Related Compounds as Potential Antimalariats," *J. Med. Chem.* 13:97-103.

Byers, T.L. et al (1990). "Regulation of Polyamine Transport in Chinese Hamster Ovary Cells," *Journal of Cellular Physiology* 143(3):460-467.

Casero, R.A. Jr. et al. (1995). "Growth and Biochemical Effects of Unsymmetrically Substituted Polyamine Analogues in Human Lung Tumor Cells," *Cancer Chemother. Pharmacol.* 36:69-74.

Casero, R.A. Jr. et al. (Jan. 4, 2001). "Terminally Alkylated Polyamine Analogues as Chemotherapeutic Agents," *Journal of Medicinal Chemistry* 44(1):1-26.

Chang, B.K. et al. (1992). "Antitumor Effects of N-Alkylated Polyamine Analogues in Human Pancreatic Adenocarcinoma Models," *Cancer Chemother. Pharmacol.* 30(3):179-182.

Chang, B.K. et al. (1992). "Regulatory and Antiproliferative Effects of N-Alkylated Polyamine Analogues in Human and Hamster Pancreatic Adenocarcinoma Cell Lines," *Cancer Chemother. Pharmacol.* 30(3):183-188.

Chang, B.K. et al. (Oct. 1993). "Effects of Diethyl Spermine Analogues in Human Bladder Cancer Cell Lines in Culture," *J. Urol.* 150:1293-1297.

Christensson, A. et al. (1990). "Enzymatic Activity of Prostate-Specific Antigen and its Reactions with Extracellular Serine Proteinase Inhibitors," *Eur. J. Biochem.* 194:755-763.

Chung, J-H. et al. (1996). "Acceleration of the Alcohol Oxidation Rate in Rats with Aloin, a Quinone Derivative of *Aloe*," *Biochem. Pharmacol.* 52:1461-1468.

Clarys, P. et al. (1998). "Efficacy of Topical Treatment of Pigmentation Skin Disorders with Plant Hydroquinone Glucosides as Assessed by Quantitative Color Analysis," *J. Dermatol.* 25:412-414.

Cortelli, P. et al. (1997) "Clinical and Brain Bioenergetics Improvement with Idebenone in a Patient with Leber's Hereditary Optic Neuropathy: A Clinical and $^{31}$P-MRS Study," *J. Neurol. Sci.* 148:25-31.

Cote, P.N. et al. (1973). "Glucopyranosides Derived from 2-hydroxy-1,4-naphthoquinones," *Carbohyd. Res.* 26:247-251.

Creaven, P.J. et al. (1997). "Unusual Central Nervous System Toxicity in a Phase I Study of $N^1 N^{11}$ Diethylnorspermine in Patients with Advanced Malignancy," *Invest. New Drugs* 15:227-234.

Davidson, N.E. et al. (May 1, 1993). "Growth Inhibition of Hormone-Responsive and -Resistant Human Breast Cancer Cells in Culture by $N^1$, $N^{12}$ -Bis(Ethyl)Spermine," *Cancer Research* 53(9):2071-2075.

de Groot, F.M.H. et al. (1999). "Synthesis and Biological Evaluation of Novel Prodrugs of Anthracyclines for Selective Activation by the Tumor-Associated Protease Plasmin," *J. Med. Chem.* 42(25):5277-5283.

DeFeo-Jones, D. et al. (Nov. 2000). "A Peptide-Doxorubicin 'Prodrug' Activated by Prostate-Specific Antigen Selectively Kills Prostate Tumor Cells Positive for Prostate-Specific Antigen *In Vivo*," Nat. Med. 6(11):1248-1252.

Dekant, W. (1993). "Bioactivation of Nephrotoxins and Renal Carcinogens by Glutathione S-Conjugate Formation," *Toxicol. Lett.* 67:151-160.

Denmeade S.R. et al. (Mar. 2000). "Enzymatic Activation of a Thapsigargin Prodrug by Prostate Specific Antigen (PSA) as Treatment for Metastatic Prostate Cancer," *Proceedings of the American Association for Cancer Research 91st Annual Meeting* (Apr. 1-5, 2000, San Francisco, CA) 41:46 (Abstract #292).

Denmeade S.R. et al. (May 1998). "Enzymatic Activation of Prodrugs by Prostate-Specific Antigen: Targeted Therapy for Metastatic Prostate Cancer," *Cancer Journal From Scientific American* 4(Suppl.1):S15-S21.

Denmeade, S.R. et al. (Jun. 15, 1998). "Enzymatic Activation of a Doxorubicin-Peptide Prodrug by Prostate-Specific Antigen," *Cancer Res.* 58:2537-2540.

Denmeade, S.R. et al. (Nov. 1, 1997). "Specific and Efficient Peptide Substrates for Assaying the Proteolytic Activity of Prostate-specific Antigen," *Cancer Res.* 57:4924-4930.

Dolan, M.E. et al. (1998). "Effects of 1,2-naphthoquinones on Human Tumor Cell Growth and Lack of Cross-Resistance with Other Anticancer Agents," *Anti-Cancer Drugs* 9:437-448.

Doyle, M.P. et al. (1993). "Tetrakis[(4S)-4-phenyloxazolidin-2-one]dirhodium(II) and Its Catalytic Applications for Metal Carbene Transformations," *Helv. Chim. Acta.* 76:2227-2235.

Driscoll, J.S. et al. (Apr. 1974), "Structure Antitumor Activity Relationships Among Quinone Derivatives," *Cancer Chemotherapy Reports* Part 2, 4(2):1-362.

Dubowchik, G.M. et al. (1998). "Cathepsin B-Sensitive Dipeptide Prodrugs. 1. A Model Study of Structural Requirements for Efficient Release of Doxorubicin," *Bioorg. Med. Chem. Lett.* 8:3341-3346.

Dunn, W.J. III et al. (1980). "Structure-Activity Analyzed by Pattern Recognition: The Asymmetric Case," *J. Med. Chem.* 23(6):595-599.

Dunzendorfer, U. (1985). "Polyamines, Polyamine Antimetabolites and Urogenital Tumors. State of Research and Clinical Results," *Urol. Int.* 40:241-250. (In German with English abstract.).

Eyer, P. (Oct. 1994). "Reactions of Oxidatively Activated Arylamines with Thiols: Reaction Mechanisms and Biologic Implications. An Overview," *Environ. Health Persp.* 102(Suppl. 6):123-132.

Fernández, C.O. et al. (1994). "Interactions Between Polyamine Analogs with Antiproliferative Effects and tRNA: A $^{15}$N NMR analysis," *Cell Mol. Biol.* 40(7):933-944.

Feuerstein, B.G. et al. (1991). "Implications and Concepts of Polyamine-Nucleic Acid Interactions," *Journal of Cellular Biochemistry* 46(1):37-47.

Fiedler, W.J. et al. (1993). "Synthesis of Selectively N-Functionalized Polyamine Derivatives," *Helv. Chim. Acta* 76:1511-1519. (In German with English abstract.).

Fischer, H.A. (1975. "Synthesis of $^3$H-Spermine," *J. Labelled Compd.* 11(1):141-143. (In German with Chemical Abstracts CAPlus record attached.).

Fowler, L.M. et al. (1991). "Nephrotoxicity of 4-Aminophenol Glutathione Conjugate," *Hum. Exp. Toxicol.* 10:451-459.

Freitas, I. et al. (1987). "Dark Effects of Hematoporphyrin Derivative on Lactate Dehydrogenase Activity and Distribution in HeLa Cells: Cytochemical Evaluation," *Photochemistry and Photobiology* 46(5):699-706.

Freitas, I. et al. (1988). "Dark Effects of Porphyrins on the Activity and Subcellular Distribution of Dehydrogenases in Yoshida Hepatoma Cells: Cytochemical Evaluations," *Medicine Biologie Environnement* 16:97-109.

Frydman, B. et al. (1999). "Polyamine-Based Chemotherapy of Cancer," *Exp. Opin. Ther. Patents* 9(8):1055-1068.

Frydman, B. et al. (Feb. 15, 1997). "Induction of DNA Topoisomerase II-Mediated DNA Cleavage by Beta-Lapachone and Related Naphthoquinones," *Cancer Res.* 57:620-627.

Frydman, L et al. (Oct. 1992). "Interactions Between Natural Polyamines and tRNA: An $^{15}$N NMR Analysis," *Proc. Natl. Acad. Sci. USA* 89:9186-9190.

Gantchev, T.G. et al. (1997). "Inhibition of the Topoisomerase II-DNA Cleavable Complex by the *ortho*-Quinone Derivative of the Antitumor Drug Etoposide (VP-16)," *Biochem. Biophys. Res. Comm.* 237(1):24-27.

Gosule, L.C. et al. (1978). "DNA Condensation with Polyamines I. Spectroscopic Studies," *J. Mol. Biol.* 121(3):311-326.

Goto, M. et al. (Feb. 1969). "Stereochemical Studies of Metal Chelates. III. Preparation and Stereochemistry of Cobalt (III) Complexes with C-Substituted Triethylenetetramines at the Central Ethylenediamine Bridge," *Inorg. Chem.* 8(2):358-366.

Ha, H.C. et al. (Jul. 1, 1998). "Unsymmetrically Substituted Polyamine Analogue Induces Caspase-Independent Programmed Cell Death in Bcl-2-Overexpressing Cells," *Cancer Research* 58:2711-2714.

Hafner, E.W. et al. (Dec. 25, 1979). "Mutants of *Escherichia coli* that do not Contain 1,4-Diaminobutane (Putrescine) or Spermidine," *J. Biol. Chem.* 254(24):12419-12426.

Herr, H.W. et al. (Mar. 15, 1984). "Potentiation of Methylglyoxal-Bis-Guanylhydrazone by Alpha-Difluoromethylornithine in Rat Prostate Cancer," *Cancer* 53(6):1294-1298.

Hinson, J.A. et al. (1995). "Phase II Enzymes and Bioactivation," *Can. J. Physiol. Pharmacol.* 73:1407-1413.

Hondo, H. (1988). "Anti-Tumor Effect of Hyperthermia Plus Hematoporphynn Derivative on Malignant Brain Tumor," *Brain and Nerve* 40(5):477-484. (BIOSIS English language abstract only).

Horn, Y. et al. (1987). "Phase I-II Clinical Trial with Alpha-difluoromethylornithine—an Inhibitor of Polyamine Biosynthesis," *Eur. J. Cancer Clin. Oncol.* 23(8):1103-1107.

Horoszewicz, J.S. et al. (Apr. 1983). "LNCaP Model of Human Prostatic Carcinoma," *Cancer Res.* 43:1809-1818.

Igarashi, K. et al. (Oct. 30, 1990). "Spermine-Like Functions of $N^1$, $N^{12}$-Bis(Ethyl)Spermine: Stimulation of Protein Synthesis and Cell Growth and Inhibition of Gastric Ulceration," *Biochem. Biophys. Res. Commun.* 172(2):715-720.

Inouye, H. et al. (Feb. 1975). "Quinones and Related Compounds in Higher Plants. II. On the Naphthoquinones and Related Compounds from *Catalpa* Wood," *Chem. Pharm. Bull.* 23(2):384-391.

Iwata, M. et al. (1989). "Efficient Synthetic Method for Differentially Protected Naturally Occurring Acyclic Polyamines," *Bull. Chem. Soc. Japan* 62(4):1102-1106.

Jain, S. et al. (1989). "Base Only Binding of Spermine in the Deep Groove of the A-DNA Octamer d(GTGTACAC)," *Biochemistry* 28(6):2360-2364.

James, D. A. et al. (1994). "Potency and Selective Toxicity of Tetra(Hydroxyphenyl)- and Tetrakis(dihydroxyphenyl)porphyrins in Human Melanoma Cells, With and Without Exposure to Red Light," *Photochemistry and Photobiology* 59(4):441-447.

Jänne, J. et al. (1978). "Polyamines in Rapid Growth and Cancer," *Biochimica et Biophysica Acta.* 473:241-293.

Jeffers, L. et al. (1997). "Effects of the Polyamine Analogues BE-4-4-4-4, BE-3-7-3, and BE-3-3-3 on the Proliferation of Three Prostate Cancer Cell Lines," *Cancer Chemother Pharmacol* 40(2):172-179.

Jeong, J.K. et al. (Sep. 1996). "Quinone Thioether-Mediated DNA Damage, Growth Arrest, and *gadd153* Expression in Renal Proximal Tubular Epithelial Cells," *Mol. Pharmacol.* 50(3):592-598.

Kanter, P.M. et al. (1994). "Preclinical Toxicologic Evaluation of DENSPM ($N^1,N^{11}$—diethylnorspermine) in Rats and Dogs," *Anticancer Drugs* 5:448-456.

Khanum, F. et al. (1989). "Effects of Hematoporphyrin Derivative on the Cellular Energy Metabolism in the Absence and Presence of Light," *Photochem. and Photobiol.* 50(5):647-651.

Kobiro, K. et al. (1992). "Synthesis and Molecular Structures of Nickel (II) Alkyl-Substituted/Cyclam Complexes," *Inorg. Chem.* 31(4):676-685.

Koningsberger, J. C. et al. (Apr. 1992). "Toxic Dark Effects of Protoporphyrin (PP)," *Digestive Disease Week and The 93rd Annual Meeting of the American Gastroenterological Association*, San Francisco, California, Supplement to Gastroenterology 102(4): A835. (Abstract only).

Koningsberger, J. C. et al. (1995). "Exogenous Protoporphyrin Inhibits Hep G2 Cell Proliferation, Increases the Intracellular Hydrogen Peroxide Concentration and Causes Ultrastructural Alterations," *J. Hepatology* 22:57-65.

Kramer, D. et al. (Feb. 3, 1995). "Stable Amplification of the S-Adenosylmethionine Decarboxylase Gene in Chinese Hamster Ovary Cells," *J. Biol. Chem.* 270(5):2124-2132.

Kramer, D.L. et al. (1993). "Regulation of Polyamine Transport by Polyamines and Polyamine Analogs" *Journal of Cellular Physiology* 155(2):399-407.

Kramer, D.L. et al. (Dec. 15, 1997). "Effects of Novel Spermine Analogues on Cell Cycle Progression and Apoptosis in MALME-3M Human Melanoma Cells," *Cancer Res.* 57:5521-5527.

Li, C.J. et al. (Sep. 1, 1995). "Induction of Apoptosis by β-Lapachone in Human Prostate Cancer Cells," *Cancer Res.* 55:3712-3715.

Lilja, H. (Nov. 1985) "A Kallikrein-like Serine Prostease in Prostatic Fluid Cleaves the Predominant Sermial Vesicle Protein," *J. Clin. Invest.* 76(5):1899-1903.

Løvaas, E. (1997). "Antioxidative and Metal-Chelating Effects of Polyamines," *Advances in Pharmacology* 38:119-149.

Mahadik, S.P. et al. (1996). "Oxidative Injury and Potential Use of Antioxidants in Schizophrenia," *Prostaglandins Leukot. Essent. Fatty Acids* 55(1&2):45-54.

Mamont, P.S. et al. (Mar. 15, 1978). "Anti-Proliferative Properties of DL-α-Difluoromethyl Ornithine in Cultured Cells. A Consequence of the Irreversible Inhibition of Ornithine Decarboxylase," *Biochem. Biophys. Res. Commun.* 81(1):58-66.

Marton, L.J. et al. (1995). "Polyamines as Targets for Therapeutic Intervention," *Annu. Rev. Pharm. Toxicol.* 35:55-91.

Matsumoto, T. et al. (1969). "91. α-Caryopterone, A New Pyranojuglone from *Caryopteris clandonensis*," *Helv. Chim. Acta* 52(3):808-812 (In German with Chemical Abstracts English record attached).

Mazzoni, A. et al. (1986). "Comparative Distribution of Free Doxorubicin and Poly-L-Aspartic Acid Linked Doxorubicin in MS-2 Sarcoma Bearing Mice," *Cancer Drug Deliv.* 3(3):163-172.

McCloskey, D.E. et al. (Jan. 2000). "Effects of the Polyamine Analogues $N^1$-Ethyl-$N^{11}$-((cyclopropyl)methyl)-4,8-diazaundecane and $N^1$-Ethyl-$N^{11}$-((cycloheptyl)methyl)-4,8-diazaundecane in Human Prostate Cancer Cells," *Clinical Cancer Research* 6:17-23.

Mertens, J.J.W.M. et al. (1991). "Inhibition of γ-Glutamyl Transpeptidase Potentiates the Nephrotoxicity of Glutathione-Conjugated Chlorohydroquinones," *Toxicol. Appl. Pharmacol.* 110:45-60.

Mi, Z. et al. (1998). "Human Prostatic Carcinoma Cell Lines Display Altered Regulation of Polyamine Transport in Response to Polyamine Analogs and Inhibitors," *The Prostate* 34:51-60.

Monks, T.J. (1995). "Modulation of Quinol/Quinone-Thioether Toxicity by Intramolecular Detoxication," *Drug Metab. Rev.* 27(1 &2):93-106.

Monks, T.J. et al. (1994). "Oxidation and Acetylation as Determinants of 2-Bromocystein-S-ylhydroquinone-Mediated Nephrotoxicity," *Chem. Res. Toxicol.* 7(4):495-502.

Mordente, A. et al. (1998). "Antioxidant Properties of 2,3-Dimethoxy-5-Methyl-6-(10-Hydroxydecyl)-1,4-Benzoquinone (Idebenone)," *Chem. Res. Toxicol.* 11(1):54-63.

Morgan, D.M.L. et al. (1986). "The Effect of Purified Aminoaldehydes Produced by Polyamine Oxidation on the Development *in vitro* of *Plasmodium falciparum* in Normal and Glucose-6-Phosphate-Dehydrogenase-Deficient Erythrocytes," *Biochem. J.* 236(1):97-101.

Morgan, D.M.L. (1998). "Polyamines. An Introduction," *Methods. Mol. Biol.* 79:3-30.

Morgan, D.M.L. et al. (1983) "Polyamine Oxidation and the Killing of Intracellular Parasites." *Adv. Polyamine Res.* 4:169-174.

Mukhopadhyay, R. et al. (1995). "Effects of Bis(benzyl)Polyamine Analogs on *Leishmania donovani* Promastigotes," *Exp. Parasitol.* 81:39-46.

Müller-Lissner, S.A. (1993). "Adverse Effects of Laxatives: Fact and Fiction," *Pharmacol.* 47(Suppl. 1):138-145.

Nagarajan, S. et al. (1987). "Chemistry Of Naturally Occurring Polyamines. 11. Unsaturated Spermidine And Spermine Derivatives" *J. Org. Chem.* 52(22):5044-5046.

Nanji, A.A. et al. (1996). "Association Between Endothelial Cell Proliferation and Pathologic Changes in Experimental Alcoholic Liver Disease," *Toxicol. Appl. Pharmacol.* 140:101-107.

Neder, K. et al. (1998). "Reaction of β-Lapachone and Related Naphthoquinones with 2-Mercaptoethanol: A Biomimetic Model of Topoisomerase II Poisoning by Quinones," *Cell and Mol. Biol.* 44(3):465-474.

Nelson, W.L. et al. (1984). "The 3,4-Catechol Derivative of Propranolol, a Minor Dihydroxylated Metabolite," *J. Med. Chem.* 27(7):857-861.

Nguyen, S.T. et al. (1999). "Diastereo—And Enantioselective Cyclopropanation of Alkenes Catalyzed by Ruthenium-Schiff-Base Complexes," *Book of Abstracts, 218th ACS National Meeting*, New Orleans, LA, Aug. 22-26, 1999, Abstract No. INOR-104, two pages.

Nishimura, K. et al. (1971). "Phagocidal Effects of Acrolein," *Biochim. Biophys. Acta* 247:153-156.

Novarina, A. et al. (Jul. 1988). "Quantative Histochemistry of Lactate Dehydrogenase in Tumor Cells. Dark Effects of Porphyrin Drugs," *J. Histochemistry and Cytochemistry* 36(7a):941 (Abstract 404).

O'Brien, P.J. (1991). "Molecular Mechanisms of Quinone Cytotoxicity," *Chem. Biol. Interactions* 80:1-41.

O'Sullivan, M.C. et al. (1997). "Polyamine Derivatives as Inhibitors of Trypanothione Reductase and Assessment of Their Trypanocidal Activities," *Bioorg. Med. Chem.* 5(12):2145-2155.

Payne, G.B. (Nov. 1967). "Cyclopropanes from Reactions of Ethyl(Dimethylsulfuranylidene)acetate with $\alpha,\beta$-Unsaturated Compounds," *Journal of Organic Chemistry* 32(11):3351-3355.

Pegg, A.E. et al. (1982). "Polyamine Metabolism and Function," *Am. J. Cell. Physiol.* 243:C212-C221.

Pershin, G.N. et al. (1975). "Bonaphthone-A New Antiviral Chemotherapeutic Agent," *Russian Pharmacology and Toxicology* 38(1):21-27.

Planchon, S.M. et al. (1999). "Bcl-2 Protects Against $\beta$-Lapachone-Mediated Caspase 3 Activation and Apoptosis in Human Myeloid Leukemia (HL-60) Cells," *Oncol. Rep.* 6:485-492.

Planchon, S.M. et al. (Sep. 1, 1995). $\beta$-Lapachone-Mediated Apoptosis in Human Promyelocytic Leukemia (HL-60) and Human Prostate Cancer Cells: A p53-Independent Response, *Cancer Res.* 55:3706-3711.

Pohjanpelto, P. et al. (Oct. 8, 1981). "Polyamine Starvation Causes Disappearance of Actin Filaments and Microtubules in Polyamine-Auxotrophic CHO Cells," *Nature* 293:475-477.

Porter, C.W. et al. (1988). "Regulation of Polyamine Biosynthetic Activity by Spermidine and Spermine Analogs—A Novel Antiproliferative Strategy," *Adv. Exp. Med. Biol.* 250:677-690.

Porter, C.W. et al. (1988). "Enzyme Regulation as an Approach to Interference with Polyamine Biosynthesis-An Alternative to Enzyme Inhibition," *Advances in Enzyme Regulation* 27:57-79.

Porter, C.W. et al. (Jul. 15, 1991). "Correlations Between Polyamine Analogue-Induced Increases in Spermidine/Spermine $N^1$-Acetyltransferase Activity, Polyamine Pool Depletion, and Growth Inhibition in Human Melanoma Cell Lines," *Cancer Res.* 51:3715-3720.

Porter, C.W. et al. (Jun. 1, 1987). "Relative Abilities of Bis(Ethyl) Derivatives of Putrescine, Spermidine, and Spermine to Regulate Polyamine Biosynthesis and Inhibit L1210 Leukemia Cell Growth," *Cancer Res.* 47:2821-2825.

Puckett-Vaughn, D.L. et al. (1993). "Enzymatic Formation and Electrochemical Characterization of Multiply Substituted Glutathione Conjugates of Hydroquinone," *Life Sci.* 52(14):1239-1247.

Rainwater, L.M. et al. (Aug. 1990). "Prostate-Specific Antigen Testing in Untreated and Treated Prostatic Adenocarcinoma," *Mayo Clinic Proc.* 65:1118-1126.

Rao, D.N.R. et al. (1997). "A Comparative Study of the Redox-Cycling of a Quinone (Rifamycin S) and a Quinonimine (Rifabutin) Antibiotic by Rat Liver Microsomes," *Free Radic. Biol. Med.* 22(3):439-446.

Redd, M.J. et al. (Apr. 25, 1997). "A Complex Composed of Tup1 and Ssn6 Represses Transcription *in Vitro,*" *J. Biol. Chem.* 272(17):11193-11197.

Reddy, V.K. et al. (1998). "Conformationally Restricted Analogues of $^1N, ^{12}N$-Bisethylspermine:Synthesis and Growth Inhibitory Effects on Human Tumor Cell Lines," *J. Med. Chem.* 41(24):4723-4732.

Reddy, V.K. et al. (2001). "*Cis*-Unsaturated Analogues of 3,8,13,18,23-Pentaazapentacosane (BE-4-4-4-4): Synthesis and Growth Inhibitory Effects on Human Prostate Cancer Cell Lines," *J. Med. Chem.* 44(3):404-417.

Redgate, E.S. et al. (1995). "Polyamines in Brain Tumor Therapy," *J. Neuro-Oncol.* 25(2):167-179.

Rihová, B. et al. (1993). "Targetable Photoactivatable Drugs. 3. In Vitro Efficacy of Polymer Bound Chlorin $e_s$ Toward Human Hepatocarcinoma Cell Line (PLC/PRF/5) Targeted with Galactosamine and to Mouse Splenocytes Targeted with Anti-Thy 1.2 Antibodies," *J. Controlled Release* 25:71-87.

Saito, T. (Mar. 1988). "Ten Years of Anticancer Drug-Carboquone," *Jpn. J. Cancer Chemother.* 15(3):549-554. (English abstract included on last page of document).

Salaün, J. (1997). "Synthetic Potential and Bioactivity of Cyclopropanes," *Russian Journal of Organic Chemistry* 33(6):742-780.

Salaün, J. (2000). "Cyclopropane Derivatives and Their Diverse Biological Activities," *Topics in Current Chemistry* 207:1-67.

Salaün, J. et al. (1995). "Biologically Active Cyclopropanes and Cyclopropenes," *Current Medicinal Chemistry* 2(1):511-542.

Shappell, N.W. et al. (1992). "Differential Effects of the Spermine Analog, $N^1, N^{12}$-Bis(ethyl)-spermine, on Polyamine Metabolism and Cell Growth in Human Melanoma Cell Lines and Melanocytes," *Anticancer Research* 12(4):1083-1089.

Sharma, A. et al. (Aug. 1997). "Antitumor Efficacy of $N^1, N^{11}$-Diethylnorspermine on a Human Bladder Tumor Xenograft in Nude Athymic Mice," *Clin. Cancer Res.* 3:1239-1244.

Sicuro, T. et al. (1987). "Dark- and Light-Interaction of Porphyrins with Malignant Cell Compartment," *Medicine Biologie Environnement* 15:67-70.

Singh, S. et al. (Nov. 15, 1996). "Capsaicin (8-Methyl-N-Vanillyl-6-Nonenamide) is a Potent Inhibitor of Nuclear Transcription Factor-$\kappa$B Activation by Diverse Agents," *J. Immunol.* 157(10):4412-4420.

Sinha, A.A. et al. (1995). "Cathepsin B in Angiogenesis of Human Prostate: An Immunohistochemical and Immunoelectron Microscopic Analysis," *Anat. Rec.* 241:353-362.

Sinha, A.A. et al. (1995). "Immunohistochemical Localization of Cathepsin B in Neoplastic Human Prostate," *The Prostate* 26:171-178.

Snyder, R.D. et al. (1994). "Anti-Mitochondrial Effects of Bisethyl Polyamines in Mammalian Cells" *Anticancer Res.* 14:347-356.

Snyder, R.D. et al. (May 15, 1991). "Effects of Polyamine Analogs on the Extent and Fidelity of In Vitro Polypeptide Synthesis," *Biochem. Biophys. Res. Commun.* 176(3):1383-1392.

Splinter, T.A.W. et al. (1986). "Phase I Study of Alpha-difluoromethylornithine and Methyl-GAG," *Eur. J. Cancer Clin. Oncol.* 22(1):61-67.

Stemberg, E. et al. (1996). "Pyrrolic Photosensitizers," *Current Medicinal Chemistry* 3(4):239-272.

Sun, J.S. et al. (1998). "A Preparative Synthesis of Lapachol and Related Naphthoquinones," *Tetrahedron Letters* 39:8221-8224.

Takenaka, S. et al. (1996). "Construction of a Dimeric DNA-Binding Peptide Model by Peptide-Anthraquinone Conjugation," *Int. J. Pept. Prot. Res.* 48(5):397-400.

Takuwa, A. et al. (1986). "Structural Influences on the Isomerization of 4-Benzyl- and 4-Allyl-1,2-naphthoquinones to Quinonemethides and their Stereochemistry," *J. Chem. Soc. 1*:1627-1631.

Takuwa, A. et al. (Sep. 1986). "The Addition of Alcohol to 1,2-Naphthoquinone Promoted by Metal Ions. A Facile Synthesis of 4-Alkoxy-1,2-naphthoquinones," *Bull. Chem. Soc. Jpn.* 59(9):2959-2961.

Valasinas, A. et al. (2001). "Conformationally Restricted Analogues of $^1N, ^{14}N$-Bisethylhomospermine (BE-4-4-4): Synthesis and Growth Inhibitory Effects on Human Prostate Cancer Cells," *J. Med. Chem.* 44(3):390-403.

Valasinas, A. et al. (2003). "Long-Chain Polyamines (Oligoamines) Exhibit Strong Cytotoxicities Against Human Prostate Cancer Cells," *Bioorganic and Medicinal Chemistry* 11:4121-4131.

Vonarx-Coinsman, V. et al. (1995). "HepG2 Human Hepatocarcinoma Cells: an Experimental Model for Photosensitization by Endogenous Porphyrins," *J. Photochem. and Photobiol. B:Biology*, 30:201-208.

Warnser, C.C. et al. (1989). "Thin-Film Composite Membranes for Artificial Photosynthesis. Final Report, Jul. 15, 1985-Mar. 31, 1989," *National Technical Information Service*, 41 pages.

Watt, K.W.K. et al. (May 1986). "Human Prostate-Specific Antigen: Structural and Functional Similarity with Serine Proteases," *Proc. Natl. Acad. Sci. USA* 83:3166-3170.

Webb, H.K. et al. (1999). "1-(N-Alkylamino)-11-(N-ethylamino)-4,8-diazaundecanes: Simple Synthetic Polyamine Analogues That Differentially Alter Tubulin Polymerization," *J. Med. Chem.* 42(8):1415-1421.

Woodburn, K. W. et al. (1992). "Evaluation of Porphyrin Characteristics Required for Photodynamic Therapy," *Photochemistry and Photobiology* 55(5):697-704.

Wunz, T.P. et al., (1987) "New Antitumor Agents Containing the Anthracene Nucleus," *J. Med. Chem.* 30(8):1313-1321.

Yan, S. et al. (Feb. 1998). "Cathepsin B and Human Tumor Progression," *Biol. Chem.* 379:113-123.

Yuan, Z-M. et al. (1994). "Cytotoxic Activity of $N^1$- and $N^8$-Aziridinyl Analogs of Spermidine," *Biochem. Pharmacol.* 47(9):1587-1592.

Zagaja, G.P. et al. (1998). "Effects of Polyamine Analogues on Prostatic Adenocarcinoma Cells in Vitro and in Vivo," *Cancer Chem. Pharm.* 41(6):505-512.

Burns, M.R. et al. (2001). "Amino Acid/Spermine Conjugates: Polyamine Amides as Potent Spermidine Uptake Inhibitors," *J. Med. Chem.* 44(22):3632-3644.

Bercovici D. et al. (1987). "Transglutaminase-Catalyzed Incorporation of Lysine Oligomers into Casein," *J. Agric. Food Chem.* 35(3):301-304.

\* cited by examiner

SCHEME 1

SCHEME 2

SCHEME 3

SCHEME 4

SCHEME 5

SCHEME 6

SCHEME 7

SCHEME 8

SCHEME 9

SCHEME 10

SCHEME 11

SCHEME 12

SCHEME 13

SCHEME 14

SCHEME 15

SCHEME 16

SCHEME 17

SCHEME 18

SCHEME 19

SCHEME 20

SCHEME 21

SCHEME 22

SCHEME 23

SCHEME 24

SCHEME 26

POLYAMINE ANALOG-AMINO ACID CONJUGATES USEFUL AS ANTICANCER AGENTS

CROSS-REFERENCE TO RELATED APPLICATIONS

This is a national stage under 35 USC § 371 of International Application PCT/US01/43585, filed on Nov. 8. 2001, and published in the English language on May 16, 2002, which claims priority benefit of U.S. Provisional Patent Application Ser. No. 60/246,804, filed Nov. 8, 2000, and also of U.S. patent application Ser. No. 09/56 1,172 filed Apr. 27, 2000, now U.S. Pat. No. 6,649,587 which in turn claims priority to U.S. Provisional Patent Application Ser. Nos. 60/131,809, 60/131,779 and 60/131,842, all filed Apr. 30, 1 999. The entire contents of those applications are hereby incorporated by reference herein.

STATEMENT OF RIGHTS TO INVENTIONS MADE UNDER FEDERALLY SPONSORED RESEARCH

Not applicable

TECHNICAL FIELD

This invention relates to compositions in which a polyamine or polyamine analog is conjugated to an amino acid. This invention also relates to uses of these conjugates as anticancer and antitumor agents.

BACKGROUND OF THE INVENTION

Cancer is one of the leading causes of death in the developed world. Approximately one-quarter of the deaths in the United States in 1997 were due to cancer, making it the second most common cause of death after heart disease. Accordingly, development of new and effective treatments for cancer is a high priority for health care researchers.

Cancer is often treated by using chemotherapy to selectively kill or hinder the growth of cancer cells, while having a less deleterious effect on normal cells. Chemotherapeutic agents often kill rapidly dividing cells, such as cancer cells; cells which are dividing less rapidly are affected to a lesser degree. Other agents, such as antibodies attached to toxic agents, have been evaluated for use against cancers. These agents target the cancer cells by making use of a characteristic specific to the cancer, for example, higher-than-normal rates of cell division, or unique antigens expressed on the cancer cell surface.

Polyamines and polyamine analogs have been proposed as anti-cancer agents. Natural polyamines, e.g., spermidine, norspermidine, homospermidine, 1,4-diaminobutane (putrescine), and spermine, are simple aliphatic amines produced in eukaryotic cells by a highly regulated metabolic apparatus. Polyamine levels and the activity of the polyamine biosynthetic apparatus tend to be high in dividing mammalian cells and low in quiescent cells. Populations of cells depleted of their polyamine content stop growing and may die. Janne et al. (1978) *A. Biochim. Biophys. Acta.* 473:241 and Pegg et al. (1982) *Ami. J. Cell. Physiol.* 243:212–221. Polyamines are reviewed in Morgan (1998) *Methods. Mol. Biol.* 79:3–30.

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules, such as nucleic acids, by anion neutralization. Hafner et al. (1979) *J. Biol. Chem.* 254:12419; Pohjatipelto et al. (1981) *Nature* 293:475; Mamont et al. (1978) *Biochem. Biophys. Res. Commun.* 81:58; Bloomfield et al. (1981) in *Polyamines in Biology and Medicine*, Morris et al., Eds., Dekker, N.Y., pp. 183–205.

A treatment approach has been devised based on the observation that increases in the polyamine pool suppress polyamine biosynthesis. Porter et al. (1988) in *Advances in Enzyme Regulation*, Pergamon Press, pp. 57–79. This approach attempts to identify polyamine analogs which down-regulate polyamine biosynthesis, but which do not perform the polyamine functions required for cell growth. BESPM, a N-bis(ethyl) analog of spermine, has served as a model compound for this strategy. BESPM rapidly suppresses polyamine biosynthetic enzymes, depletes natural polyamine pools, and inhibits cell growth in vitro. Porter et al. (1987) *Cancer Res.* 47:2821–2825. In addition, BESPM suppresses polyamine uptake (Byers et al. (1990) *J. Physiol.* 142:460–467; and Kramer et al. (1993) *J. Cell. Physiol.* 115:399–407), and thus minimizes the ability of tumor cells to meet their polyamine requirement by taking them up from their environment. BESPM and related analogs also induce the polyamine metabolizing enzyme spermidine/spermine $N^1$-acetyltransferase (SSAT) in certain human carcinoma cell lines.

BESPM and other polyamine analogs have been used, or proposed for use, in treating a large variety of diseases, including a number of different cancers. See International Patent Application WO 00/66587, and U.S. Pat. Nos. 5,889,061, 5,880,161, and 5,541,230. Polyamine analogs demonstrated, for example, potent antitumor activity against several melanoma cell lines and tumors in vitro (Porter et al. (1991) *Cancer Res.* 51:3715–3720; Shappell et al. (1992) *Anticancer Res.* 12:1083–1090) and in vivo using tumors growing as xenografts in athymic mice (Bernacki et al. (1992) *Cancer Res.* 52:2424–2430; Porter et al. (1993) *Cancer Res.* 53:581–586). Potent antitumor activity of bisethyl spermine analogs has also been demonstrated for pancreatic cancer cell lines in vitro (Chang et al. (1992) *Cancer Chemother. Pharmacol.* 30:183–188) and in vivo (Chang et al. (1992) *Cancer Chemother. Pharmacol.* 30:179–182). Polyamine analogs have also been suggested for use in treating brain tumor therapy. Redgate et al. (1995) *J. Neurooncol.* 25:167–79. In addition to being useful against cancers of the brain, pancreas, and skin, polyamine analogs are also useful against cancers of the bladder, bone, breast, colon, digestive tract, lung and ovaries. Chang et al. (1993) *J. Urol.* 150:1293–7; Snyder et al. (1994) *Anticancer Res.* 14:347–56; Yuan et al. (1994) *Biochem. Pharmacol.* 47:1587–92; Davidson et al. (1993) *Cancer Res.* 53:2071–5; Berchtold et al. (1998) *J. Cell. Physiol.* 174:380–6; Porter et al. (1988) *Adv. Exp. Med Biol.* 250:677–90; U.S. Pat. Nos. 5,498,522 and 5,374,658. U.S. Pat. No. 5,498,522 presents the use of spermidine/spermine $N^1$-acetyltransferase as a prognostic indicator of the efficacy of a polyamine analog against a malignant tumor.

Polyamine analogs have been used to treat cancer of the prostate )Mi et al. (1988) *Prostate* 34:51–60). Polyamines are produced in large amounts by the prostate gland and are abundant in the seminal fluid (Herr et al. (1984) *Cancer* 53:1294–8). Polyamine analogs such as BE-4444, BE-373, and BE-333 are particularly effective in inhibiting prostate xenograft tumors in nude mice; see Zagaja et al. (1998) *Cancer Chem. Pharm.* 41:505–512; Jeffers et al. (1997) *Cancer Chem. Pharm.* 40:172–179; Feuerstein et al. (1991) *J. Cell. Biochem.* 46:37–47; and Marton et al. (1995) *Ann. Rev. Pharm. Toxicol.* 35:55–91.

Polyamines and their analogs can be administered alone or in conjunction with additional agents. For example, therapeutic polyamines can be administered along with 1,3-bis (2-chloroethyl)-1-nitrosourea. U.S. Pat. No. 5,541,230. In treating cancer, polyamines can be co-administered with various cytotoxic agents, including antineoplastic vinca alkaloids, antibiotics, antimetabolites, and platinum coordination complexes. U.S. Pat. No. 5,654,287.

It would be advantageous to develop novel polyamine analogs for use as anti-cancer therapies. This invention describes All references cited herein are hereby incorporated by reference in their entirety.

SUMMARY OF THE INVENTION

The invention provides compositions in which a polyamine or polyamine analog is conjugated to one or more amino acids. The invention also provides methods for treatment of cancer by administering one or more compositions of the invention. The polyamine or polyamine analog can be combined with a pharmaceutically acceptable carrier or can be present as a pharmaceutically acceptable salt.

The polyamine or polyamine analog can be linked to an amino acid via an amide linkage between a primary or secondary amine group of the polyamine or polyamine analog, and the carboxy terminus of the amino acid, for use in methods of the current invention. If the amino acid contains more than one carboxyl group (for example, aspartatic acid or glutamic acid), the amide linkage can be to any of the carboxyl groups present in the amino acid. In one embodiment, the amino acid is conjugated to the polyamine or polyamine analog at one and only one of the exterior nitrogens of the polyamine or polyamine analog. In another embodiment, two amino acids are conjugated to the polyamine or polyamine analog, one amino acid at each exterior nitrogen of the polyamine or polyamine analog. The polyamine or polyamine analog can contain one or more hydroxy groups, and can be linked to the carboxy terminus of one or more amino acids by an ester linkage through the one or more hydroxy groups. In another embodiment, the polyamine or polyamine analog is conformationally restricted.

In another embodiment, the invention encompasses compositions comprising a polyamine analog-amino acid conjugate of the formula:

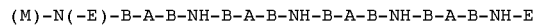

or

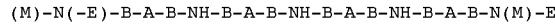

wherein each M is independently an amino acid, each A is independently selected from the group consisting of a single bond, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and any salt or stereoisomer thereof.

In another embodiment, the invention encompasses compositions comprising a polyamine analog-amino acid conjugate of the formula:

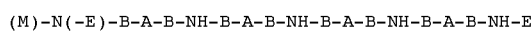

or

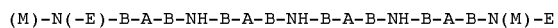

wherein each M is independently an amino acid, each A is independently selected from the group consisting of a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and any salt or stereoisomer thereof.

In another embodiment, the invention encompasses compositions comprising a polyamine analog-amino acid conjugate of the formula:

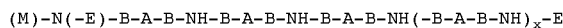

or

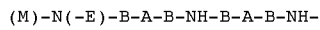

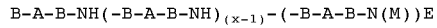

wherein each M is independently an amino acid, each A is independently selected from the group consisting of: a single bond, $C_6$–$C_2$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and x is an integer from 2 to 16; and any salt or stereoisomer thereof.

In another embodiment, the invention encompasses compositions comprising a polyamine analog-amino acid conjugate of the formula:

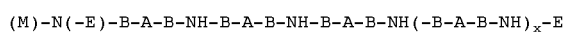

or

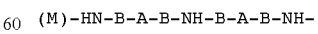

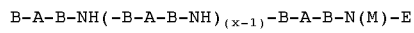

wherein each M is independently an amino acid, each A is independently selected from the group consisting of: a single bond, $C_6$–$C_2$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and x is an integer from 2 to 16; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and any salt or stereoisomer thereof.

In another embodiment, the invention encompasses compositions comprising a polyamine analog-amino acid conjugate of the formula:

(M)E-NH-B-A-B-NH-B-A-B-NH-B-A-B-NH(-B-A-B-NH)$_x$-E(M)

or (M)E-NH-B-A-B-NH-B-A-B-NH-B-A-B-NH(-B-A-B-NH)$_x$-E wherein each M is independently an amino acid, wherein each A is independently selected from the group consisting of: a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of $C_1$–$C_6$ alkyl, $C_1$–$C_6$ alkanol, $C_3$–$C_6$ cycloalkanol, and $C_3$–$C_6$ hydroxyaryl, and the amino acid(s) is linked to the polyamine analog via an ester linkage at the E group hydroxyl(s), with the proviso that each E bearing an amino acid is selected from $C_1$–$C_6$ alkanol, $C_3$–$C_6$ cycloalkanol, and $C_3$–$C_6$ hydroxyaryl; and x is an integer from 0 to 16; and any salt or stereoisomer thereof.

In another embodiment, the invention encompasses compositions comprising a polyamine analog-amino acid conjugate of the formula:

(M)E-NH-B-A-B-NH-B-A-B-NH-B-A-B-NH(-B-A-B-NH)$_x$-E(M)

or (M)E-NH-B-A-B-NH-B-A-B-NH-B-A-B-NH(-B-A-B-NH)$_x$-E wherein each M is independently an amino acid, wherein each A is independently selected from the group consisting of: a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of $C_1$–$C_6$ alkyl, $C_1$–$C_6$ alkanol, $C_3$–$C_6$ cycloalkanol, and $C_3$–$C_6$ hydroxyaryl, with the proviso that each E bearing an amino acid is selected from $C_1$–$C_6$ alkanol, $C_3$–$C_6$ cycloalkanol, and $C_3$–$C_6$ hydroxyaryl; and the amino acid(s) is linked to the polyamine analog via an ester linkage to at least one E group hydroxyl(s); and x is an integer from 0 to 16; and any salt or stereoisomer thereof.

In another embodiment, the invention encompasses compositions comprising a polyamine analog-amino acid conjugate of the formula:

(M)-N(-E)-D-NH-B-A-B-NH-D-NH-E or (M)-N(-E)-D-NH-B-A-B-NH-D-N(M)-E wherein each M is independently an amino acid; A is selected from the group consisting of $C_2$–$C_6$ alkynyl; each B is independently selected from the group consisting of: a single bond, $C_1$–$C_6$ alkyl, and $C_2$–$C_6$ alkenyl; each D is independently selected from the group consisting of $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkenyl, and $C_3$–$C_6$ cycloaryl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and any salt or stereoisomer thereof.

In another embodiment, the invention encompasses compositions comprising a polyamine analog-amino acid conjugate of the formula:

(M)-N(-E)-B-A-B-NH-F-NH-B-A-B-NH-E or (M)-N(-E)-B-A-B-NH-F-NH-B-A-B-N(M)-E wherein each M is independently an amino acid; F is selected from the group consisting of $C_1$–$C_6$ alkyl; each A is independently selected from the group consisting of: a single bond, $C_1$–$C_6$ alkyl; $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl;each B is independently selected from the group consisting of: a single bond, $C_1$–$C_6$ alkyl, and $C_2$–$C_6$ alkenyl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and any salt or stereoisomer thereof.

In another embodiment, the invention encompasses compositions comprising a polyamine analog-amino acid conjugate of the formula:

(M)-N(-E)-B-A-B-NH-F-NH-B-A-B-NH-E or (M)-N(-E)-B-A-B-NH-F-NH-B-A-B-N(M)-E wherein each M is indepedently an amino acid; wherein F is selected from the group consisting of $C_1$–$C_6$ alkyl; each A is independently selected from the group consisting of: a single bond, $C_1$–$C_6$ alkyl; $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and any salt or stereoisomer thereof.

In another embodiment, the invention encompasses compositions comprising a polyamine analog-amino acid conjugate of the formula:

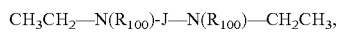

where each $R_{100}$ is independently chosen from H, $C_1$–$C_8$ alkyl, and an amino acid, with the proviso that at least one $R_{100}$ be an amino acid; and where J is selected from {$C_1$–$C_8$ alkyl-[N($R_{101}$)—($C_1$–$C_8$ alkyl)]$_k$}, where each $R_{101}$ is independently selected from H and $C_1$–$C_8$ alkyl, and where k is an integer between 0 and 15.

In further embodiments, both $R_{100}$ groups can be amino acids; one and only one $R_{100}$ can be an amino acid, or one and only one $R_{100}$ is an amino acid and the other $R_{100}$ is H.

In another embodiment, the invention encompasses compositions comprising a polyamine analog-amino acid conjugate of the formula:

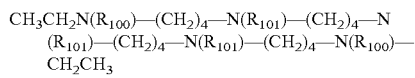

where each $R_{100}$ is independently chosen from H, $C_1$–$C_8$ alkyl, and an amino acid, with the proviso that at least one $R_{100}$ be an amino acid; and each $R_{101}$ is independently chosen from H and $C_1$–$C_8$ alkyl.

In another embodiment, the invention encompasses any one or any combination of the foregoing embodiments, further comprising a pharmaceutically acceptable excipient or carrier.

In another embodiment, the invention encompasses a method of treating cancer in an individual, comprising administering to the individual an effective amount of any one or any combination of the foregoing compositions. The individual can be a mammal, such as a human.

In any of the foregoing embodiments, when the compound contains one or more chiral centers, the invention encompasses any and all of the pure enantiomers and diastereomers of the compound, as well as racemic mixtures of the compounds, and/or any mixture or combination of diastereomers.

In any of the foregoing embodiments, the amino acid can chosen from the set of all amino acids; the set of all amino acids with either amide-containing or basic side chains; the set of glutamine, asparagine, lysine, ornithine, arginine, histidine, or citrulline; the set of D-glutamine or L-glutamine; or from the single-member set of L-glutamine; and all stereoisomers and salts thereof, unless a stereoisomer is specifically excluded from the set.

In any of the foregoing embodiments, the amino acid can be chosen from the set of all amino acids, with the proviso that glutamine is excluded; the set of all amino acids with either amide-containing or basic side chains, with the proviso that glutamine is excluded; the set of asparagine, lysine, ornithine, arginine, histidine, or citrulline; or from the single-member set of D-glutamine; and all stereoisomers and salts thereof, unless a stereoisomer is specifically excluded from the set.

In a subset of any of the foregoing embodiments, when the amino acid is linked to a nitrogen group of the polyamine or polyamine analog, the amino acid can be an alpha-amino acid, linked to the polyamine or polyamine analog via an amide linkage between the alpha-carboxyl group of the amino acid and the nitrogen of the polyamine or polyamine analog.

MODES FOR CARRYING OUT THE INVENTION

Figure 1:
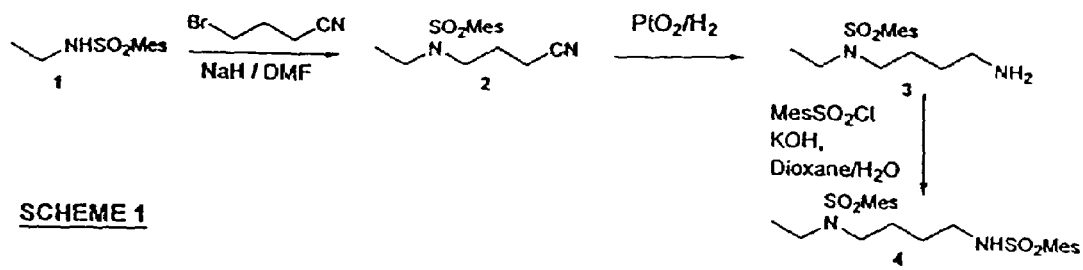
FIG. 1 illustrates synthetic methodology used to prepare polyamine or polyamine analog compounds useful in the invention.
Figure 1:
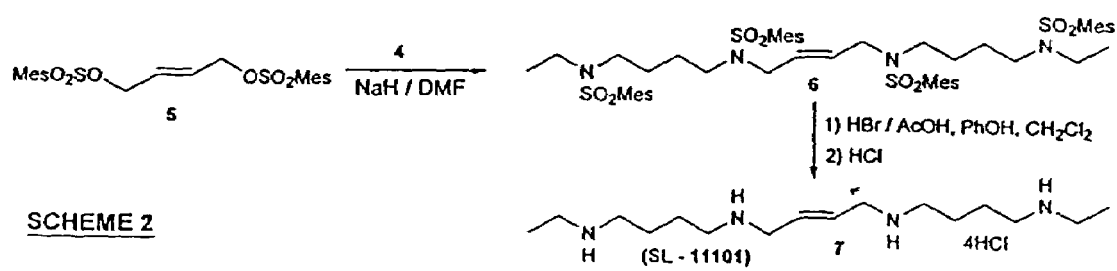
Figure 1:
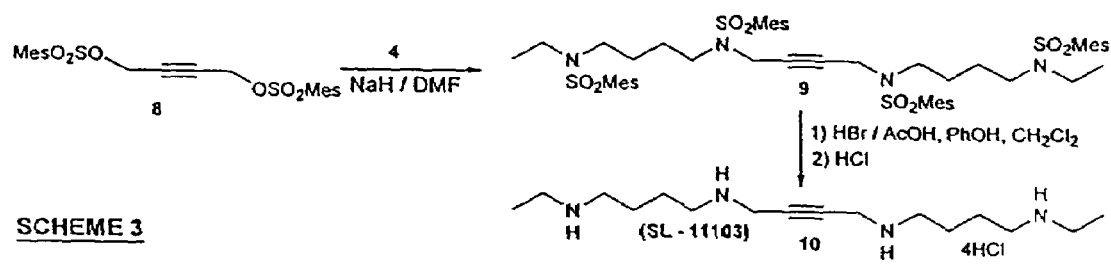
Figure 1:
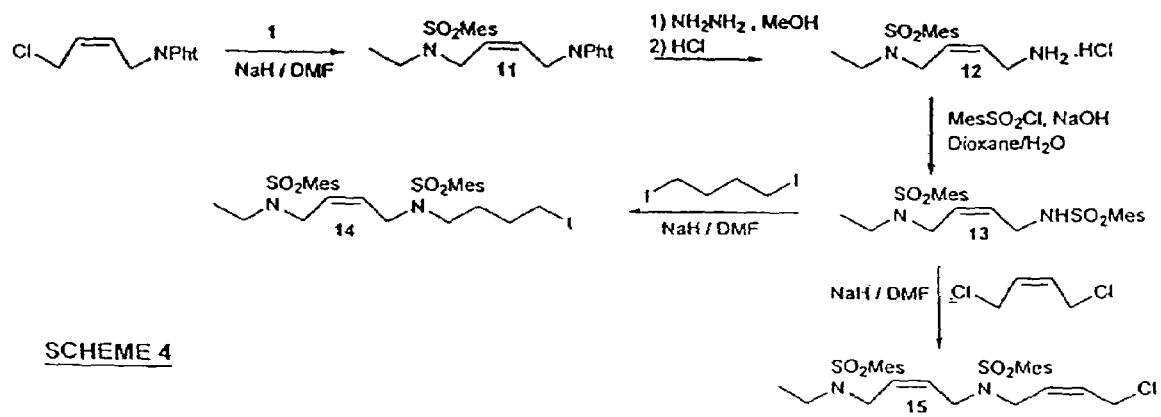
Figure 2:
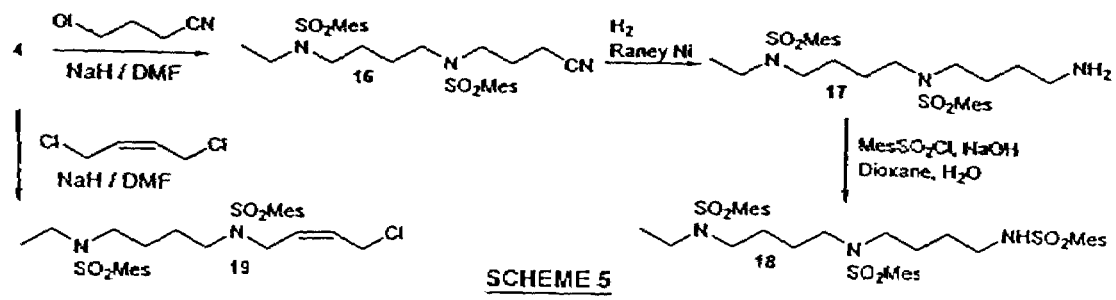
FIG. 2 illustrates additional synthetic methodology used to prepare polyamine or polyamine analog compounds useful in the invention.
Figure 2:
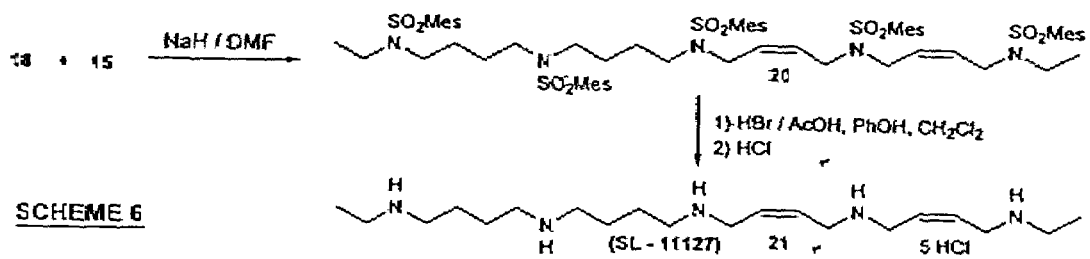
Figure 2:
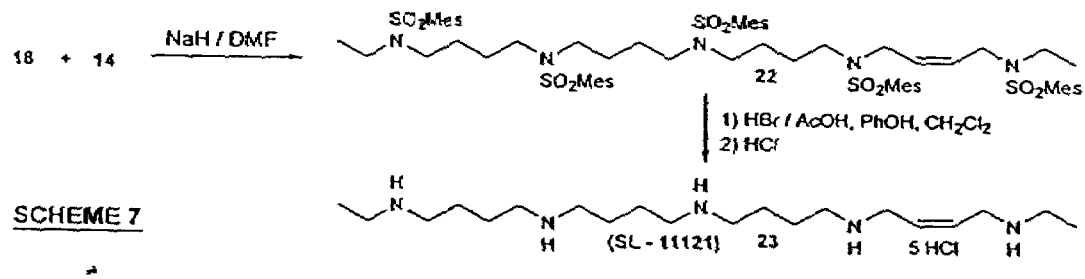
Figure 2:
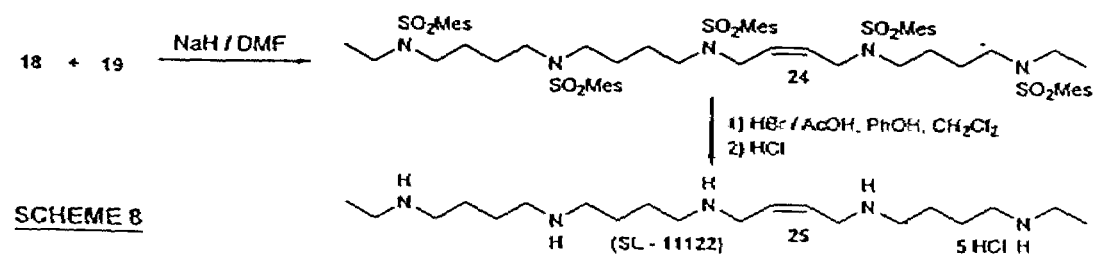
Figure 2:
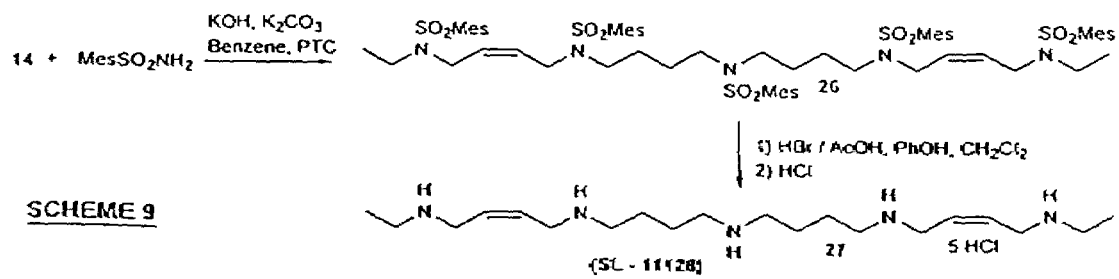
Figure 3:
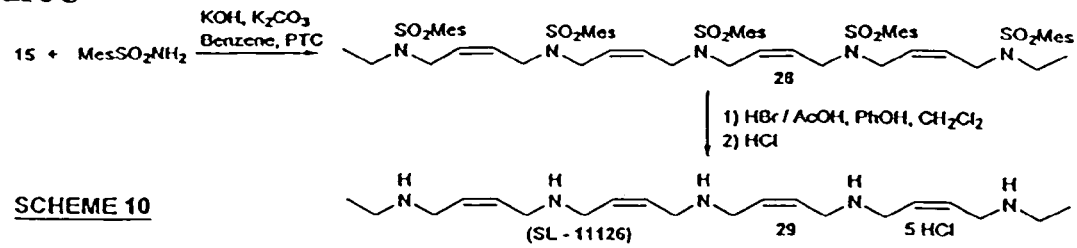
FIG. 3 illustrates additional synthetic methodology used to prepare polyamine or polyamine analog compounds useful in the invention.
Figure 3:
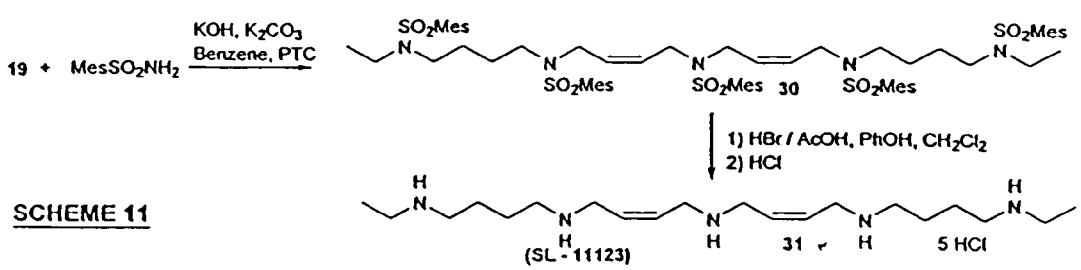
Figure 3:
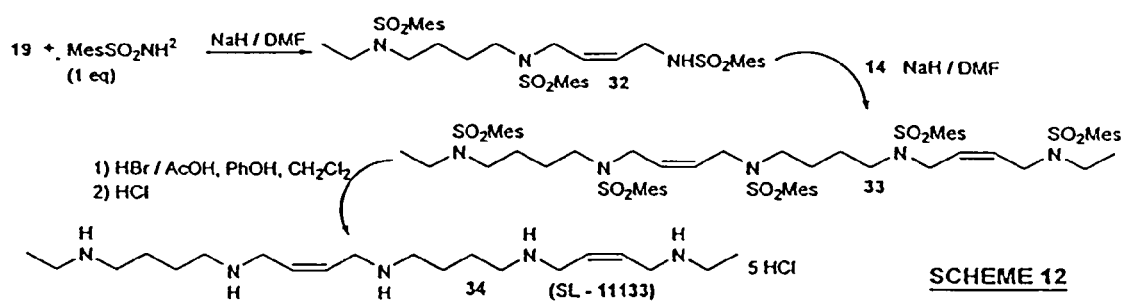
Figure 3:
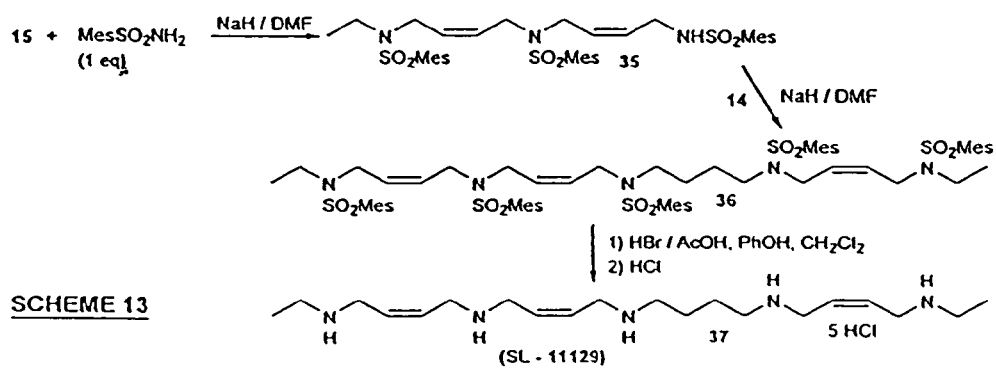
Figure 3:
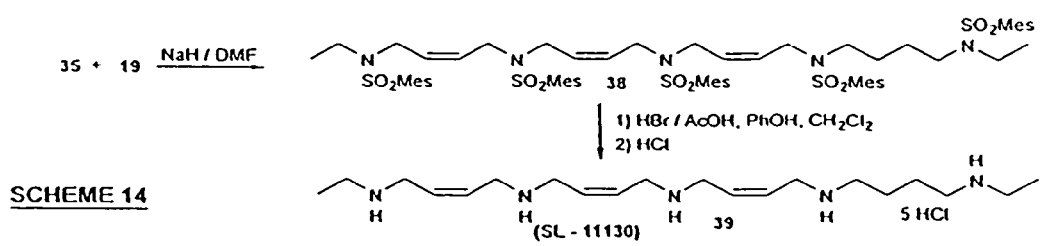
Figure 4:
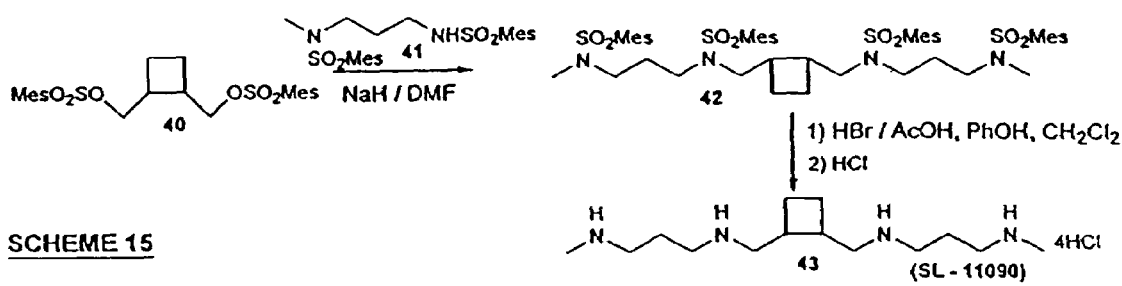
FIG. 4 illustrates additional synthetic methodology used to prepare polyamine or polyamine analog compounds useful in the invention.
Figure 4:
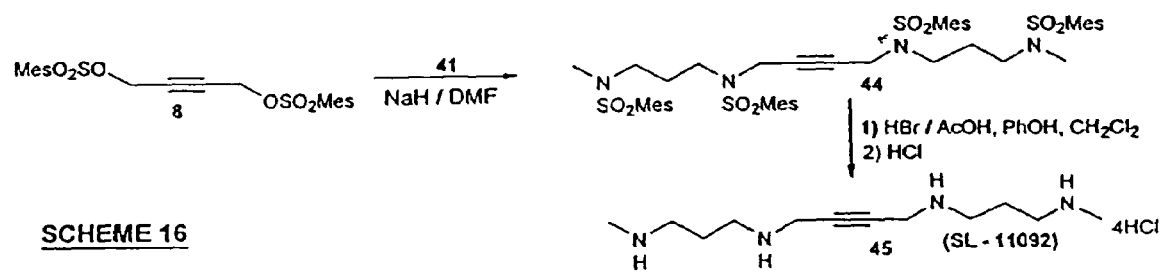
Figure 4:
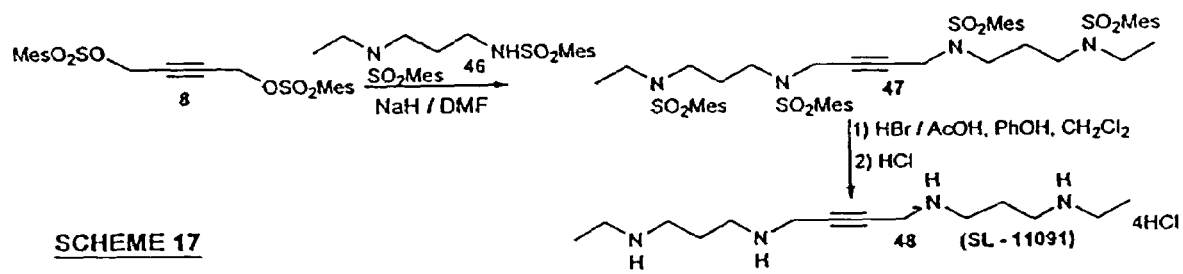
Figure 5:
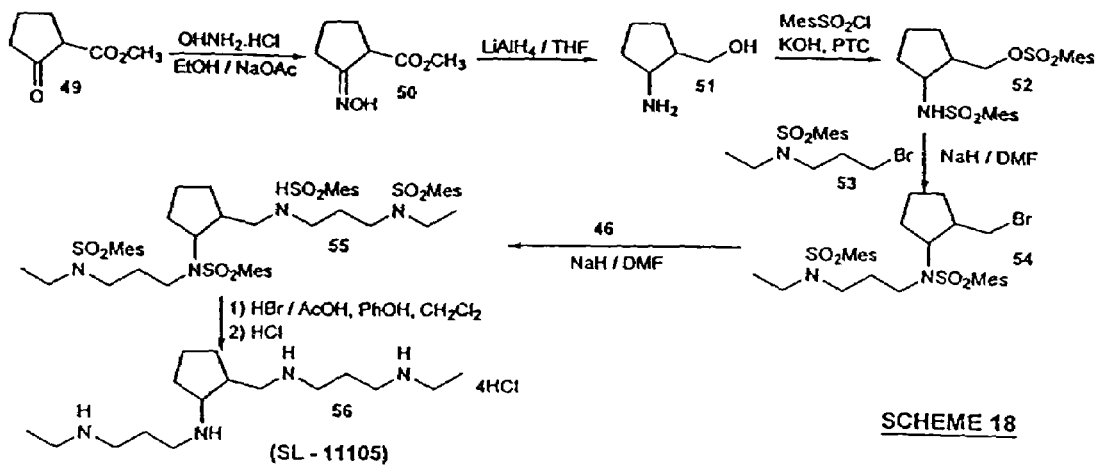
FIG. 5 illustrates additional synthetic methodology used to prepare polyamine or polyamine analog compounds useful in the invention.
Figure 5:
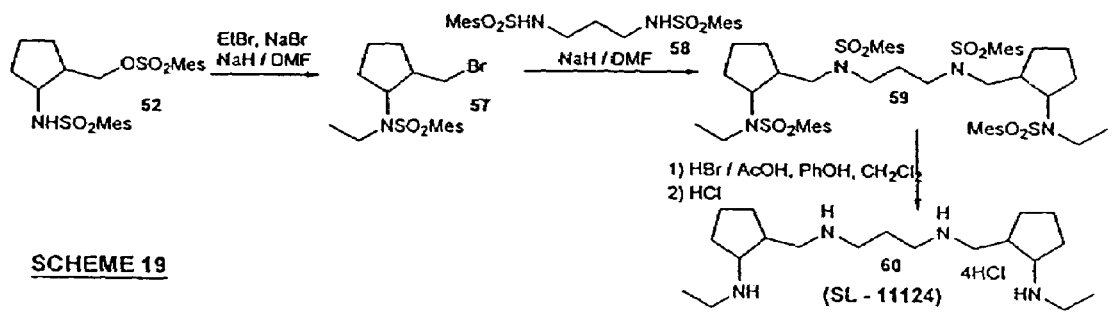
Figure 5:
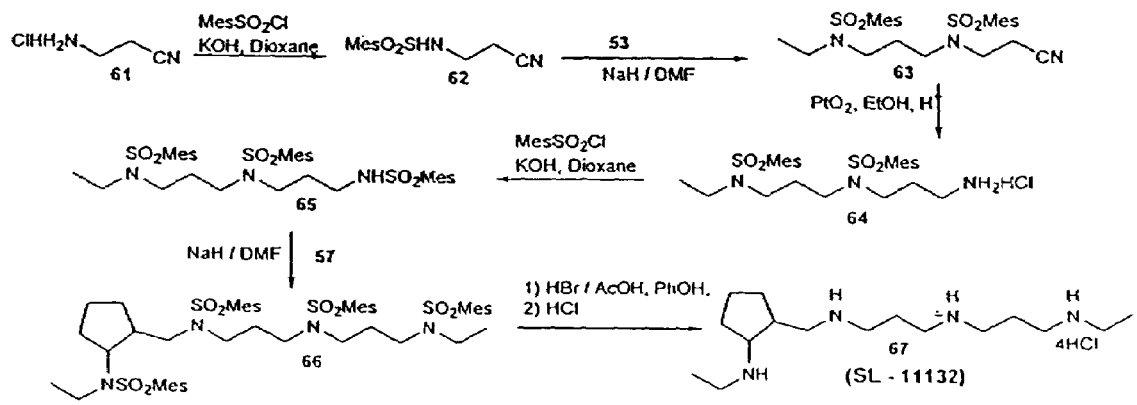
Figure 6:
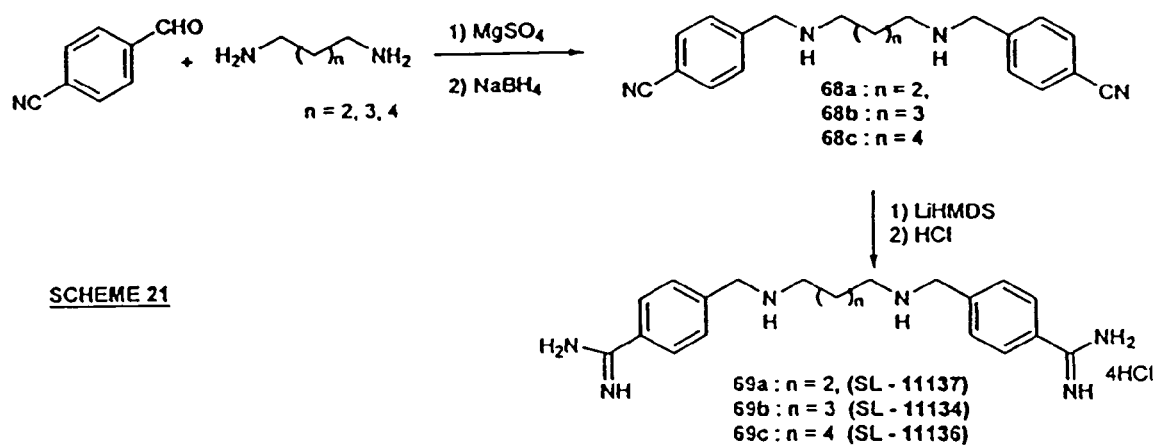
FIG. 6 illustrates additional synthetic methodology used to prepare polyamine or polyamine analog compounds useful in the invention.
Figure 7:
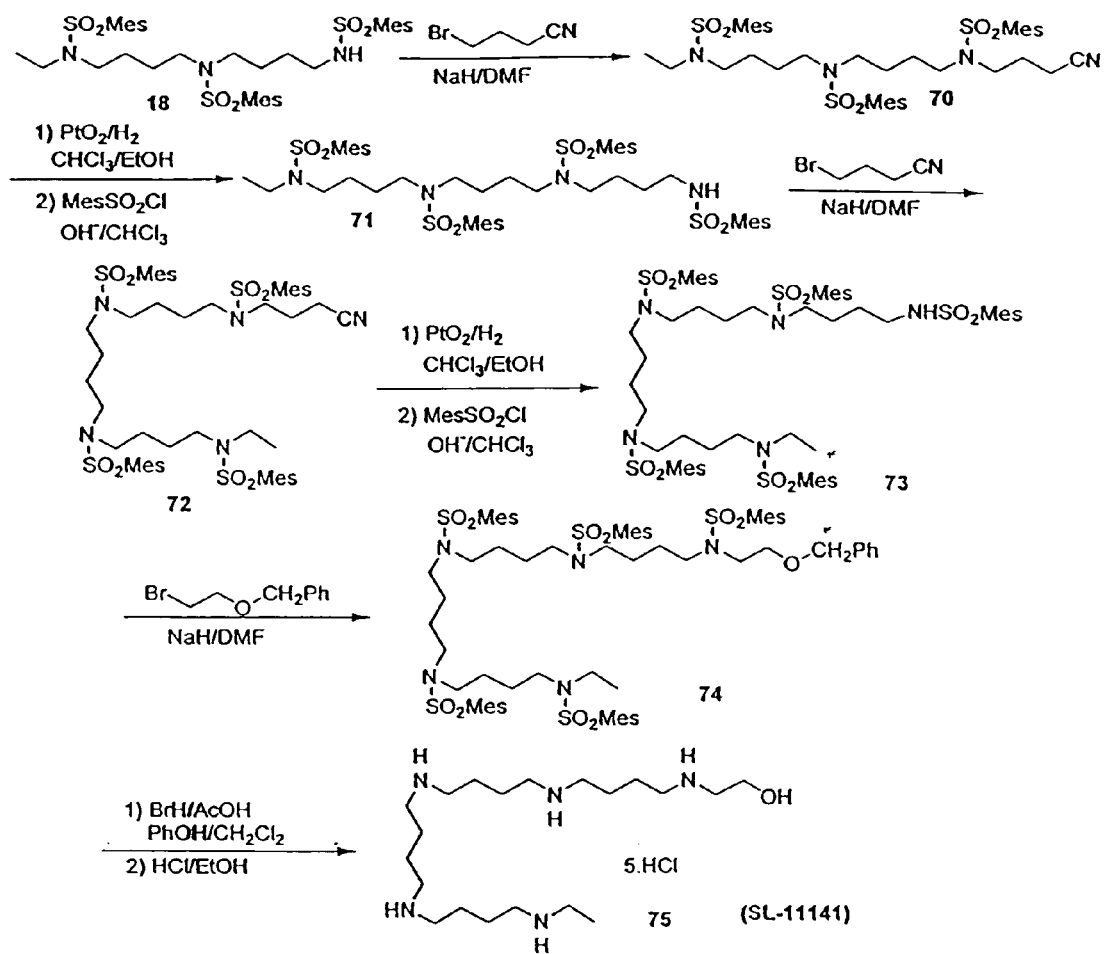
FIG. 7 illustrates additional synthetic methodology used to prepare polyamine or polyamine analog compounds useful in the invention.
Figure 7:
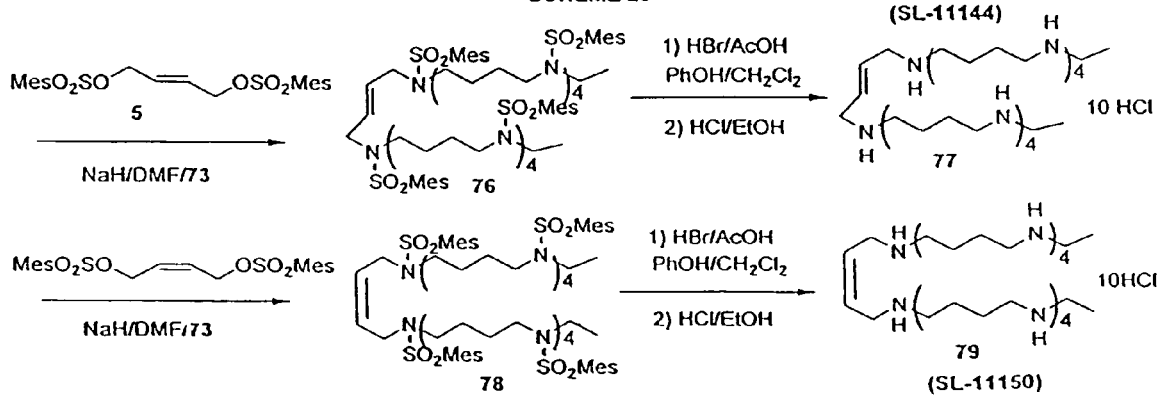
Figure 8A:
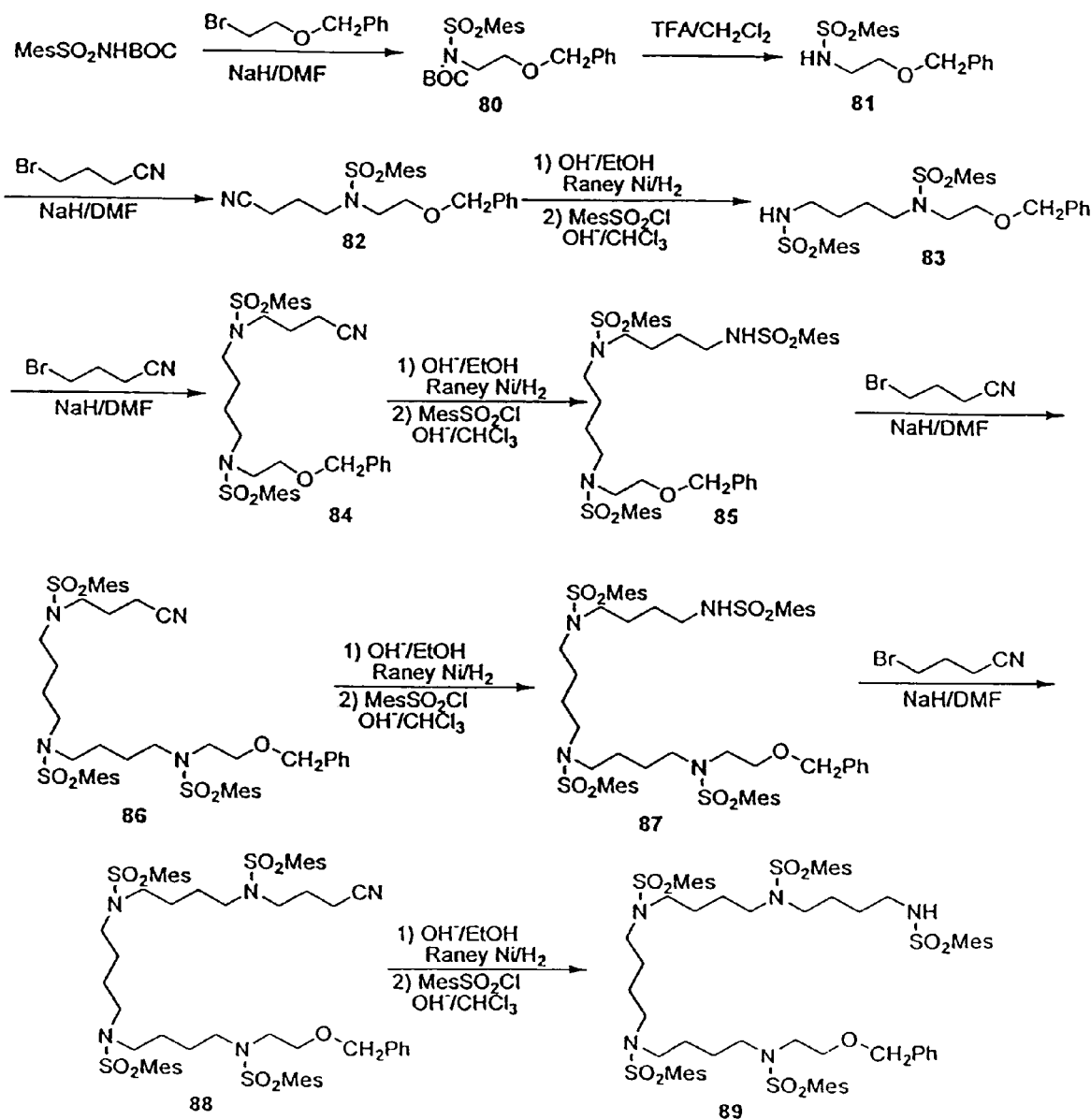
FIG. 8A illustrates additional synthetic methodology used to prepare polyamine or polyamine analog compounds useful in the invention.
Figure 8B:
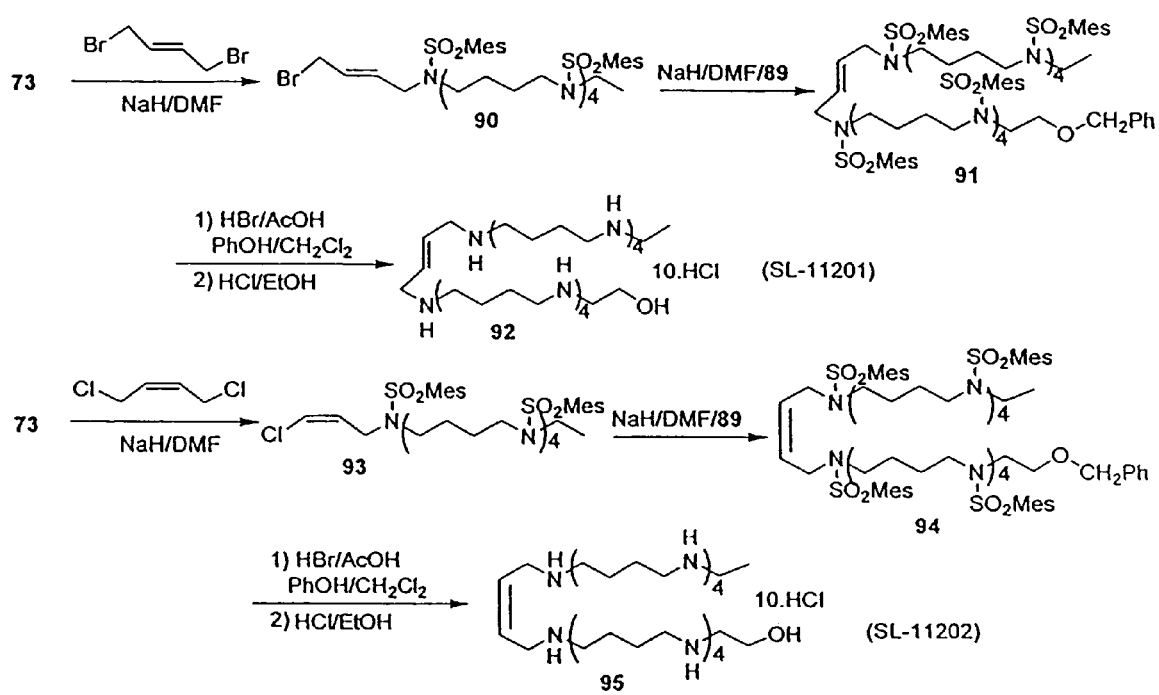
FIG. 8B illustrates additional synthetic methodology used to prepare polyamine or polyamine analog compounds useful in the invention.
Figure 9:
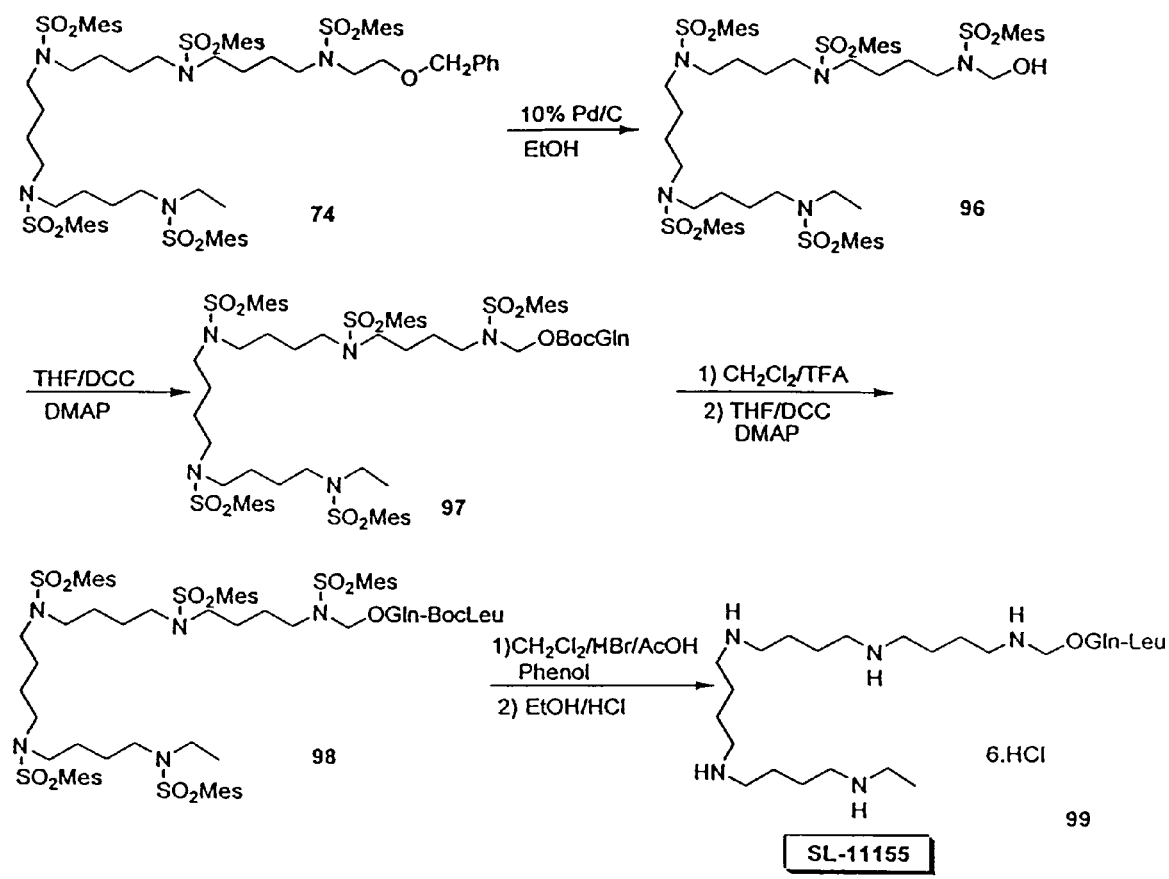
FIG. 9 depicts Scheme 25, illustrating the synthesis of an amino acid conjugated to a polyamine analog alchohol via an ester linkage.

The present invention encompasses polyamine analog conjugates in which a polyamine analog is conjugated to an amino acid. The conjugates of the invention are useful in treating cancer.

As discussed below, the polyamine analog can be any polyamine analog, including, but not limited to, 1, 12-Me$_2$-SPM, SL-11027, SL-11028, SL-11029, SL-11033, SL-11034, SL-11037, SL-11038, SL-11043, SL-11044, SL-11047, SL-11048, SL-11050, SL-11090, SL-11091, SL11092, SL-11093, SL-11094, SL-11098, SL-11099, SL-11100, SL-11101, SL-11102, SL-11103, SL-11104, SL-11105, SL-11108, SL-11114, SL-11118, SL-11119, SL-11121, SL-11122, SL-11123, SL-11124, SL-11126, SL-11127, SL-11128, SL-11129, SL-11130, SL-11132, SL-11133, SL-11134, SL-11136, SL-11137, SL-11141, SL-11144, SL-11150, SL-11201, and SL-11202. Preferably, the polyamine analog is conformationally restricted.

Definitions

By "polyamine analog" is meant an organic cation structurally similar but non-identical to polyamines such as spermine and/or spermidine and their precursor, diamine putrescine. By a "polyamine" is meant any of a group of aliphatic, straight-chain amines derived biosynthetically from amino acids; polyamines are reviewed in Marton et al. (1995) *Ann. Rev. Pharm. Toxicol.* 35:55–91. Polyamines cadaverine and putrescine are diamines produced by decarboxylation of lysine or ornithine, respectively. Putrescine is converted to spermidine, and spermidine to spermine, by the addition of an aminopropyl group. This group is provided by decarboxylated S-adenosyl methionine. Polyamine analogs, which can be branched or un-branched, include, but are not limited to, BE-4444 [1,19-bis(ethylamino)-5,10,15-triaza-nonadecane]; BE-333 [N1,N11-diethylnorspermine; DENSPM; 1,11-bis(ethylamino)-4,8-diazaundecane; thermine; Warner-Parke-Davis]; BE-33 [N1,N7-bis (ethyl) norspermidine]; BE-34 [N1,N8-bis (ethyl) spermidine]; BE44 [N1,N9-bis (ethyl) homospermidine]; BE-343 [N1,N12-bis (ethyl) spermine; diethylspermine-N1-N12; DESPM]; BE-373 [N,N'-bis(3-ethylamino) propyl)-1,7-heptane diamine, Merrell-Dow]; BE444 [N1,N14-bis (ethyl) homospermine; diethylhomospermine-N1-N14]; BE-3443 [1,17-bis (ethylamino)4,9,14triazaheptadecane]; BE4334 [1,17-bis (ethylamino)-5,9,13-triazaheptadecane]; 1,12-Me$_2$-SPM [1,12-dimethylspermine]; various polyamine analogs disclosed in WO 98/17624 and U.S. Pat. No. 5,889,061; and the various novel polyamine analogs illustrated in the Figures and described herein, including, but not limited to, compounds designated SL-11027, SL-1 1028, SL-11029, SL11033, SL-11034, SL-11037, SL111038, SL-11043, SL-11044, SL-11047, SL-11048, SL-11050, SL-11090, SL-11091, SL-11092, SL-11093, SL-11094, SL-11098, SL-11099, SL-11100, SL-11101, SL-11102, SL-11103, SL-11104, SL-11105, SL-11108, SL-11114, SL-11118, SL-11119, SL-11121, SL-11122, SL-11123, SL-11124, SL-11126, SL-11127, SL-11128, SL-11129, SL-11130, SL-11132, SL-11133, SL-11134, SL-11136, SL-11137, SL-11141, SL-11144, SL-11150, SL-11201, and SL-11202. Additional polyamine analogs useful for this invention are known in the art, such as O'Sullivan et al. (1997) *Bioorg. Med Chem.* 5:2145–2155; and Mukhopadhyaya et al. (1995) *Exp. Parasit.* 81:39–46; and U.S. Pat. No. 4,935,449.

By "conformationally restricted" is meant that, in a polyamine analog, at least two amino groups are locked or limited in spatial configuration relative to each other. The relative movement of two amino groups can be restricted, for example, by incorporation of a cyclic or unsaturated moiety between them (exemplified, but not limited to, a ring, such as a three-carbon ring, four-carbon ring, five-carbon-ring, six-carbon ring, or a double or triple bond, such as a double or triple carbon bond). Groups restricting conformational flexibility by means of steric hindrance, yet structurally favorable to the anti-proliferative effects, can also be used according to the invention. A "conformationally restricted" polyamine analog can comprise at least two amino groups which are conformationally restricted relative to each other, but can also further comprise amino groups which are not conformationally restricted relative to each other. Flexible molecules such as spermine and BE444 can have a myriad of conformations and are therefore not conformationally restricted.

For the purposes of this invention, amino acids are defined to include the twenty genetically-encoded amino acids (the twenty genetically encoded amino acids include the imino acid proline), other naturally-occurring amino acids, such as ornithine and citrulline, non-naturally occurring amino acids, and all stereoisomers and salts thereof. One embodiment of the invention utilizes the subset of the amino acids which have either amide-containing or basic side chains (amino acids containing basic side chains include, but are not limited to, amino acids with amino-containing side chains such as homolysine, amino acids with ureido-containing side chains such as citrulline, amino acids containing imidazole side chains such as histidine, or amino acids containing guanidino-containing side chains, such as alpha-amino-beta-guanidino propionic acid), and all stereoisomers and salts thereof. Another embodiment of the invention utilizes the following subset of amino acids: glutamine, asparagine, lysine, ornithine, arginine, histidine, or citrulline, and all stereoisomers and salts thereof. Another embodiment of the invention utilizes the following subset of amino acids: D-glutamine or L-glutamine, and all salts thereof. In another embodiment, the amino acid is L-glutamine, and all salts thereof. In another embodiment of the invention, the amino acid is beta-alanine (3-amino propionic acid, $H_2NCH_2CH_2COOH$).

The terms "peptide," "polypeptide," "oligopeptide," and the like are used interchangeably herein to refer to any polymer of amino acid residues of any length. The peptide polymer can be linear or non-linear (e.g., branched), it can comprise modified amino acids or amino acid analogs, and it can be interrupted by chemical moieties other than amino acids. The terms also encompass an amino acid polymer that has been modified naturally or by intervention; for example, by disulfide bond formation, glycosylation, lipidation, acetylation, phosphorylation, or any other manipulation or modification, such as conjugation with a labeling or bioactive component.

By "conjugation" is meant the process of forming a covalent linkage, with or without an intervening linker, between two moieties, such as a polyamine analog and a amino acid moiety. The conjugation can be performed by any method known in the art, such as those described in Wong, *Chemistry of Protein Conjugation and Cross-linking,* 1991, CRC Press, Boca Raton, and described herein. Suitable methods include using strategies incorporating protecting groups such as the t-butyloxycarbonyl (BOC) protecting group (reagents for introducing the BOC group are available from Sigma, St. Louis, Mo., and other suppliers). Other suitable protecting groups which can be used in the conjugation reactions are described in Greene et al., *Protective Groups in Organic Synthesis,* 2nd Edition, 1991, Wiley, N.Y. By "conjugate" is meant a chemical entity comprising two moieties which are covalently linked.

An "amino-capping group" or "amino-terminal capping group" is a group that covalently links to an amino group. Examples of amino-capping groups include, but are not limited to, 4-morpholinocarbonyl, acetyl, and trifluoro-acetyl. An "amino-protecting group" or "amino-terminal protecting group" is a group that can be selectively removed from an amino group of a molecule without affecting the remainder of the molecule. Examples of amino-protecting groups include, but are not limited to, t-butyloxycarbonyl (BOC), 9-fluorenylmethoxycarbonyl (FMOC), benzyloxy-carbonyl (CBZ ), t-butyldimethylsilyl (TBDIMS), or suitable photolabile protecting groups such as 6-nitroveratry-loxy carbonyl (Nvoc) and the like.

An "exterior nitrogen" or "exterior amino group" of a polyamine or polyamine analog is a nitrogen (amino) group which is flanked by only one other nitrogen group, while an "interior nitrogen" or "interior amino group" of a polyamine or polyamine analog is a nitrogen (amino) group which is flanked by two other nitrogen (amino) groups. For example, in a polyamine analog of the formula

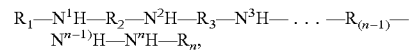

where n is an integer, the nitrogens designated as $N^1$ and $N''$ are the "exterior nitrogens" or "exterior amino groups," inasmuch as they are flanked by only one other nitrogen group, while $N^2$, $N^3$, etc., through $N^{(n-1)}$ are "interior nitrogens" or "interior amino groups," flanked by two other nitrogen (amino) groups.

An "individual" is a vertebrate, preferably a mammal, more preferably a human.

An "effective amount," "therapeutic amount," or "therapeutically effective amount" is an amount sufficient to effect beneficial or desired clinical results. An effective amount can be administered in one or more administrations. For purposes of this invention, an effective amount of a polyamine analog conjugate is an amount that is sufficient to cure, palliate, ameliorate, stabilize, reverse, slow or delay the progression of the disease state, or the symptoms of the disease state.

As used herein, "treatment" is an approach for obtaining beneficial or desired clinical results, including, but not limited to, the suppression of viral growth. For purposes of this invention, beneficial or desired clinical results include, but are not limited to, alleviation of symptoms, diminishment of extent of disease, stabilization (i.e., not worsening) of state of disease, prevention of spread (e.g., contagion) of disease, delay or slowing of disease progression, amelioration or palliation of the disease state, improvement in quality or enjoyment of life, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering polyamine analog conjugates of the present invention.

Polyamine Analogs Useful in the Invention

One embodiment of the present invention encompasses a polyamine analog conjugated to an amino acid. Other aspects of the invention encompass compositions comprising these conjugate(s). Non-limiting examples of polyamine analogs which can be used are described below.

Conformationally Restricted Polyamine Analogs

Polyamine analogs which can be used in the invention include any polyamine analog that has a pendant amino, hydroxyl, or thiol group which can be conjugated to the C-terminus of the amino acid moiety in an amide linkage, ester linkage or thioester linkage, respectively, and examples are provided in the summary of the invention, the definition of "polyamine analogs" and in the synthetic schemes. Polyamine analogs used in the present invention can be conformationally restricted.

Figure 10:
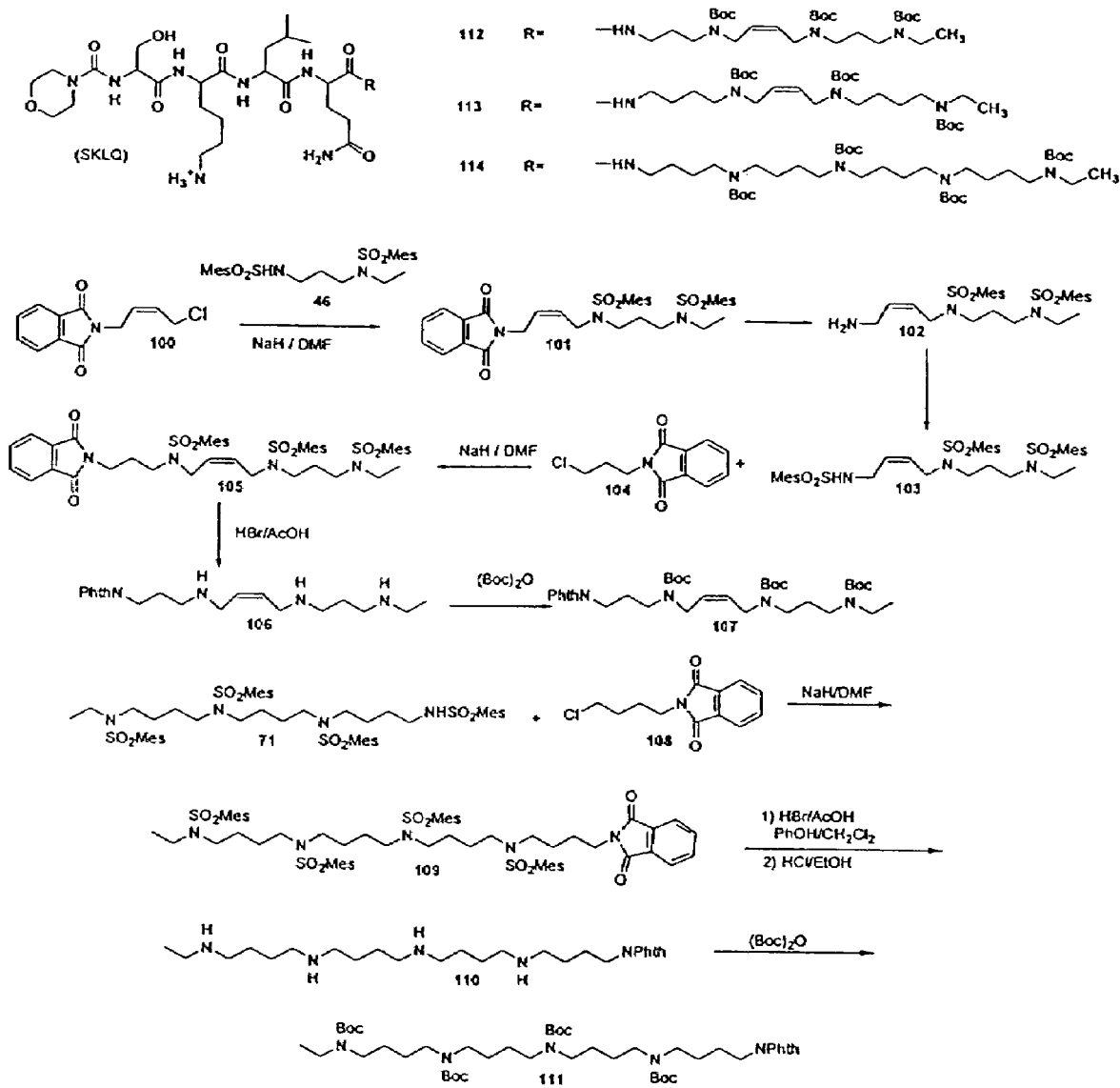
FIG. 10 depicts Scheme 26, illustrating the synthesis of an amino acid conjugated to various polyamine analogs via an amide linkage.

Schemes 1–25 (see FIGS. 1–10) depict syntheses of various polyamine analogs which can be used in the invention. Examples of polyamine analogs which can be used in the invention are also given in U.S. Pat. Nos. 5,889,061 and 5,627,215, which describe tetraamino polyamine analogs. The synthesis of the polyamine analogs of those patents can be modified to introduce an amino-protecting group on the exterior nitrogens (i.e., representing the tetraamine as $R_1$—$N^1H$—$R_2$—$N^2H$—$R_3$—$N^3H$—$R_4$—$N^4H$—$R_5$, the nitrogens designated as $N^1$ and $N^4$ "exterior" nitrogens, inasmuch as they are flanked by only one other nitrogen group, while $N^2$ and $N^3$ are "interior" nitrogens, flanked by two other nitrogen groups) in place of the group that would ordinarily be attached at that point (in this example, a protecting group would be used instead of $R_1$ or $R_5$), and can be cleaved to yield a primary amino group at one of the exterior nitrogens, while maintaining amino-protecting groups on the other exterior nitrogen and the interior nitrogens. Scheme 26 of FIG. 10 depicts such a strategy of establishing a protecting group regimen which allows one of the exterior amino groups to be selectively deprotected, while maintaining the amino-protecting groups on the other exterior amino group and the interior amino groups. Examples of differential protection regimens of polyamine or polyamine analogs are also given in Fiedler et al. (1993) *Helv. Chim. Acta* 76:1511–1519 and Iwata et al. (1989) *Bull. Chem. Soc. Japan* 62:1102–1106.

TABLE 1

| No. | Structure |
| --- | --- |
| SL-11027 | 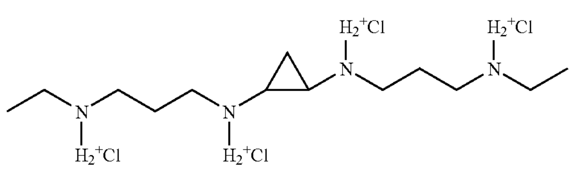 |
| SL-11028 | 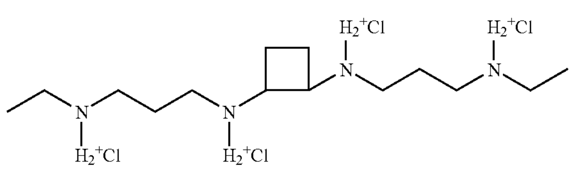 |
| SL-11029 | 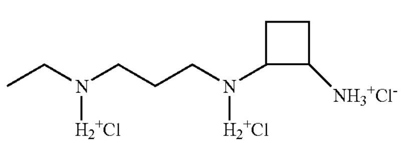 |

TABLE 1-continued

| No. | Structure |
|---|---|
| SL-11033 | Ethyl-NH-(CH$_2$)$_3$-NH-(cyclopropyl)-NH-(CH$_2$)$_3$-NH-Ethyl · 4HCl |
| SL-11034 | Ethyl-NH-(CH$_2$)$_3$-NH-(cyclobutyl)-NH-(CH$_2$)$_3$-NH-Ethyl · 4HCl |
| SL-11035 | Ethyl-NH-(CH$_2$)$_3$-NH-(CH$_2$)$_6$-NH-(CH$_2$)$_3$-NH-Ethyl · 4HCl |
| SL-11036 | H$_3$N$^+$Cl$^-$-(CH$_2$)$_3$-NH-(cyclopropyl)-NH-(CH$_2$)$_3$-NH$_3^+$Cl$^-$ · additional HCl |
| SL-11037 | Ethyl-NH-(CH$_2$)$_3$-NH-CH$_2$-(cyclopropyl)-CH$_2$-NH-(CH$_2$)$_3$-NH-Ethyl · 4HCl |
| SL-11038 | Ethyl-NH-(CH$_2$)$_3$-NH-CH$_2$-(cyclopropyl)-CH$_2$-NH-(CH$_2$)$_3$-NH-Ethyl · 4HCl |
| SL-11043 | Ethyl-NH-(CH$_2$)$_3$-NH-CH$_2$-(cyclobutyl)-CH$_2$-NH-(CH$_2$)$_3$-NH-Ethyl · 4HCl |
| SL-11044 | Ethyl-NH-(CH$_2$)$_3$-NH-CH$_2$-(cyclobutyl)-CH$_2$-NH-(CH$_2$)$_3$-NH-Ethyl · 4HCl |
| SL-11047 | Ethyl-NH-(CH$_2$)$_3$-NH-CH$_2$-CH=CH-CH$_2$-NH-(CH$_2$)$_3$-NH-Ethyl (cis) · 4HCl |
| SL-11048 | Ethyl-NH-(CH$_2$)$_3$-NH-CH$_2$-CH=CH-CH$_2$-NH-(CH$_2$)$_3$-NH-Ethyl (trans) · 4HCl |
| SL-11050 | BnNH(CH$_2$)$_4$NHBn.2HCl |
| SL-11061 | EtNH(CH$_2$)$_4$NH(CH$_2$)$_4$NH(CH$_2$)$_4$NH(CH$_2$)$_4$—NHEt.5HCl |
| SL-11090 | MeNH-(CH$_2$)$_3$-NH-CH$_2$-(trans-cyclobutyl)-CH$_2$-NH-(CH$_2$)$_3$-NHMe · 4HCl |
| SL-11091 | EtNH-(CH$_2$)$_3$-NH-CH$_2$-C≡C-CH$_2$-NH-(CH$_2$)$_3$-NHEt · 4HCl |

TABLE 1-continued
| No. | Structure |
|---|---|
| SL-11092 | 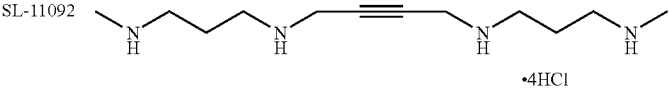 •4HCl |
| SL-11093 | 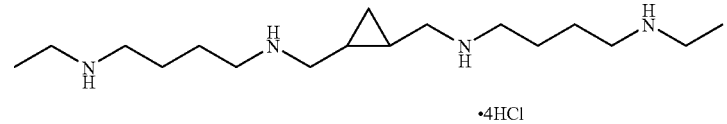 •4HCl |
| SL-11094 | 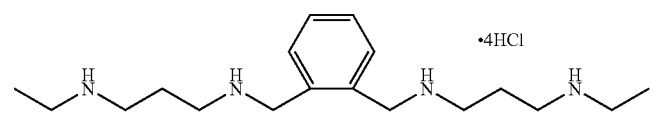 •4HCl |
| SL-11098 | 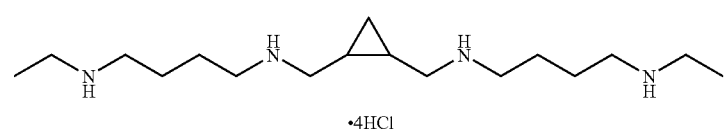 •4HCl |
| SL-11099 | 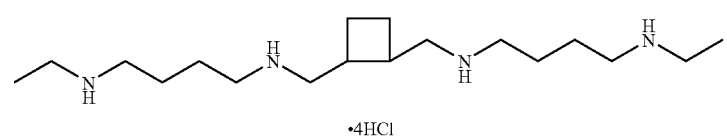 •4HCl |
| SL-11100 | 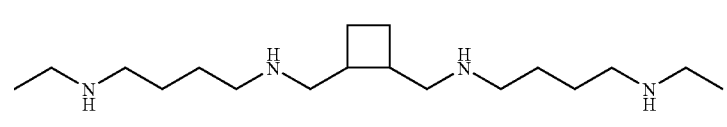 •4HCl |
| SL-11101 | 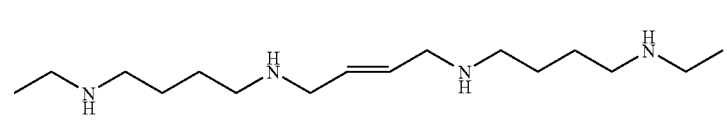 •4HCl |
| SL-11102 | 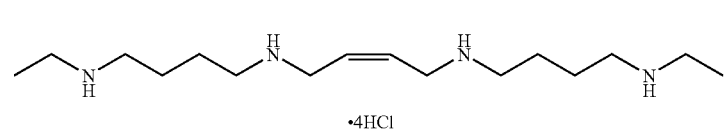 •4HCl |
| SL-11103 | 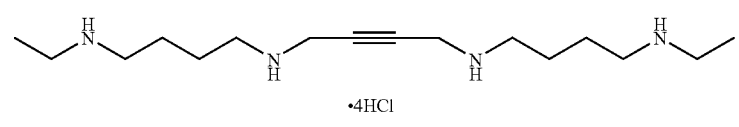 •4HCl |
| SL-11104 | 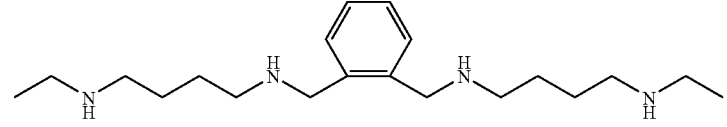 •4HCl |
| SL-11105 | 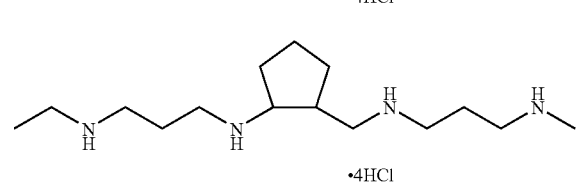 •4HCl |

TABLE 1-continued

| No. | Structure |
| --- | --- |
| SL-11108 | Chemical structure ·4HCl |
| SL-11114 | Chemical structure 4·HCl |
| SL-11118 | Chemical structure ·4HCl |
| SL-11119 | Chemical structure ·4HCl |
| SL-11121 | Chemical structure 5·HCl |
| SL-11122 | Chemical structure 5·HCl |
| SL-11123 | Chemical structure 5·HCl |
| SL-11124 | Chemical structure ·4HCl |
| SL-11126 | Chemical structure 5·HCl |
| SL-11127 | Chemical structure 5·HCl |
| SL-11128 | Chemical structure 5·HCl |
| SL-11129 | Chemical structure 5·HCl |

TABLE 1-continued
| No. | Structure |
| --- | --- |
| SL-11130 | 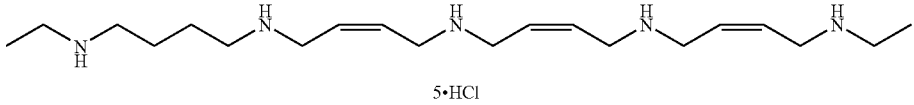 5·HCl |
| SL-11132 | 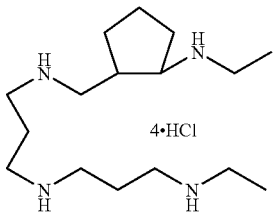 4·HCl |
| SL-11133 | 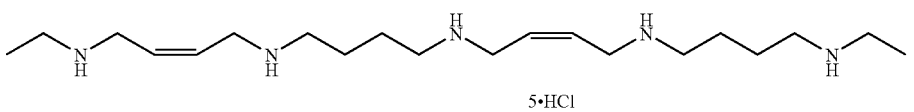 5·HCl |
| SL-11134 | 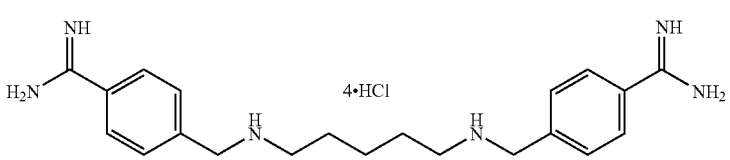 4·HCl |
| SL-11135 | 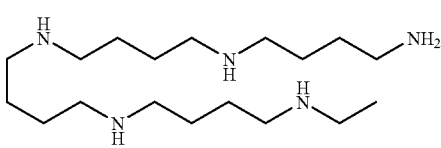 5·HCl |
| SL-11136 | 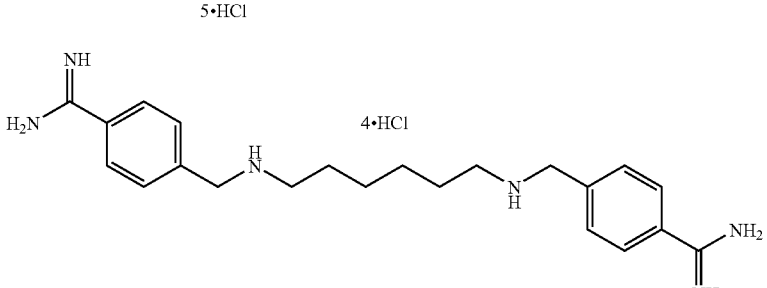 4·HCl |
| SL-11137 | 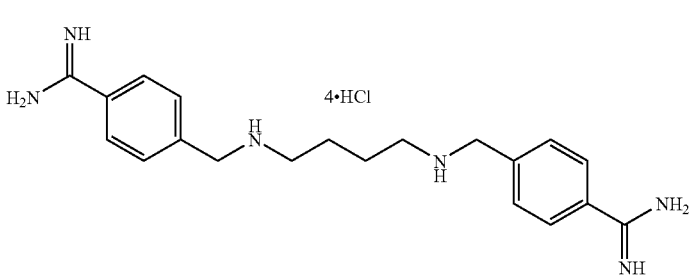 4·HCl |
| SL-11141 | 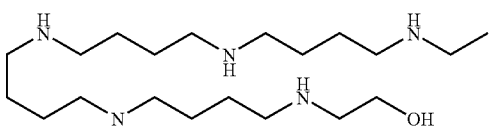 5·HCl |

TABLE 1-continued

| No. | Structure |
|---|---|
| SL-11143 | (structure) 5·HCl |
| SL-11144 | (structure) 10·HCl |
| SL-11150 | (structure) 10·HCl |
| SL-11155 | (structure with O-Gln-Leu, NHEt) 6·HCl |
| SL-11157 | 8·HCl (structure) |
| SL-11158 | 8·HCl (structure) |
| SL-11159 | (structure) 10·HCl |
| SL-11160 | (structure) 8·HCl |

Conjugation of Polyamine Analogs to the Amino Acid Moiety

Any method known in the art can be used to conjugate (i.e., link) the amino acid to the polyamine analog, including, but not limited to, those disclosed herein. Suitable methods include using strategies incorporating protecting groups such as the t-butyloxycarbonyl (BOC) protecting group (reagents for introducing the BOC group are available from Sigma, St. Louis, Mo., and other suppliers). Other suitable protecting groups which can be used in the conjugation reactions are described in Greene et al., *Protective Groups in Organic Synthesis* 2nd Edition, 1991, Wiley, New York. Coupling chemistry is described in Bodanszky, M. and Bodanszky, A., *The Practice of Peptide Synthesis*, New York: Springer-Verlag, 1984; Bodanszky, M., *Principles of Peptide Synthesis*, 2nd Edition, New York: Springer-Verlag, 1993; Bodanszky, M., *Peptide Chemistry: A Practical Textbook*, 2nd Edition, New York: Springer Verlag, 1993; *Fmoc Solid Phase Peptide Synthesis : A Practical Approach* (Practical Approach Series) (Weng Chan and Peter D. White, Eds.) (Oxford University Press, 2000), and *Solid Phase Peptide Synthesis* (John M. Stewart and Janis D. Young; Pierce Chemical Co., Rockford Ill., 1984). When alpha-amino acids are used, the amino acids are preferentially coupled via the alpha-COOH group of the C-terminal amino acid, although other linkages are possible, depending on the amino acid (e.g., the gamma-carboxyl group of a glutamic acid residue can be used for linkage). When amino acids other than alpha-amino acids are used, if only one carboxyl group is present, the linkage is preferably to that carboxylic acid group of the amino acid; when more than one carboxylic acid group is present in a non-alpha-amino acid, any available carboxylic acid group can be used for the coupling. When a polyamine or polyamine analog is coupled, the linkage will be via an amino group of the polyamine (i.e., an amide linkage); when a polyamine analog alcohol is conjugated, the linkage can be via either an amino group or a hydroxy group of the polyamine analog alcohol (i.e., an amide linkage or ester linkage, respectively). The amino acid is preferably coupled to an exterior nitrogen. When an ester linkage to a polyamine analog is used, the amino acid is preferably coupled to a terminal hydroxy group.

Therapeutic Use of Polyamine- and Polyamine Analog-amino Acid Conjugates

Polyamine- and polyamine analog-amino acid conjugates of the present invention are useful for treatment of a variety of diseases caused by uncontrolled proliferation of cells, including cancer, particularly prostate cancer and other cancers. The conjugates are used to treat mammals, preferably humans.

In order to evaluate the efficacy of a particular polyamine- or polyamine analog-amino acid conjugate for a particular medicinal application, the compounds can be first tested against appropriately chosen test cells in vitro. In a non-limiting example, the conjugates can be tested against tumor cells, for example, prostate tumor cells. Exemplary experiments can utilize cell lines capable of growing in culture as well as in vivo in athymic nude mice, such as LNCaP. Horoszewicz et al. (1983) *Cancer Res.* 43:1809–1818. Culturing and treatment of carcinoma cell lines, cell cycle and cell death determinations based on flow cytometry; enzyme assays including ODC, SAMDC and SSAT activities; and high pressure liquid chromatography detection and quantitation of natural polyamines and polyamine analogs are described in the art, for example, Mi et al. (1998) *Prostate* 34:51–60; Kramer et al. (1997) *Cancer Res.* 57:5521–27; and Kramer et al. (1995) *J. Biol. Chem.* 270:2124–2132. Evaluations can also be made of the effects of the conjugates on cell growth and metabolism.

Analysis begins with $IC_{50}$ determinations based on dose-response curves ranging from 0.1 to 1000 µM performed at 72 hr. From these studies, conditions can be defined which produce about 50% growth inhibition and used to: (a) follow time-dependence of growth inhibition for up to 6 days, with particular attention to decreases in cell number, which may indicate drug-induced cell death; (b) characterize conjugate effects on cell cycle progression and cell death using flow cytometry (analysis to be performed on attached and detached cells); (c) examine conjugate effects on cellular metabolic parameters. Polyamine- and polyamine analog-amino acid conjugate effects can be normalized to intracellular concentrations (by HPLC analysis), which also provide an indication of their relative ability to penetrate cells. Marked differences in conjugate uptake can be further characterized by studying conjugate ability to utilize and regulate the polyamine transporter, as assessed by competition studies using radiolabeled spermidine, as previously described in Mi et al. (1998). Polyamine- and polyamine analog-amino acid conjugates could also enter the cells by a diffusion mechanism.

In Vivo Testing of Polyamine- and Polyamine Analog-amino Acid Conjugates

Polyamine- and polyamine analog-amino acid conjugates found to have potent anti-proliferative activity in vitro towards cultured carcinoma cells can be evaluated in in vivo model systems. The first goal is to determine the relative toxicity of the conjugates in non-tumor-bearing animals, such as DBA/2 mice. Groups of three animals each can be injected intraperitoneally with increasing concentrations of a conjugate, beginning at, for example, 10 mg/kg. Toxicity as indicated by morbidity is closely monitored over the first 24 hr. A well-characterized polyamine analog, such as BE-333, can be used as an internal standard in these studies, since a data base has already been established regarding acute toxicity via a single dose treatment relative to chronic toxicity via a daily ×5 d schedule. Thus, in the case of new compounds, single dose toxicity relative to BE-333 is used to project the range of doses to be used on a daily ×5 d schedule.

After the highest tolerated dosage on a daily ×5 d schedule is deduced, antitumor activity is determined. Typically, tumors can be subcutaneously implanted into nude athymic mice by trocar and allowed to reach 100–200 $mm^3$ before initiating treatment by intraperitoneal injection daily ×5 d. Most conjugates can be given in a range between 10 and 200 mg/kg. Conjugates can be evaluated at three treatment dosages with 10–15 animals per group (a minimum of three from each can be used for pharmacodynamic studies, described below). Mice can be monitored and weighed twice weekly to determine tumor size and toxicity. Tumor size is determined by multi-directional measurement from which volume in $mm^3$ is calculated. Tumors can be followed until median tumor volume of each group reaches 1500 $mm^3$ (i.e., 20% of body weight), at which time the animals can be sacrificed. Although the initial anti-tumor studies focuses on a daily ×5 d schedule, constant infusion can be performed via Alzet pump delivery for 5 days since this schedule dramatically improves the anti-tumor activity of BE-333 against A549 human large cell lung carcinoma. Sharma et al. (1997) *Clin. Cancer Res.* 3:1239–1244. In addition to assessing anti-tumor activity, free conjugate levels in tumor and normal tissues can be determined in test animals.

Methods of Administration of Polyamine- and Polyamine Analog-amino Acid Conjugates The polyamine- and polyamine analog-amino acid conjugates of the present invention can be administered to a mammalian, preferably human, subject via any route known in the art, including, but not limited to, those disclosed herein. Preferably administration of the conjugates is intravenous. Other methods of administration include but are not limited to, oral, intrarterial, intratumoral, intramuscular, topical, inhalation, subcutaneous, intraperitoneal, gastrointestinal, and directly to a specific or affected organ. The novel polyamine analogs described herein are administratable in the form of tablets, pills, powder mixtures, capsules, granules, injectables, creams, solutions, suppositories, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the conjugates to retain its pharmacological activity in the body. Formulations for parenteral and nonparenteral drug delivery are known in the art and are set forth in *Remington's Pharmaceutical Sciences,* 18th Edition, Mack Publishing (1990). Solid forms, such as tablets, capsules and powders, can be fabricated using conventional tableting and capsule-filling machinery, which is well known in the art. Solid dosage forms, including tablets and capsules for oral administration in unit dose presentation form, can contain any number of additional non-active ingredients known to the art, including such conventional additives as excipients; dessicants; colorants; binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets can be coated according to methods well known in standard pharmaceutical practice. Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, conjugates can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers. The pharmaceutical unit dosage chosen is preferably fabricated and administered to provide a final concentration of drug at the point of contact with the cancer cell of from 1 µM to 10 mM, from 1 µM to 1 mM, from 1 µM to 100 µM, from 1 µM to 10 µM, from 1 nM to 1 µM, from 1 nM to 100 nM, or from 1 nM to 10 nM. The optimal effective concentration of polyamine- and polyamine-amino acid conjugates can be determined empirically and will depend on the type and severity of the disease, route of administration, disease progression and health and mass or body area of the patient. Such determinations are within the skill of one in the art. Polyamine- and polyamine-amino acid conjugates can be administered as the sole active ingredient, or can be administered in combination with another active ingredient, including, but not limited to, cytotoxic agents, antibiotics, antimetabolites, nitrosourea, vinca alkaloids, polypeptides, antibodies, cytokines, etc.

The following examples are provided to illustrate, but not limit, the invention.

EXAMPLES

Synthesis Of Conformationally-restricted Polyamine Analogs a) Spermine and Homospermine Analogs Containing a Conformational Restriction Scheme 2 exemplifies a $N^\alpha$, $N^\omega$-bisethyl homospermine analog 7 containing a central trans-unsaturated bond. Amide 4 was prepared as described in Scheme 1 by alkylation of amide 1 with bromobutyronitrile to give 2, followed by reduction of the nitrile to the amine 3 that was mesitylsulfonated to 4. Trans-allylic diester 5 was used to alkylate amide 4 and the tetramide 6 was obtained. Deprotection gave the trans-tetramide 7 (Scheme 2). Introduction of a triple bond in the butane segment of homospermine also reduces its mobility. This was achieved by starting with the butyne diester 8 and following the sequence of reactions outlined above (Scheme 3). Schemes 15–20 are further examples of the synthesis of polyamine spermine and homospermine analogs of this type.

b) Synthesis Of Pentamines with Conformational Restrictions.

Schemes 4–14 are outlines of the syntheses of conformationally restricted pentamines. Scheme 4 depicts the reaction of cis-1-chloro-4-phthalimido butene with amide 1 to give 11. Hydrazinolysis of 11 gave 12 which was amidated to 13. Reaction of the latter with 1,4-diiodobutane gave 14, while reaction with equimolar amounts of cis-1,4-dichlorobutene gave 15.

Amide 4 was alkylated with either 4-chlorobutyronitrile to give 16 or with cis-1,4-dichlorobutene to give 19. Nitrile 16 was reduced with hydrogen over Ni Raney to the amine 17 and the latter transformed in to the amide 18 (Scheme 5). Condensation of 18 with the chloroalkyl intermediate 15 gave the pentamaide 20 that was deprotected to the pentamine 21 (Scheme 6). Condensation of 18 with the iodoalkyl derivative 14 gave 22 that was deprotected to the pentamine 23 (Scheme 7). Condensation of 18 and 19 gave pentamide 24 that was deprotected to the pentamine 25 (Scheme 8). Using 14 as the alkylating agent, mesitylenesulfonamide was dialkylated to give 26, and the latter deprotected to give 27 (Scheme 9). The analogous reaction carried out using 15 as alkylating agent, gave 28 and after deprotection led to the pentamine 29 (Scheme 10).

Alkylation of mesitylenesulfonamide with 19 gave the pentamide 30, which was deprotected to 31 (Scheme 11). When 19 was used to alkylate an equimolar amount of mesitylenesulfonamide then 32 was obtained. Alkylation of 32 with 14 gave 33, that was deprotected to give 34 (Scheme 12). When the chloroalkyl intermediate 15 was used to alkylate one equivalent of mesitylenesulfonamide, then the triamide 35 was obtained. Reaction of 35 with 14 gave 36 which was then deprotected to 37 (Scheme 13). Condensation of 35 and 19 gave the pentamide 38 that was deprotected to 39 (Scheme 14). The above mentioned Schemes describe the synthesis of cis-compounds. The same synthetic methodology can be used to obtain the trans-isomers, or cis and traits bonds in different segments within the same molecule.

c) Polyamine Analog with Diamidine Substituents.

A new class of polyamine analogs is shown in Scheme 21. They derive from 1,4-dibenzylputrescine, 1,5-dibenzylcadaverine, and 1,6-dibenzylhexanediamine. They are diamidine derivatives, where the diamidine residues are carrier groups that have been shown to be efficient in the transport of drugs into different protozoa. The general procedure of synthesis was based on the condensation of 4-cyanobenzaldehyde with the diaminoalkanes to give the Schiff bases, followed by reduction in situ to the corresponding dinitriles 68. The latter were converted to the diamidines 69 through their iminoethers.

d) Synthesis of Oligoamines.

Scheme 22 describes the synthesis of a N-2 hydroxyethyl derivative of a pentamine such as 75. Starting with 18, alkylation with 4-bromobutyronitrile gave 70. Reduction of the nitrile of 70 and mesitylenesulfonylation of the resulting amino group gave 71. It was alkylated again with 4-bromobutyronitrile to give 72, and again reduced and mesitylsulfonylated to give 73. The latter was then alkylated with the benzyl ester of 2-bromoethanol to give 74. Treatment with hydrobromic acid in acetic acid cleaved both the mesitylene sulfonyl protecting groups and the benzyl ether residue to give 75.

Scheme 23 reports the synthesis of a trans-decamine 77 and of a cis-decamine 79. Starting with the pentamide 73 (Scheme 22) and by reaction with trans-diester 5 (Scheme 2) the decamide 76 was prepared, which on deprotection gave 77 as a decahydrochloride. In an analogous manner, by condensation of 73 with the cis-1,4-dimesityleneoxy-2-butene, the decamide 78 was prepared, which on deprotection gave 79 as a decahydrochloride.

Scheme 24 outlines the synthesis of a N-2 hydroxyethyl trans-decamine 92 and a cis-2-hydroxyethyl decamine 95. The procedure repeats almost all the procedures described in the foregoing schemes. The synthesis of 80 proceeded by alkylating BOC-mesitylenesulfonamide with the benzyl ester of 2-bromoethanol. Cleavage of the BOC protecting group leads to 81, alkylation with 4-bromobutyronitrile then gave 82, and after reduction of the nitrile group and reaction with mesitylene sulfonyl chloride the diamide 83 was obtained. Again, alkylation with 4-bromobutyronitrile led to 84, reduction and mesitylsulfonylation gave 85, alkylation of 85 gave 86, reduction and mesitylsulfonylation gave 87, and alkylation, reduction and mesitylsulfonylation performed on 87 gave 89. Alkylation of 73 with trans-1,4-dibromo-2-butene gave 90. Alkylation of 89 with 90 gave 91, which after deprotection gave the trans-ω-hydroxydecamine 92. Alkylation of 73 with cis-1,4-dichloro-2-butene gave 93. Alkylation of 89 with 93 gave 94. Deprotection of 94 gave the cis-ω-hydroxy-decamine 95, isomeric with 92.

e) Synthesis of oligoamine-amino acid conjugate 97.

Scheme 25 outlines the synthesis of an amino acid derivative of 75 (SL-11141). Starting with 74, hydrogenolysis leads to 96, that is then is then esterified with N-BOC-glutamine to 97.

(f) Synthesis of polyamine analog conjugates of amino acids

Scheme 26 outlines the synthesis of polyamine analog conjugates of the polyamine analogs corresponding to SL-11047, SL-11101, or BE4-4-4-4 to give the conjugates 112, 113, and 114. The polyamine analog intermediates are constructed as follows. Chloride 100 is condensed with 46 to give 101. The phthalimido group is cleaved by hydrazynolysis to give 102, and the latter is mesitylated to 103 This amide is again alkylated with 104 to give 105. The mesitylene sulfonyl groups of 105 are then cleaved and 106 is obtained. It is protected using (BOC)$_2$O, and the resulting 102 is deprotected by hydrazynolysis to give the polyamine analog moiety of 112. In tandem, the known 74 (Scheme 17) was alkylated with 108 to give 109. Cleavage of the mesitylenesulfonyl groups gave 110. The free amino groups were reprotected with (BOC)$_2$O to give 111. Cleavage of the phthalimido residue via hydrazinolysis using a procedure analogous to that for compound 12 below gave the aminopolyamine analog intermediate for the synthesis of 114.

In one embodiment, both exterior nitrogens of the polyamine analog-amino acid conjugates have an ethyl group as one of their substituents. In the synthesis outlined above, one exterior nitrogen already bears an ethyl group; the synthesis can be readily modified to add an ethyl group to the other exterior nitrogen. For example, the phthalimido group on the intermediate 111 in Scheme 26 is removed using hydrazinolysis using a procedure analogous to that for compound 12 below to yield CH$_3$CH$_2$N(Boc)[(CH$_2$)$_4$N(Boc)]$_3$(CH$_2$)$_4$NH$_2$. This primary amine containing compound is then reacted with an ethyl halide (e.g., ethyl bromide, ethyl iodide, ethyl chloride) or another reactive ethylation agent, e.g., ethyl mesylate. The alkylating reagent is generally added dropwise or in small portions to an excess of the primary amine to avoid further alkylation of the desired product, CH$_3$CH$_2$N(Boc)[(CH$_2$)$_4$N(Boc)]$_3$(CH$_2$)$_4$NHCH$_2$CH$_3$. This product is then reacted with an amino acid, e.g., Nα-Boc-glutamine, Nα-Boc-asparagine, N-α,ε-Boc-lysine, or other desired amino acid, suitably protected to react at its α-carboxylic acid functionality (or, if desired, at the side chain acid functionality of glutamic acid and aspartic acid). Dicyclohexylcarbodiimide, diisopropylcarbodiimide, HBTU, HATU, or other coupling reagents and protocols well-known in the art can be used to couple the amino acid to the polyamine analog. The progress of the reaction can be monitored by HPLC or other methods.

Coupling of amino acids to any or all other amino groups of a polyamine or polyamine analog can be carried out by using appropriately protected subunits during synthesis. The general scheme involves using protecting groups which can be removed independently of each other; methods of differentially protecting compounds are shown in, e.g., Scheme 26.

EXAMPLES

Example 1

Synthesis Of Polyamine Analog Compounds

Compound 2: NaH (80%, 1.08 g, 36 mmol) was added to a solution of amide 1 (6.81 g, 30 mmol) in DMF (50 ml) in an ice-water bath under N$_2$. The mixture was stirred for 1 h and a solution of 4-bromobutyronitrile (4.88 g, 33 mmol) in DMF (10 ml) was added in portions. The mixture was stirred over night at 75° C. The solvent was distilled off, the residue taken up in chloroform washed with a saturated solution of ammonium chloride, dried (Na$_2$SO$_4$) and evaporated. The residue was purifid by flash chromatography on silica gel (hexane/ethyl acetate 3:1) to yield 8.0 g (90%) of 2 as a colorless oil. $^1$H-NMR (CDCl$_3$) δ 1.05 (t, 3H), 1.90 (m, 2H), 2.30 (b, m, 5H), 2.60 (s, 6H), 3.20 (q, 2H), 3.35 (t, 2H), 6.95 (s, 2H); $^{13}$C-NMR (CDCl$_3$): δ 12.50, 20.61, 22.43, 23.60, 31.05, 36.12, 40.39, 43.78, 118.62, 131.79, 132.67, 139.71, 142.41. MS-EI (m/z) 294 (M$^+$).

Compound 4: Nitrile 2 (7.8 g, 27 mmol) was dissolved in a mixture of ethanol (150 ml) and concentrated hydrochloric acid (1.5 ml). PtO$_2$ was added (700 mg) and the mixture was hydrogenated at 50 psi over night. The catalyst was filtered off and the solvent evaporated. The residue (78 g, 98%) was used in the next step without further purification. The free base gave $^1$H-NMR (CDCl$_{13}$) δ 1.00 (t, 3H), 1.55 (m, 4H), 2.25 (s, 3H), 2.80 (t, 2H), 3.20 (m, 4H), 6.95 (s, 2H); $^{13}$C-NMR (CDCl$_3$): δ 12.54, 20.69, 22.53, 24.72, 27.65, 39.92, 40.29, 44.59, 131.71, 133.21, 139.82, 142.09. FAB-MS (m/z) 299 (M$^+$+1). Mesitylenesulfonyl chloride (8.8 g, 40.5 mmol) in dioxane (30 ml) was added dropwise to a stirred mixture of compound 3 (7.8 g, 27 mmol) dissolved in dioxane (60 ml) and 50% KOH (30 ml) at 0° C. The reaction mixture was allowed to reach 20° C. and then kept over night. An excess of water was added and the mixture was extracted with chloroform, dried (Na$_2$SO$_4$) and evaporated. The oily residue was crystallized from ethyl acetate/hexane yielding 4; 10.9 g (82%); mp 71.5–72° C. $^1$H-NMR (CDC$_{13}$) δ 1.00 (t, 3H), 1.10–1.50 (m, 4H), 2.30 (s, 6H), 2.55, 260 (s, 12H), 2.85 (q, 2H), 3.15 (m, 4H), 4.70 (t, 1H), 6.95, 7.00 (s, 4H); $^{13}$C-NMR (CDCl$_3$): δ 12.70, 20.92, 21.04, 22.73, 22.92, 24.58, 26.68, 40.04, 42.02, 44.42, 131.91, 133.31, 133.64, 138.99, 140.05, 142.15, 142.35. MS-FAB (m/z) 480 (M$^+$).

(E)-2-Butene-1,4-diyl bis[mesitylenesulfonate](5): (E)-2-Butene-1,4-diol (1.76 g, 20 mmol), and benzyltriethylammonium bromide (270 mg, 1 mmol) were dissolved in 30 ml of a 50% potassium hydroxide solution and 30 ml of dioxane. The mixture was stirred at 5° C. and mesitylenesulfonyl chloride (8.72 g, 40 mmol) dissolved in 30 ml of dioxane was added dropwise. When the addition was over, stirring was continued for 1 h, water was then added, and the white precipitate was filtered and crystallized from chloroform-hexane to yield 5; 7.0 g (77%); mp 119–120° C. $^1$H-NMR (CDCl$^3$): δ 2.35 (s, 6H), 2.60 (s, 12H), 4.45 (d, 4H), 5.75 (b, 2H), 6.95 (s, 4H); $^{13}$C-NMR (CDCl$_3$): δ 20.96, 22.52, 67.96, 127.67, 131.69, 131.74, 139.79, 143.45. MS-EI (m/z), 452 (M$^+$), 253, 200, 183. Anal. Calcd for C$_{22}$H$_{28}$O$_6$S$_2$: C, 58.40; H, 6.19. Found: C, 58.35; H, 6.22.

Compound 6 was synthesized from 5 according to a procedure described elsewhere (Reddy et al., *J. Med. Chem.* 41:4723 (1998)) in 56% yield. $^1$-NMR (CDCl$_3$): δ 0.95 (t, J=7.15 Hz, 6H, CH$_3$), 1.34 (m, 8H, CH$_2$), 2.29 (s, 12H, CH$_3$), 2.55 (s, 24H, CH$_3$), 3.09 (m, 12H, NCH$_2$), 3.72 (d, J=4.53 Hz, 4H, NCH$_2$), 5.48 (t, J=4.31 Hz, 2H, CH=CH), 6.92 (s, 4H, Ph), 6.93 (s, 4H, Ph); $^{13}$C-NMR (CDCl$_3$): δ 12.71, 20.90, 22.71, 22.76, 24.74, 40.04, 42.21, 44.56, 45.69, 128.45, 131.88, 132.02, 140.05, 140.16, 142.20, 142.58. MS-FAB (m/z) 1012.8 (M$^+$, 100%), 828.7, 646.7, 561, 176.

Compound 7 was obtained from 6 as described elsewhere (Reddy et al., *J. Med. Chem.* 41:4723 (1998)) in 75% yield, mp>230° C. $^1$H-NMR (D$_2$O): δ 1.26 (t, J=12.5 Hz, 6H, 2CH$_3$), 1.79 (m, 8H, CH$_2$), 3.12 (m, 12H, NCH$_2$), 3.80 (d, J=7.16, 4H, NCH$_2$), 6.10 (m, 2H, CH=CH); $^{13}$C-NMR (D$_2$O): δ 12.79, 25.10, 45.19, 48.53, 48.62, 50.36, 130.66. MS-MALDI (m/z): 285.3 (MH$^+$, 100%).

Compound 8 was obtained from the commercially available butyne diol. Mesitylenesulfonyl chloride (19.5 g, 90 mmol) in dioxane (30 ml) was added dropwise to a stirred and cooled mixture of butyne diol (2.58 g, 30 mmol), 50% potassium hydroxide (30 ml) and triethylbenzyne ammonium bromide (405 mg, 1.5 mmol). Once the addition was over, the mixture was stirred at room temperature for an additional 3 h. An excess of water was added and the white precipitate was cooled over night, filtered off and dried. Recrystallization from ethyl acetate/hexane afforded 8.6 g (63%) of 8; mp 105–106° C. $^1$H-NMR (CDCl$_3$): δ 2.30 (s, 6H), 2.60 (s, 12H), 4.50 (s, 4H), 6.95 (s, 4H); $^{13}$C-NMR (CDCl3): δ 20.93, 22.48, 56.13, 80.41, 130.65, 131.67, 139.98, 143.67. MS-EI (m/z) 450 (M$^+$).

Compound 9 was obtained following a procedure analogous to that described for compound 42 (see below). From 450 mg (1 mmol) of diester 8 and 1.05 g (2.2 mmol) of diamide 4, 570 mg (56%) of tetramide 9 was obtained. $^1$H-NMR (CDCl$_3$): δ 0.90 (t, 6H); 1.30 (bs, 8H), 2.20 (s, 12H), 2.45 (s, 24H), 3.05 (m, 12H), 3.75 (s, 4H), 6.87 (s, 8H); $^{13}$C-NMR (CDCl$_3$): δ 12.70, 20.78, 22.68, 34.65, 39.97, 44.46, 44.99, 78.62, 131.85, 131.98, 132.34, 140.14, 142.13, 142.55. MS-FAB (m/z) 1010 (M$^⊕$).

Compound 10 was obtained following a procedure analogous to that described for compound 43 (see below). From 500 mg (0.49 mmol) of tetramide 9, 160 mg (76%) of the tetrahydrochloride 25 was obtained; mp>280° C. (decomp). $^1$H-NMR (D$_2$O): δ 1.30 (t, 6H), 1.80 (b, 8H), 2.90–3.25 (m, 12H), 4.05 (s, 4H); $^{13}$C-NMR (D$_2$O): δ 13.39, 25.64, 39.26, 45.72, 49.00, 49.20, 81.20. MS-MALDI 283 (M$^+$+1).

Compound 11: Mesitylenesulfonylethylamide 1 (3.1 g, 13.65 mmol) was dissolved in anhydrous DMF (30 ml) followed by the addition of NaH (85%, 0.423 g) in several portions. The mixture was stirred at room temperature for 1 h. N-(4-chloro-2-butenyl)-phthalimide (Aldrich, 3.06 g, 13 mmol) in 20 ml of DMF was added to the flask followed by stirring at 80° C. over night. The mixture was cooled to room temperature, quenched with H$_2$O (10 ml), and the solution was evaporated to dryness in vacuo. The solid residue was partitioned between 25 ml H$_2$O and 25 CHCl$_3$. The aqueous layer was extracted with CHCl$_3$ (3×25 ml), the organic layers were washed with brine (35 ml), dried (MgSO$_4$), the solvent was evaporated to afford a gum which solidified upon trituration with hexane to give 11. The $^1$H-NMR and $^{13}$C-NMR spectra showed that 11 was pure enough to be used in the next step without further purification, yield 4.75 g. $^1$H-NMR (CDCl$_3$): δ 1.16 (t, J=7.11 Hz, 3H, CH$_3$), 2.29 (s, 3H, CH$_3$), 2.63 (s, 6H, 2CH$_3$), 3.29 (q, J=7.11 Hz, 2H, CH$_2$), 4.06 (d, J=5.24 Hz, 2H, NCH$_2$), 4.26 (d, J=5.72 Hz, 2H, NCH$_2$), 5.59 (m, 2H, CH=CH), 6.95 (s, 2H, Ph), 7.71 (m, 2H, Ph), 7.83 (m, 2H, Ph); $^{13}$C-NMR (CDCl$_3$): δ 13.06, 20.89, 22.72, 34.35, 40.68, 42.01, 123.27, 126.69, 129.47, 131.90, 134.00, 140.24.

Compound 12: Amide 11 (20 g, 46.95 mmol) was dissolved in methanol, hydrazine monohydrate (5 ml, 98.52 mmol) was added and the solution stirred at 55° C. for 24 h. Initially it was a homogeneous solution; however, after several hours a white solid precipitated. The mixture was cooled to room temperature, 300 ml of conc. HCl were added slowly (exothermic reaction), and stirring at room temperature was continued for 12 h more. Methanol was evaporated, and the resulting solid was extracted with CHCl$_3$ (3×150 ml). The aqueous layer was neutralized with 50% NaOH, extracted again with CHCl$_3$ (3×100 ml), the combined organic layers were dried (MgSO$_4$); the solution was evaporated to afford a gum, which solidified under high vacuum to give 12; yield 9.0 g (65%). The compound was purified by column chromatography using hexane, ethyl acetate (7:3) as eluent; mp 167–169° C. $^1$H-NMR (CDCl$_3$): δ 1.0 (t, J=7.1 Hz, 3H, CH$_3$), 2.28 (s, 3H, CH$_3$), 2.56 (s, 6H, 2CH$_3$), 2.62 (br, NH$_2$), 3.12 (q, J=7.1 Hz, 2H, NCH$_2$), 3.73 (br, 2H, NCH$_2$), 3.94 (d, J=6.0 Hz, 2H, NCH$_2$), 5.80 (m, 2H, CH=CH), 6.92 (s, 2H, Ph); $^{13}$C-NMR (CDCl$_3$): δ 12.97, 20.93, 22.74, 36.43, 40.94, 42.08, 124.29, 131.89, 132.00, 132.62, 140.21, 142.67.

Compound 13 was obtained from 12 as described for 4 in 96% yield. It was purified 15 by column chromatography using hexane and ethyl acetate (4:1.5) as eluants; mp 98–99°

C.; ¹H-NMR (CDCl₃): δ 0.93 (t, J=5.85 Hz, 3H, CH₃), 2.23 (s, 3H, CH₃), 2.24 (s 3H, CH₃), 2.50 (s, 6H, 2CH₃), 2.56 (s, 6H, 2CH₃), 3.06 (q, J=7.15 Hz, 2H, NCH₂), 3.48 (t, J=5.99 Hz, 2H, NCH₂), 3.68 (d, J=5.72 Hz, 2H, NCH₂), 4.58 (t, J=6.24 Hz, 1H, NH), 5.44 (m, 2H, CH=CH), 6.87 (s, 2H, Ph), 6.89 (s, 2H, Ph); ¹³C-NMR (CDCl₃): δ 12.80, 20.89, 22.64, 22.89, 39.01, 40.59, 41.41, 128.14, 128.46, 131.91, 131.96, 139.08, 140.19, 142.26, 142.54. MS-FAB (m/z) 479.2 (M⁺, 65%), 296.2, 279.1, 267.2, 183.1.

Compound 15: Amide 13 (4.79 g, 10 mmol) was dissolved in anhydrous DMF (40 ml) followed by addition of NaH (0.37 g) in several portions, the mixture stirred at room temperature for 2 h, cis-1,4dichloro-2-butene (7.5 g, 60 mmol) in 10 ml DMF was added at once, and stirring was continued at 50° C. over night. The mixture was cooled to room temperature, quenched with 10 ml H₂O, the solvents were evaporated, and the contents were partitioned between H₂O (50 ml) and CHCl₃ (50 ml). The aqueous layer was extracted with CHCl₃ (3×50 ml), the pooled organic layers were dried (MgSO₄), evaporated, and 15 was purified by column chromatography using hexane, ethyl acetate (8.5: 1.5) as eluants; yield 5.5 g (97%), mp 106–108° C. ¹H-NMR (CDCl₃): δ 1.03 (t, J=7.33 Hz, 3H, CH₃), 2.30 (s, 6H, 2CH₃), 2.57 (s, 12H, 4CH₃), 3.17 (q, J=7.31 Hz, NCH₂), 3.71 (m, 4H, NCH₂), 3.81 (d, J=6.87 Hz, 2H, NCH₂), 3.95 (d, J=7.70 Hz, 2H, CHCl₂), 5.50 (m, 3H, CH=CH), 5.74 (m, 1H, CH=CH), 6.93 (s, 2H, Ph), 6.95 (s, 2H, Ph); ¹³C-NMR (CDCl₃): δ 12.91, 22.70, 22.74, 38.20, 40.45, 41.60, 42.11, 42.33, 128.17, 128.95, 129.34, 129.40, 131.94, 132.08, 140.23, 140.34, 142.91. MS-FAB (m/z) 566.7 (M⁺, 100%), 153.4, 96.3.

Compound 14 was prepared from 13 and 1,4diiodobutane as described above for 15.

The product was purified by column chromatography using hexanes and ethyl acetate (4:1) as eluant; yield 79%. ¹H-NMR (CDCl₃): δ 1.04 (t, J=7.10 Hz, 3H, CH₃), 1.63 (m, 4H, CH₂), 2.30 (s, 6H, 2CH₃), 2.58 (s, 12H, 4CH₃), 3.04 (t, J=6.50 Hz, 2H, CH₂I), 3.16 (m, 4H, NCH₂), 3.78 (d, J=5.14 Hz, 4H, NCH₂), 5.55 (m, 2H, CH=CH), 6.94 (s, 2H, Ph), 6.95 (s, 2H, Ph); ¹³C-NMR (CDCl₃): δ 5.69, 12.92, 20.95, 22.72, 22.78, 28.25, 30.36, 40.47, 41.59, 42.11, 44.71, 128.34, 129.00, 131.94, 132.06, 132.60, 132.89, 140.15, 140.21, 142.50, 142.71.

Compound 16 was prepared from 4 and 4-bromobutyronitrile as described above for Compound 2 in 94% yield.

¹NMR(CDCl₃): δ 0.97 (t, J=7.12 Hz, 3H, CH₃), 1.40 (m, 4H, 2CH₂), 1.85 (Pent., m, 2H, CH₂), 2.27 (t, J=7.17 Hz, 2H CH₂CN), 2.30 (s, 6H, 2CH₃), 2.57 (s, 6H, 2CH₃), 2.58 (s, 6H, 2CH₃), 3.13 (m, 6H, NCH₂), 3.28 (t, J=7.11 Hz, 2H, NCH₂), 6.94 (s, 2H, Ph), 6.96 (s, 2H, Ph); ¹³C NMR (CDCl₃): δ 12.55, 14.54, 20.84, 22.64, 22.73, 23.65, 24.43, 24.57, 39.88, 44.31, 44.54, 45.58, 118.69, 131.84, 132.05, 132.73, 133.36, 139.94, 142.20, 142.71.

Compound 17 was prepared from 16 as described above for Compound 3 in 93% yield.

¹H NMR(CDCl₃): δ 1.00 (t, J=6.92 Hz, 3H, CH₃), 1.40 (m, 10H, 4CH₂, NH₂), 2.29 (s, 6H, 2CH₃), 2.57 (b, 14H, 4CH₃, CH₂N), 3.13 (m, 8H, 4CH₂N), 6.93 (s, 4H, 2 Ph); ¹³C NMR (CDCl₃): 12.72, 20.90, 22.72, 22.78, 24.67, 24.80, 30.80, 40.02, 41.61, 44.56, 45.10, 45.38, 131.87, 140.04, 142.21, 142.28; MS-FAB (M/Z) 552.3 (M⁺, 100%), 368.2, 299.1, 183.0, 154.0.

Compound 18 was prepared from 17 as described above for Compound 4.

¹H NMR(CDCl₃): δ 0.96 (t, J=7.13 Hz, 3H, CH₃), 1.38 (m, 8H, 4CH₂), 2.29 (s, 9H, 3CH₃), 2.55 (s, 6H, 2CH₃), 2.56 (s, 6H, 2CH₃); 2.59 (s, 6H, 2CH₃), 2.80 (m, 2H, CH₂N), 3.10 (m, 8H, NCH₂), 4.67(t, J=6.6 Hz, 1H, NH), 6.93 (s, 6H, 3 Ph); ¹³C NMR(CDCl₃): δ 12.56, 20.87, 22.70, 22.74, 22.84, 24.40, 26.45, 24.67, 26.62, 39.87, 41.88, 44.45, 45.02, 45.09, 131.86, 131.90, 131.92, 133.12, 133.32, 133.68, 138.91, 139.97, 142.02, 142.21, 142.38; MS-FAB(M/Z): 756.9(M+23(Na), 100%) 572.8, 390.7, 333.6, 305.6

Compound 19 was prepared from 4 and 1,4-dichloro-2-butene as described above for 15 in 99% yield. ¹H-NMR (CDCl₃): δ 1.01 (t, J=7.11 Hz, 3H, CH₃), 1.38 (m, 4H, CH₂), 2.29 (s, 3H), 2.30 (s, 3H), 2.57 (s, 6H), 2.61 (s, 6H), 3.11 (m, 4H, NCH₂), 3.16 (q, J=7.15 Hz, 2H, NCH₂), 3.81 (d, J=7.17 Hz, 2H, NCH₂), 3.98 (d, J=8.05 Hz, 2H, CH₂Cl), 5.51 (m, 1H, CH=CH), 5.77 (m, 1H, CH=CH), 6.93 (s, 2H, Ph), 6.95 (s, 2H, Ph); ¹³C-NMR (CDCl₃): δ 12.76, 20.91, 22.71, 22.76, 24.74, 38.12, 40.08, 41.85, 44.59,45.54, 129.14, 129.25, 131.88, 132.02, 140.09, 140.19, 142.21, 142.63. MS-FAB (m/z) 569.3 (M⁺, 20%), 385.2, 240.1, 203.3, 183.0, 119 (100%).

Compound 20 was prepared from 18 and 15 following the procedure described above for 15. It was purified by column chromatography using hexanes-ethyl acetate (7:3) as eluant (78% yield). ¹H-NMR (CDCl₃): δ 0.97 (t, J=7.10 Hz, 3H, CH₃), 0.99 (t, J=7.0 Hz, 3H, CH₃), 1.29 (m, 8H, CH₂), 2.29 (s, 15H, CH₃), 2.54, 2.55, 2.59 (s, 30H, CH₃), 3.06 (m, 12H, NCH₂), 3.65 (m, 8H, NCH₂), 5.48 (m, 4H, CH=CH), 6.92 (s, 10H, Ph); ¹³C-NMR (CDCl₃): δ 12.70, 12.83, 20.88, 20.91, 22.65, 22.68, 22.72, 22.74, 24.48, 24.72, 40.04, 40.47, 41.53, 42.07, 42.22, 42.34, 44.54, 44.96, 127.94, 128.27, 128.57, 129.20, 131.92, 132.05, 139.96, 140.00, 140.12, 140.16, 140.27, 142.19, 142.25, 142.47, 142.58, 142.87. MS-FAB (m/z) 1263.81 (M⁺, 100%), 1080.01, 898.11, 714.81, 563.

Compound 21: Pentamide 20 (0.93 g, 0.735 mmol) was dissolved in 20 ml anhydrous CH₂Cl₂, phenol (3.46 g, 36.77 mmol) was added, followed by HBr in acetic acid (30%, 17.62 ml) and the mixture was stirred over night at 25° C. Water (10 ml) was added to the flask, the aqueous layer was separated, the organic layer was extracted with 5 ml H₂O, and the combined aqueous layers were washed with CH₂Cl₂ (6×15 ml). Water was evaporated under vacuum to afford a solid which was dissolved in 1 ml 1N NaOH followed by 1 ml of 50% KOH. This solution was extracted with CHCl₃ (10×5 ml). The combined organic layers were dried (MgSO₄), CHCl₃ was evaporated, and the residue dissolved in anhydrous diethyl ether. Anhydrous HCl gas was passed into the solution while cooling at 0° C. A white solid precipitated which was filtered and washed with ether. It was 21 (84%). ¹H-NMR (D₂O): δ 1.29 (t, J=7.32 Hz, 3H, CH₃), 1.31 (t, J=7.24 Hz, 3H, CH₃), 1.79 (m, 8H, CH₂), 3.12 (m, 12H, NCH₂), 3.87 (m, 8H, NCH₂), 5.98 (m, 4H, CH=CH); ¹³C-NMR (D₂O): δ 13.36, 13.46, 25.66, 25.77, 45.44, 45.74, 46.24, 46.41, 46.84, 49.09, 49.41, 49.70, 129.02, 129.16, 129.47, 129.66. MS-MALDI (m/z) 354.36 (MH⁺, 100%).

Compound 22 was prepared in 51% yield from 18 and 14 as described above for compound 15. ¹H-NMR (CDCl₃): δ 0.97 (t, J=6.59 H, 3H, CH₃), 0.99 (t, J=7.02 Hz, 3H, CH₃), 1.29 (m, 12H, CH₂), 2.29 (s, 15H, CH₃), 2.55 (s), 2.56 (s), 2.57 (s), 3.10 (m, 16H, NCH₂), 3.70 (m, 4H, NCH₂), 5.47 (m, 2H, CH=CH), 6.93 (s, 10H, Ph); ¹³C-NMR (CDCl₃): δ 12.69, 12.83, 20.91, 22.69, 22.71, 22.76, 24.43, 24.70, 40.48, 41.11, 41.48, 44.50, 44.91, 128.13, 128.90, 131.88, 131.94, 132.01, 133.29, 139.95, 140.00, 140.15, 142.22, 142.29, 142.60. MS-FAB (m/z) 1265.91 (M⁺, 100%), 1082.01, 900.11, 716.91, 563.81.

Compound 23 was prepared from 22 in 79% yield as described above for 21. ¹H-NMR (D₂O): δ 1.29 (t, J=7.29 Hz, 3H, CH₃), 1.30 (t, J=7.30 Hz, 3H, CH₃), 1.78 (m, 12H, CH$_2$), 3.12 (m, 16H, NCH$_2$), 3.83 (m, 4H, NCH$_2$), 5.96 (m, 2H, CH=CH); $^{13}$C-NMR (D$_2$O): δ 13.31, 13.42, 25.62, 25.75, 45.38, 45.71, 46.18, 46.76, 49.07, 49.32, 49.69, 129.11, 129.39. MS-MALDI (m/z) 356.38 (MH$^+$, 100%).

Compound 24 was prepared from 18 (52% yield) as described. $^1$H-NMR (CDC$_{l3}$): δ 0.95 (m, 6H, 2CH$_3$), 1.32 (m, 12H, CH$_2$), 2.29 (s, 15H, CH$_3$), 2.55 (s, 30H, CH$_3$), 3.06 (m, 16H, NCH$_2$), 3.70 (m, 4H, NCH$_2$), 5.47 (m, 2H, CH=CH), 6.92 (s, 10H, Ph); $^{13}$C-NMR (CDCl$_3$): δ 12.67, 20.90, 22.71, 22.76, 24.43, 24.68, 39.97, 42.08, 44.48, 44.90, 45.61, 128.28, 128.45, 131.87, 131.93, 132.01, 139.96, 140.00, 140.12, 142.21, 142.28, 142.58. MS-FAB (m/z) 1265.91 (M$^+$, 100%), 1082.01, 900.11.

Compound 25 was prepared from 24 in 96% yield as described above for 21. $^1$H-NMR (D$_2$O): δ 1.28 (t, J=7.29 Hz, 6H, 2CH$_3$), 1.78 (m, 12H, CH$_2$), 3.09 (m, 16H, NCH$_2$), 3.84 (m, 4H, NCH$_2$), 5.96 (m, 2H, CH=CH); $^{13}$C-NMR (D$_2$O): δ 13.31, 25.61, 25.73, 45.70, 46.79, 49.05, 49.36, 49.65, 129.19. MS-MALDI (m/z) 356.4 (MH$^+$).

Compound 26: A mixture of KOH (0.25 g), K$_2$CO$_3$ (0.25 g) and tetra-n-butyl-ammonium hydrogen bromide (0.05 g) were suspended in 15 ml benzene. Mesitylenesulfonylamide (0.199 g, 1 mmol) was added to the suspension and the mixture was heated to 50° C. Iodide 14 (1.98 g, 3 mmol) in 10 ml benzene was added to the flask, the mixture heated under reflux over night, then cooled to room temperature; the inorganic solids were filtered off and washed with benzene (2×20 ml). The combined organic layers were washed several times with water until the washings were neutral. The benzene was dried (MgSO$_4$), evaporated and the residue purified by column chromatography using hexanes and ethyl acetate (7.5:2.5) as eluant; 25% yield (0.948 g). $^1$H-NMR (CDCl$_3$): δ 1.00 (t, J=7.18 Hz, 6H, CH$_3$), 1.28 (m, 8H, CH$_2$), 2.29 (s, 15H, CH$_3$), 2.53 (s), 2.55 (s), 2.57 (s), 3.03 (m, 8H, NCH$_2$), 3.12 (q, J=7.13 Hz, 4H, NCH$_2$), 3.70 (m, 8H, NCH$_2$), 5.47 (m, 4H, CH=CH), 6.93 (s, 10H, Ph); 13C-NMR (CDCl$_3$): δ 12.78, 20.85, 22.63, 22.69, 24.32, 24.58, 40.41, 41.43, 42.00, 44.76, 45.43, 128.08, 128.83, 131.88, 131.95, 132.77, 132.85, 133.23, 139.90, 140.04, 140.08, 142.22, 142.43, 142.53. MS-FAB (m/z) 1263.81 (M$^+$, 100%), 1081, 898.11, 815.01, 561.81, 418.81.

Compound 27 was prepared from 26 in 57% yield as described above for 21. $^1$H-NMR (D$_2$O): δ 1.31 (t, J=7.31 Hz, 6H, CH$_3$), 1.78 (m, 8H, CH$_2$), 3.15 (m, 12H, NCH$_2$), 3.83 (m, 8H, NCH$_2$), 5.96 (m, 4H, CH=CH); $^{13}$C-NMR (CDCl$_3$): δ 13.43, 25.64, 25.76, 45.39, 46.19, 46.77, 49.35, 49.72, 129.11, 129.41. MS-MALDI (m/z) 354.3 (MH$^+$, 100%).

Compound 28 was prepared from 15 and mesitylenesulfonylamide in 24% yield as described above for 26; mp 57.7° C. $^1$H-NMR (CDCl$_3$): δ 0.99 (t, J=7.09 Hz, 6H, CH$_3$), 2.29 (s, 15H, CH$_3$), 2.53 (s), 2.55 (s), 3.12 (q, J=7.09 Hz, 4H, NCH$_2$), 3.63 (m, 16H, NCH$_2$), 5.49 (m, 8H, CH=CH), 6.93 (s, 10H, Ph); $^{13}$C-NMR (CDCl$_3$): δ 12.85, 20.89, 20.92, 22.66, 40.47, 41.53, 42.19, 128.00, 128.47, 128.58, 129.11, 131.92, 132.05, 140.17, 140.30, 142.46, 142.87. MS-FAB (m/z) 1259.81 (M$^+$, 60%), 1075.91, 894.01, 306.51, 153.4 (100%).

Compound 29 was prepared from 28 in 81% yield as described above for 21. $^1$H-NMR (D$_2$O): δ 1.31 (t, J=7.29 Hz, 6H, CH$_3$), 3.15 (q, J=7.31 Hz, 4H, NCH$_2$), 3.84 (m, 4H, NCH$_2$), 3.90 (m, 12H, NCH$_2$), 5.98 (m, 8H, CH=CH); $^{13}$C-NMR (D$_2$O): δ 13.42, 45.41, 46.22, 46.44, 129.07, 129.37, 129.42, 129.58. MS-MALDI (m/z) 350.31 (MH$^+$).

Compound 30 was prepared from 19 in 25% yield as described above for 26; mp 62.3° C. $^1$H-NMR (CDCl$_3$): δ 0.95 (5, J=7.17 Hz, 6H, CH$_3$), 1.33 (m, 8H, CH$_2$), 2.29 (s, 15H, CH$_3$), 2.54 (s), 2.55 (s), 3.07 (m, 12H, NCH$_2$), 3.65 (m, 8H, NCH$_2$), 5.48 (m, 4H, CH=CH), 6.92 (s, 10H, Ph); $^{13}$C-NMR (CDCl$_3$): δ 12.69, 20.90, 22.69, 22.73, 24.70, 40.03, 42.13, 42.30, 44.53, 45.59, 128.11, 128.79, 131.87, 132.00, 140.02, 140.14, 140.28, 142.17, 142.58, 142.85. MS-FAB (m/z) 1263.81 (M$^+$, 100%), 1080.01, 898.11, 714.01, 153.

Compound 31 was prepared from 30 in 87% yield as described above for 21. $^1$H-NMR (D$_2$O): δ 1.28 (t, J=7.32 Hz, 6H, CH$_3$), 1.79 (m, 8H, CH$_2$), 3.10 (m, 12H, NCH$_2$), 3.87 (m, 8H, NCH$_2$), 5.98 (m, 4H, CH=CH); $^{13}$C-NMR (D$_2$O): δ 12.70, 25.00, 25.13, 45.10, 45.81, 46.21, 48.44, 48.78, 128.44, 128.85. MS-MALDI (m/z) 354.3 (MH$^+$).

Compound 32: Mesitylenesulfonylamide (1.47 g, 7.38 mmol) was dissolved in 50 ml anhydrous DMF, and NaH (85%, 0.3 g) was added to it under a nitrogen atmosphere. The mixture was stirred at room temperature and 19 (1.40 g, 2.46 mmol) in 25 ml DMF were added. Heating at 65° C. continued over night. The mixture was cooled to room temperature, and 10 ml of H$_2$O were added. The solvents were evaporated and the solid residue was partitioned between 40 ml H$_2$O and 40 ml CHCl$_3$. The aqueous layer was extracted with CHCl$_3$ (2×30 ml), the combined organic layers were washed with H$_2$O (3×50 ml), dried (MgSO$_4$), and evaporated. The residue was purified by column chromatography using hexanes-ethyl acetate (7.5:2.5). 1.7 g (97%) of 32 as a white solid was obtained. $^1$H-NMR (CDCl$_3$): δ 0.94 (t, J=7.10 Hz, 3H, CH$_3$), 1.30 (m, 4H, CH$_2$), 2.29 (s), 2.30 (s), 2.55 (s, 12H, CH$_3$), 2.65 (s, 6H, CH$_3$), 3.11 (m, 6H, NCH$_2$), 3.52 (m, 1H, NCH), 3.65 (m, 2H, NCH$_2$), 3.71 (m, 1H, NCH$_2$), 4.82 (br, 1H, NH), 5.47 (m, 2H, CH=CH), 6.93 (s, 4H, Ph), 6.96 (s, 2H, Ph); $^{13}$C-NMR (CDCl$_3$): δ 12.50, 20.91, 22.71, 22.76, 22.83, 22.91, 24.66, 38.98, 39.85, 42.15, 42.26, 44.50, 128.06, 128.51, 131.86, 131.91, 138.18, 140.00, 140.14, 140.28, 142.17, 142.65.

Compound 33 was prepared from 32 and 14 in 51% yield as described above for 22. $^1$H-NMR (CDCl$_3$): δ 0.99 (5, J=7.19 Hz, 6H, CH$_3$), 1.33 (m, 8H, CH$_2$), 2.29 (s, 15H, CH$_3$), 2.55 (s), 2.57 (s), 3.10 (m, 12H, NCH$_2$), 3.70 (m, 4H, NCH$_2$), 3.77 (m, 4H, NCH$_2$), 5.42 (m, 4H, CH=CH), 6.93 (s, 10H, Ph); $^{13}$C-NMR (CDCl$_3$): δ 12.70, 12.71, 20.89, 22.66, 22.72, 22.78, 22.81, 24.60, 26.53, 40.39, 41.37, 41.87, 42.20, 45.47, 128.26, 128.62, 131.78, 131.84, 131.86, 131.92, 132.77, 138.92, 139.96, 140.09, 140.17, 142.57, 142.63.

Compound 34 was prepared from 33 as described above for 21 in 40% yield.

Compound 35 was prepared from 15 in 94% yield as described above for 32.

Compound 36 was prepared from 35 and 14 in 82% yield as described above for 33. $^1$H-NMR (CDCl$_3$): δ 0.99 (t, J=7.11 Hz, 6H, CH$_3$), 1.33 (m, 4H, CH$_2$), 2.29 (s, 15H, CH$_3$), 2.55 (s), 2.57 (s), 3.07 (m, 8H, NCH$_2$), 3.70 (m, 12H, NCH$_2$), 5.46 (m, 6H, CH=CH), 6.92 (s, 10H, Ph); $^{13}$C-NMR (CDCl$_3$): δ 12.69, 12.80, 20.84, 22.62, 22.68, 22.73, 22.77, 24.58, 26.55, 40.44, 41.51, 41.86, 42.04, 42.24, 45.49, 128.10, 128.25, 128.52, 128.62, 128.82, 131.89, 131.95, 132.79, 138.89, 140.07, 140.14, 140.23, 141.94, 142.44, 142.53, 142.82. MS-FAB (m/z) 1262.8 (M$^+$, 75%), 1080.01, 896, 119 (100%).

Compound 37 was prepared from 36 in 65% yield as described above for 21. $^1$H-NMR (D$_2$O): δ 1.31 (t, J=6.97 Hz, 6H, CH$_3$), 1.79 (m, 4H, CH$_2$), 3.12 (m, 8H, NCH$_2$), 3.83 (m, 12H, NCH$_2$), 5.96 (m, 6H, CH=CH); $^{13}$C-NMR (D$_2$O): δ 13.48, 25.69, 26.76, 41.67, 45.44, 46.24, 46.45, 46.80, 49.41, 129.00, 129.12, 129.45, 129.71. MS-MALDI (m/z) 352.3 (M$^+$).

Compound 38 was prepared from 35 and 19 in 89% yield as described. $^1$H-NMR (CDCl$_3$): δ 0.95 (m, 6H, CH$_3$), 1.33 (m, 4H, CH$_2$), 2.29 (s, 15H, CH$_3$), 2.54 (s), 2.55 (s), 2.57 (s), 3.09 (m, 8H, NCH$_2$), 3.66 (m, 12H, NCH$_2$), 5.48 (m, 6H, CH=CH), 6.93 (s, 10H, Ph); $^{13}$C-NMR (CDCl$_3$): δ 12.51, 12.63, 20.84, 20.86, 22.63, 22.65, 22.84, 24.61, 38.92, 40.40, 41.40, 42.11, 42.18, 44.44, 45.48, 127.95, 128.07, 128.49, 128.62, 128.80, 131.76, 131.83, 131.85, 131.88, 132.01, 138.05, 139.01, 140.07, 140.13, 140.24, 142.15, 142.21, 142.87. MS-FAB (m/z) 1263.1 (M$^+$, 90%), 1080.1, 896.01, 119 (100%).

Compound 39 was prepared from 38 in 54% yield as described above for 21; mp 270° C. (dec.). $^1$H-NMR (D$_2$O): δ 1.31 (m, 6H, CH$_3$), 1.80 (m, 4H, CH$_2$), 3.10 (m, 8H, NCH$_2$), 3.86 (m, 12H, NCH$_2$), 5.98 (m, 6H, CH=CH); $^{13}$C-NMR (D$_2$O): δ 13.30, 13.42, 25.58, 25.70, 45.69, 46.21, 46.43, 46.81, 49.02, 49.37, 129.00, 129.15, 129.37, 129.59. MS-MALDI (m/z): 352.343 (MH$^+$).

Compound 42: NaH (80%, 132 mg, 4.4 mmol) was added to a solution of diamide 41 (1.98 g, 4.4 mmol) in DMF (10 ml). The mixture was stirred at 20° C. for 30 minutes and a solution of the diester 40 (Reddy et al. (1998) J. Med Chem., 41:4723) (960 mg, 2 mmol) in DMF (10 ml) was added dropwise. The mixture was stirred at 75° C. for 2 h, the solvent was distilled off, the residue was taken in chloroform, washed with a saturated solution of ammonium chloride, dried (Na$_2$SO$_4$) and evaporated to dryness. The crude oil was purified by column chromatography using hexane-ethyl acetate (8:2) as running solvent. 1.4 g (70%) was obtained as a glassy oil. $^{13}$C-NMR (CDCl$_3$): δ 20.58, 22.63, 22.80, 32.42, 33.86, 43.16, 45.42, 46.26, 132.75, 133.21, 139.82, 142.40. MS-FAB 984 (M$^+$), Compound 43: Phenol (1.86 g, 19,7 mmol) and 30% HBr in glacial acetic acid (35 ml) were added in that order to a solution of 42 (600 mg, 0.6 mmol) in CH$_2$Cl$_2$ (35 ml) at room temperature. The solution was stirred for 24 h, water (30 ml) was added, followed by extraction with methylene chloride (3×20 ml). The aqueous layer was evaporated under reduced pressure and the residue was taken up in 2N NaOH (2 ml) and then 50% KOH (2 ml) followed by extraction with chloroform (6×10 ml). After removal of chloroform, the residue was taken up in ethanol (15 ml) and acidified with concentrated hydrochloric acid (0.4 ml). The product 43 (230 mg, 93%) was recrystallized from aqueous ethanol; mp>270° C. (decomp). $^1$H-NMR (D$_2$O): δ 1.95 (m, 2H), 2.05–2.25 (m, 6H), 2.75 (s, 6H), 2.90 (b, 2H), 3.10–3.35 (m, 12H); $^{13}$C-NMR (D$_2$O): δ 25.21, 25.24, 35.60, 35.64, 47.41, 48.58, 50.87. MS-MALDI (m/z) 240 (M$^+$+1).

Compound 47: NaH (80%, 132 mg, 4.4 mmol) was added to a solution of diamide 46 (1.98 g, 4.4 mmol) in DMF (10 ml). The mixture was stirred at 20° C. for 30 min and a solution of the diester 8 (900 mg, 2 mmol) in DMF (10 ml) was added dropwise. The mixture was stirred at 75° C. for 2 h. The solvent was distilled off, the residue was taken up in chloroform, washed with a saturated solution of ammonium chloride, dried (NaSO$_4$) and evaporated to dryness. The oily residue was crystallized from ethyl acetate/hexane 1.2 g (61%); mp 165–166° C. $^1$H-NMR (CDCl$_3$): δ 1.08 (t, 3H), 1.75 (m 4H), 2.28 (s, 12H), 2.55 (bs, 24H), 3.10 (m, 12H), 3.98 (s, 4H), 6.95 (m, 8H); $^{13}$C-NMR (CDCl$_3$): δ 12.70, 20.86, 22.64, 25.14, 34.85, 40.22, 42.62, 43.37, 78.80, 131.99, 132.26, 133.21, 140.26, 142.28, 142.71. MS-FAB (m/z) 982 (M$^+$).

Compound 48 was obtained as described for 47. From 1.2 g (1.22 mmol) of tetramide 47, 420 mg (86%) of the tetrahydrochloride 48 was obtained; mp>270° C. (decomp). $^1$H-NMR (D$_2$O): δ 1.29 (t, 6H), 2.13 (m, 4H), 3.14 (m, 12H), 4.06 (s, 4H); $^{13}$C-NMR (D$_2$O): δ 13.34, 25.52, 39.45, 45.90, 45.64, 46.71, 81.32. MS-MALDI (m/z) 255 (M$^+$+1).

Compound 44 was obtained as described for 47. From 450 mg (1 mmol) of diester 8 and 994 mg (2.2 mmol) of diamide 41, 500 mg (52%) of the tetramide 44 was obtained and crystallized from ethyl acetate-hexane; mp 155–156° C.

Compound 45 was obtained as described for 43. From 500 mg (0.52 mmol) of tetramide 44, 160 mg (82%) of the tetrahydrochloride 45 was obtained; mp>270° C. (decomp). $^1$H-NMR (D$_2$O): δ 2.15 (m, 4H), 2.73 (s, 3H), 3.05–3.40 (m, 8H), 4.10 (s, 4H); $^{13}$C-NMR (D$_2$O): δ 25.59, 35.66, 45.90, 46.57, 48.61.

Compound 51 is a mixture of cis/trans-isomers. $^1$H-NMR (D$_2$O): δ 1.15–2.10 (m, 7H), 2.90 (q, 1H), 3.30–3.80 (b, 2H); $^{13}$C-NMR (D$_2$O): δ 24.16, 24.97, 28.44, 30.42, 36.58, 37.14, 48.24, 52.27, 55.19, 57.45, 64.55, 67.26.

Compound 52: Mesitylenesulfonylchloride (6.5 g, 30 mmol) in dioxane (10 ml) was added dropwise to a stirred and cooled mixture of amine alcohol 51 (1.15 g, 10 mmol), triethylbenzyl ammonium bromide (135 mg, 0.5 mmol), 50% KOH (10 ml) and dioxane (10 ml). The reaction mixture was left over night at 20° C. with magnetic stirring. An excess of water was added, the solution was extracted with chloroform (3×30 ml), dried (Na$_2$SO$_4$) and evaporated to dryness. The oily residue was chromatographed on a silica-gel column using hexane:ethyl acetate (8:2) as eluants. Crystallization from ethyl acetate-hexane afforded 1.2 g (25%) of pure 52; mp 167–168° C. $^1$H-NMR (CDCl$_3$): δ 1.35–1.90 (6H), 1.90–2.15 (m, 1H), 2.30, 2.35 (s, 6H), 2.65 (s, 12H), 3.20 (m, 1H), 3.70 (m, 1H), 3.90 (m, 1H), 5.15 (d, 1H), 6.90, 7.00 (s, 4H); $^{13}$C-NMR (CDCl$_3$): δ 20.73, 20.85, 22.15, 22.37, 22.70, 26.94, 32.75, 45.34, 56.09, 70.38, 130.22, 131.57, 133.98, 138.68, 139.64, 142.02, 143.10. MS-EI (m/z) 479 (M$^+$), 280 (M$^⊕$−199).

Compound 54: NaH (105 mg, 3.5 mmol) was added to a solution of compound 52 (1.7 g, 3.5 mmol) in DMF (10 ml). The mixture was stirred at 20° C. for 30 min and a solution of compound 53 (1.34 g, 3.85 mmol) in DMF (5 ml) was added in small portions. The mixture was stirred at 75° C. for 2 h. The solvent was distilled off, the residue was taken up in chloroform, washed with a saturated solution of ammonium chloride, dried (Na$_2$SO$_4$) and evaporated. The oily residue was purified by column chromatography (hexane-ethyl acetate 8:2) which gave compound 54 (1.22 g, 47%). $^1$H-NMR (CDCl$_3$): δ 1.98 (t, 3H), 1.20–2.05 (9H), 2.20 (s, 6H), 2.55, 2.65 (s, 12H), 2.70–3.55 (9H), 6.85 (s, 4H); $^{13}$C-NMR (CDCl$_3$): δ 12.49, 20.80, 21.64, 21.87, 22.88, 28.72, 33.16, 36.13, 39.96, 43.80, 47.95, 57.77, 61.26, 131.83, 132.94, 133.14, 138.82, 139.90, 142.07, 142.63. MS-FAB (m/z) 628 (M$^+$+1), 546 (M$^+$−81).

Compound 55 was obtained following the procedure described for compound 42. From 1.22 g (1.6 mmol) of bromoderivative 54 and 820 mg (1.76 mmol) of diamide 46, 1.26 g (77%) of tetramide 55 was obtained as a glassy oil. $^1$H-NMR (CDCl$_3$): δ 0.80 (t, 6H), 1.20–1.75 (6H), 1.90 (m, 1H), 2.15 (s, 12H), 2.35–2.60 (s, 24H), 2.65–3.40 (15H), 6.85 (b, 8H); $^{13}$C-NMR (CDCl$_3$): δ 12.38, 20.71, 22.52, 22.66, 24.72, 27.55, 28.04, 39.19, 39.71, 41.02, 42.33, 42.62, 43.37, 48.81, 61.44, 131.76, 131.88, 133.10, 133.89, 138.66, 139.93, 142.17, 142.33, 142.57. MS-FAB (m/z) 1012 (M$^+$), 828 (M$^+$−184).

Compound 56 was obtained following the procedure described for compound 43. From 1.26 g (1.24 mmol) of tetramide 55, 300 mg (56%) of the tetrahydrochloride 56 was obtained; mp>270° C. (decomp). $^1$H-NM (D$_2$O): δ 1.35 (t, 6H), 1.60 (m, 1H), 1.80 (b, 3H), 2.15 (b, 6H), 2.50 (b, 1H), 3.20 (m, 13H), 3.45 (m, 2H); $^{13}$C-NMR (D$_2$O): δ 13.23, 25.48, 25.73, 25.79, 31.69, 31.99, 43.40, 45.91, 46.43, 46.71, 48.07, 53.20, 75.28. MS-MALDI (m/z) 285 (M$^+$+1).

Compound 57: NaH (80%, 150 mg, 5 mmol) and NaBr (2.5 g, 25 mmol) were added to a solution of compound 52 (2.35 g, 4.9 mmol) in DMF (15 ml). The mixture was stirred at 20° C. for 30 min and a solution of 1-bromoethane (2.2 g, 25 mmol) in DMF (10 ml) was added in small portions. The mixture was stirred at 90° C. for 3 h. The solvent was distilled off, the residue taken up in chloroform, washed with a saturated solution of ammonium chloride, dried (Na$_2$SO$_4$) and evaporated. The product was purified by silica gel chromatography (hexane/ethyl acetate 9:1). The oily residue (1.5 g, 79%) crystallized on standing; mp 68–69° C. $^1$H-NMR (CDCl$_3$): δ 1.10 (t, 3H), 1.30–2.10 (6H), 2.25 (b, 4H), 2.60 (s, 6H), 3.20 (m, 2H), 3.35 (m, 2H), 3.60 (m, 2H), 6.95 (s, 2H); $^{13}$C-NMR (CDCl$_3$): δ 16.35, 20.93, 21.79, 22.89, 29.32, 29.37, 36.54, 38.12, 44.13, 61.40, 131.99, 132.80, 140.20, 142.52. MS-FAB 389 (M$^+$+1), 308 (M$^+$−80).

Compound 59 was obtained following the procedure described for compound 42. From 700 mg (1.80 mmol) of compound 57 and 394 mg (0.9 mmol) of diamide 58, 400 mg (37%) of tetramide 59 were obtained. $^1$H-NMR (CDCl$_3$): δ 0.90 (t, 6H), 1.25–1.80 (m, 8H), 1.80–2.10 (m, 8H), 2.15 (s, 12H), 2.40, 2.50 (s, 24H), 2.60–3.35 (m, 6H), 2.85, 2.90 (s, 8H); $^{13}$C-NMR (CDCl$_3$): δ 16.14, 20.85, 21.95, 21.99, 22.55, 25.49, 28.78, 28.88, 31.49, 37.87, 40.50, 40.83, 43.85, 44.06, 49.30, 61.42, 131.86, 131.96, 133.09, 133.40, 139.93, 139.98, 142.27, 142.40. MS-FAB (m/z) 1052 (M$^\oplus$), 891 (M$^+$−184).

Compound 60 was obtained following the procedure described for compound 43. From 400 mg (0.38 mmol) of tetramide 59, 95 mg (53%) of the tetrahydrochloride derivative were obtained; mp>270° C. (decomp.) $^1$H-NMR (D$_2$O): δ 1.30 (t, 6H), 1.60 (m, 2H), 1.80 (m, 6H), 1.95–2.35 (6H), 2.45 (m, 2H), 3.20 (m, 10H), 3.40 (m, 4H); $^{13}$C-NMR (D$_2$O): δ 13.59, 25.34, 25.71, 31.75, 32.00, 43.34, 44.83, 48.02, 53.24, 64.52. MS-MALDI (m/z) 325 (M$^+$1).

Compound 62: Mesitylenesulfonylchloride (3.27 g, 15 mmol) in dioxane (20 ml) was added dropwise to a stirred solution of 61 (1.3 g, 10 mmol) in dioxane (20 ml) and 50% KOH (15 ml) at 0° C. When addition was completed, the mixture was left over night at 20° C. Excess water was added, the solution cooled and the precipitate filtered off. Crystallization from ethylacetate-hexane gave compound 62 (2 g, 80%); mp 115–116° C. $^1$H-NMR (CDCl$_3$): δ 2.35 (s, 3H), 2.55 (t, 2H), 2.65 (s, 6H), 3.25 (q, 2H), 5.15 (t, 1H), 7.0 (s, 2H); $^{13}$C-NMR (CDCl$_3$): δ 19.07, 20.82, 22.78, 38.37, 117.56, 132.07, 133.0, 138.99, 142.67. MS-EI (m/z) 252 (M$^+$).

Compound 63: NaH (80%, 330 mg, 11 mmol) was added to a solution of compound 62 (2.52 g, 10 mmol) in DMF (20 ml) under N$_2$. The mixture was stirred for 30 min and a solution of compound 53 (3.82 g, 11 mmol) in DMF (10 ml) was added in small portions. The mixture was stirred at 70° C. for 2 h. The solvent was distilled off, the residue taken up in chloroform, washed with a saturated solution of ammonium chloride, dried (Na$_2$SO$_4$) and evaporated to dryness. The product was purified by silica-gel chromatography (hexane-ethyl acetate 8:2). The oily residue (3.0 g, 57%) crystallized on standing; mp 105–106° C. $^1$H-NMR (CDCl$_3$): δ 1.00 (t, 3H), 1.75 (m, 2H), 2.35 (s, 6H), 2.60 (14H), 3.10 (m, 6H), 3.45 (t, 3H), 6.90, 6.95 (s, 4H); $^{13}$C-NMR (CDCl$_3$): δ 12.63, 16.94, 20.89, 22.67, 25.73, 40.27, 42.19, 42.51, 44.72, 117.36, 131.95, 132.22, 140.06, 140.34, 142.52, 143.33. MS-EI (m/z) 519 (M$^+$), 429 (M$^+$−HCN).

Compound 65: The nitrile 63 (3.0 g, 5.7 mmol) was dissolved in a mixture of ethanol (150 ml) and concentrated hydrochloric acid (1.5 ml). PtO$_2$ was added (300 mg), the mixture was hydrogenated at 50 psi over night, the catalyst was filtered off and the solvent evaporated to afford an oily residue of compound 64, which was used in the next step without further purification. Free base $^1$H-NMR (CDCl$_3$): δ 1.00 (t, 3H), 1.55 (m, 2H), 1.75 (m, 2H), 2.30 (s, 6H), 2.55 (14 H), 2.90–3.30 (8H), 6.95 (s, 4H); $^{13}$C-NMR (CDCl$_3$): δ 12.64, 20.87, 22.69, 25.35, 30.93, 39.04, 40.12, 42.65, 43.11, 131.86, 133.10, 140.04, 142.43. MS-FAB (m/z) 524 (M$^+$+1).

Mesitylenesulfonylchloride (1.86 g, 8.55 mmol) in dioxane (15 ml) was added dropwise to a stirred mixture of 64 (3.0 g, 5.7 mmol) dissolved in dioxane (30 ml) and 50% KOH (15 ml) at 0° C. The reaction mixture was allowed to reach room temperature and was kept for further 2 h. An excess of water was added and the mixture was extracted with chloroform, dried (Na$_2$SO$_4$) and evaporated to dryness. Purification was achieved by silica gel column chromatography using hexane-ethyl acetate (8:2) as eluant; 2.79 g (69%) of 65 were obtained. $^1$H-NMR CDCl$_3$): δ 0.95 (t, 3H), 1.60 (m, 4H), 2.30 (s, 9H), 2.50 (s, 12H), 2.65 (s, 6H), 2.85 (m, 2H), 3.05 (6H), 3.20 (t, 2H), 5.00 (t, 1H), 6.95 (6H); $^{13}$C-NMR CDCl$_3$): δ 12.45, 20.81, 22.73, 25.23, 27.46, 39.19, 33.99, 42.49, 42.92, 43.17, 131.84, 133.05, 133.82, 138.80, 139.90, 141.92, 142.36, 142.64. MS-FAB (m/z) 705 (M$^\oplus$).

Compound 66 was obtained following the procedure described for compound 42. From 705 mg (1 mmol) of 65 and 426 mg (1.1 mmol) of 57, 470 mg (46%) of tetramide 66 was obtained as a glassy product. $^1$H-NMR CDCl$_3$): δ 0.85–1.10 (t, 6H), 1.35–2.10 (m, 11H), 2.30 (s, 12H), 2.40–2.65 (m, 24H), 2.75–3.55 (m, 13H), 6.95 (m, 8H); $^{13}$C-NMR (CDCl$_3$): δ 12.64, 16.11, 20.91, 22.08, 22.75, 24.81, 25.09, 28.83, 29.07, 37.93, 40.08, 40.84, 42.50, 42.81, 43.11, 43.42, 49.11, 61.43. MS-FAB (m/z) 1013 (M++1).

Compound 67 was obtained following the procedure described for compound 43. From 470 mg (0.46 mmol) of tetramide 66, 142 mg (71%) of the tetrahydrochloride derivative was obtained; mp>250° C. (decomp). $^1$H-NMR (D$_2$O): δ 1.30 (t, 6H), 1.60 (m, 1H), 1.85 (b,s, 3H), 2.15 (m, 6H), 2.45 (m, 1H), 3.15 (m, 13H), 3.45 (m, 2H); $^{13}$C-NMR (D$_2$O): δ 13.29, 13.57, 25.34, 25.44, 25.64, 31.68, 31.94, 43.27, 44.80, 45.86, 46.62, 47.42, 47.97, 53.19, 64.50. MS-MALDI 285 (M$^+$+1), 286 (M$^+$+2).

Compound 68a: 4-Cyanobenzaldehyde (Aldrich, 1.31 g, 10 mmol) was dissolved in 30 ml anhydrous MeOH followed by the addition of MgSO$_4$ (anhydrous, 1.5 g) and 1,4-diaminobutane (Aldrich, 0.44 g, 5 mmol) and the mixture was stirred under argon over night. The suspension was cooled in an ice bath and NaBH (2.0 g) was added in portions and stirring continued for 2 h at 0° C. The methanol was evaporated under vacuum and the resulting solid was partitioned between 35 ml H$_2$O and 50 ml CHCl$_3$. Some of the solid was not soluble in either the H$_2$ or the CHCl$_3$ and was filtered off and the aqueous layer was extracted with CHCl$_3$ (2×25 ml). The pooled organic layers were dried (MgSO$_4$), evaporated and the solid was recrystallized from ethyl acetate-hexane, yield 1.1 g (35%); mp 90.6–90.8° C. $^1$H-NMR (CDCl$_3$): δ 1.43 (broad, 2H, NH), 1.55 (m, 4H, CH$_2$), 2.63 (m, 4H, NCH$_2$), 3.85 (s, 4H, benzylic CH$_2$), 7.44 (m, 4H, Ph), 7.60 (m, 4H, Ph); $^{13}$C-NMR CDCl$_3$): δ 27.78, 49.28, 53.44, 110.65, 118.88, 128.52, 132.12, 146.21. MS (m/z) 318 (M$^+$), 185, 145, 131, 116 (100%), 70.

Compound 68b was prepared from 4-cyano-benzaldehyde and 1,5-diaminopentane as described above for 68a; 42% yield; mp 92.9–93.0° C. $^1$H-NMR (CDCl$_3$): δ 1.40 (m, 4H, NH, CH$_2$), 1.50 (m, 4H, CH$_2$), 2.59 (m, 4H, NCH$_2$), 3.83 (s, 4H, benzylic CH$_2$), 7.45 (m, 4H, Ph), 7.59 (m, 4H, Ph); $^{13}$C-NMR (CDCl$_3$): δ 24.86, 29.87, 49.29, 53.40, 110.50, 118.85, 128.48, 132.04, 146.19. MS (m/z) 332 (M$^+$), 216, 199, 145, 116 (100%), 84.

Compound 68c was prepared from 4-cyanobenzyldehyde and 1,6-diaminohexane as described above for 68a; 45% yield; mp 95.6–95.8° C. $^1$H-NMR (CDCl$_3$): δ 1.35 (m, 4H, CH$_2$), 1.50 (m, 6H, NH, CH$_2$), 2.60 (t, J=6.92 Hz, 4H, NCH$_2$), 3.84 (s, 4H, benzylic CH$_2$), 7.44 (m, 4H, Ph), 7.60 (m, 4H, Ph); $^{13}$C-NMR (CDCl$_3$): δ 27.17, 30.02, 49.42, 53.50, 110.65, 118.92, 128.55, 132.14, 146.27. MS (m/z) 346 (M$^+$), 230, 213, 145, 116 (100%) 98.

Compound 69a: Dinitrile 68a (0.75 g, 2.36 mmol) was dissolved in anhydrous THF, lithium bis(trimethylsilyl)amide (9.43 ml of a 1 m solution in THF) was added slowly under argon atmosphere. The mixture was stirred at room temperature for 2 h; then cooled in an ice bath, followed by the addition of 4 equivalents of 6N HCl in ether. A white solid precipitated immediately and was filtered after 12 h. The solid was recrystallized from ethanol-ether to afford 1.19 g of compound 69a (93%). $^1$H-NMR (D$_2$O): δ 1.87 (m, 4H, CH$_2$), 3.22 (m, 4H, CH$_2$N), 4.40 (s, 4H, benzylic CH$_2$), 7.74 (m, 4H, Ph), 7.91 (m, 4H, Ph); $^{13}$C-NMR (DMSO-d6): δ 22.68, 46.09, 49.28, 128.10, 128.47, 130.69, 138.15, 165.44. MS-ESI (m/z) 353.2 (M$^+$), 177.2 (100%).

Compound 69b was prepared from 68b in 92% yield as described above for 69a. $^1$H-NMR (D$_2$O): δ 1.52 (m, 2H, CH$_2$), 1.80 (m, 4H, CH$_2$), 3.19 (m, 4H, NCH$_2$), 4.40 (s, 4H, benzylic CH$_2$), 7.75 (m, 4H, Ph), 7.91 (m, 4H, Ph); $^{13}$C-NMR (DMSO-d$_6$): δ 24.90, 26.91, 48.96, 51.88, 130.29, 130.46, 132.43, 139.51, 167.52. MS-ESI (m/z) 367.2 (M$^+$), 350.2 (100%), 301.2.

Compound 69c was prepared from 68c as described above for 69a in 96% yield. $^1$H-NMR (D$_2$O): δ 1.46 (m, 4H, CH$_2$), 1.78 (m, 4H, CH$_2$), 3.16 (m, 4H, NCH$_2$), 4.39 (s, 4H, benzylic CH$_2$), 7.74 (m, 4H, Ph), 7.91 (m, 4H, Ph); $^{13}$C-NMR (DMSO-d$_6$): δ 25.24, 25.82, 46.73, 49.44, 128.35, 128.56, 130.81, 138.38, 165.58. MS-ESI (m/z) 381.2 (M$^+$), 191.2 (100%), 150, 116.

Compound 70: Triamide 18 (4.3 g, 5.8 mmol) was dissolved in 30 ml of DMF and 80% NaH (208 mg, 6.9 mmol) was added. The mixture was stirred under a N$_2$ atmosphere for 1 h and 1.12 g (7.5 mmol) of bromobutyronitrile dissolved in 3 ml of DMF were added all at once. The reaction mixture was heated for 3 h at 90° C. The solvent was distilled-off and the residue was dissolved in chloroform and washed twice with a saturated solution of amonium chloride; dried (NaSO$_4$) and evaporated to dryness. Flash chromatography of the residue using hexane-ethyl acetate (6:4) as eluant gave the yellow oil 70 (3.7 g, 77%). $^1$H-NMR CDCl$_3$): δ 0.95 (t, 3H), 1.35 (m, 8H), 1.85 (m, 2H), 2.20 (t, 2H), 2.30 (s, 9H), 2.55 (s, 18H), 3.10 (m, 10H), 3.25 (t, 2H), 6.95 (s, 6H). MS-FAB (m/z) 823 (M$^+$+Na), 639, 457.

Compound 71: Nitrile 70 (3.7 g, 4.6 mmol) was dissolved in 20 ml of chloroform and 150 ml of ethanol were added. The mixture was reduced over 0.35 g of PtO$_2$ at 50 psi over night. The catalyst was filtered-off and the solvent evaporated to dryness. The oily residue was dried in vacuo for 2 h and dissolved in 50 ml of Cl$_3$CH and 12 ml 2N NaOH. The mixture was cooled in an icewater bath with efficient magnetic stirring and 1.50 g (6.9 mmol) of mesitylene chloride dissolved in 10 ml of chloroform were added all at once. After 2 h the organic layer was separated, washed twice with a saturated solution of amonium chloride, dried (NaSO$_4$) and evaporated to dryness. Flash chromatography of the residue using hexane-ethyl acetate (7:3) as eluant provided the tetramide 71 as a colorless oil (3.3 g, 73% over two steps). $^1$H-NMR CDCl$_3$): δ 0.95 (t, 3H), 1.40 (m, 12H), 2.30 (s, 12H), 2.60 (s, 24H), 2.80 (b, 2H), 3.10 (m, 12H), 4.70 (b, 1H), 6.90 (s, 8H). MS-FAB (m/z) 1010 ($^{M+}$+1+Na), 826, 643.

Compound 72: The tetramide 71 (6.28 g, 6.3 mmol) was dissolved in 40 ml of DMF and 80% NaH (230 mg, 7.6 mmol) was added. The mixture was stirred under a N$_2$ atmosphere for 1 h and 1.30 g (8.8 mmol) of bromobutyronitrile dissolved in 3 ml of DMF were added all at once. The reaction mixture was heated for 3 h at 90° C., the solvent was distilled-off and the residue was extracted into chloroform and washed twice with a saturated solution of amonium chloride; dried (NaSO$_4$) and evaporated to dryness. Flash chromatography of the residue with hexane-ethyl acetate (7:3) as eluant provided the nitrile 72 (5.0 g, 74%). $^1$H-NMR (CDCl$_3$): δ 0.95 (t, 3H), 1.35 (m, 12H), 1.80 (m, 2H), 2.25 (t, 2H), 2.35 (s, 12H), 2.70 (s, 24H), 3.10 (m, 14H), 3.25 (t, 2H), 7.0 (s, 8H). MS-FAB (m/z) 1077 (M$^+$+1+Na), 893, 711, 586.

Compound 73: Nitrile 72 (6.0 g, 5.6 mmol) was dissolved in 20 ml of chloroform and 150 ml of ethanol were added. The mixture was reduced over 600 mg of PtO$_2$ at 50 psi overnight. The catalyst was filtered-off and the solvent evaporated to dryness. The oily residue was dried in vacuo for 2 h and dissolved in 100 ml of chloroform and 15 ml 2N NaOH. The mixture was cooled in an icewater bath with efficient magnetic stirring, and 1.80 g (8.4 mmol) of mesitylene chloride dissolved in 10 ml of Cl$_3$CH was added all at once. After 2 h the organic layer was separated, washed twice with a saturated solution of amonium chloride, dried (Na$_2$SO$_4$) and evaporated to dryness. Flash chromatography of the residue using hexane-ethyl acetate (7:3) as eluant gave the pentamide 73 as a colorless oil (5.0 g, 71% over two steps). $^1$H-NMR (CDCl$_3$): δ 0.95 (t, 3H), 1.35 (m, 16H), 2.30 (s, 15H), 2.55 (s, 30H), 2.75 (bs, 2H), 3.05 (m, 16H), 4.70 (b, 1H), 6.90 (s, 10H). MS-FAB (m/z) 1261 (M$^+$–1+Na), 1077, 895.

Compound 74: Pentamide 73 (3.4 g, 2.7 mmol) was dissolved in 30 ml of DMF and 60% NaH (162 mg, 4.05 mmol) was added. The mixture was stirred under a N$_2$ atmosphere for 0.5 h and 2.3 g (10.8 mmol) of 2-bromoethanol benzylether dissolved in 3 ml of DMF were added all at once. The reaction mixture was heated for 2 h at 80° C., the solvent was distilled-off and the residue was dissolved in chloroform and washed twice with a saturated solution of amonium chloride, dried (NaSO$_4$) and evaporated to dryness. Flash chromatography of the residue using hexane-ethyl acetate (7:3) as eluant provided the product 74 (2.6 g, 70%). $^1$H-NMR CDCl$_3$): δ 0.95 (t, 3H), 1.30 (m, 16H), 2.30 (s, 15H), 2.50 (s, 30H), 2.90–3.20 (m, 18H), 3.25 (t, 2H), 2.35 (t, 2H), 4.35 (s, 2H), 6.95 (s, 10H), 7.20–7.35 (m, 5H). $^{13}$C NMR (CDCl$_3$): δ 12.65, 20.84, 22.67, 22.71, 24.41, 24.66, 39.97, 44.48, 44.88, 46.59, 68.01, 72.95, 127.46, 127.57, 128.25, 131.83, 131.89, 133.28, 139.88, 139.95, 140.04, 142.16, 142.23. MS-FAB (m/z) 1394 (M$^+$–2+Na) 1030.

Compound 75: Pentamide 74 (1.2 g, 0.87 mmol) was dissolved in 12 ml of methylene chloride followed by the addition of 30% HBr/acetic acid (16 ml) and phenol (3.0 g, 32 mmol). The mixture was stirred at room temperature overnight, water (16 ml) was added, followed by extraction with methylene chloride (3×10 ml). The aqueous layer was evaporated in vacuo. The residue was dissolved in 2N NaOH (4 ml) and 50% KOH (4 ml) followed by extraction with chloroform (4×10 ml). After removal of the solvent the residue was dissolved in ethanol (20 ml) and acidified with concentrated hydrochloric acid (0.5 ml). The white precipitate (75) was recrystallized from aqueous ethanol (440 mg, 90%); mp above 270° C. (decomp.) $^1$H-NMR (D$_2$O): δ 1.30

(t, 3H), 1.75 (b, 16H), 2.90–3.30 (m, 20H), 2.85 (t, 2H). $^{13}$C NMR (D$_2$O): δ 13.29, 25.48, 25.59, 45.70, 49.04, 49.49, 49.67, 51.88, 59.39. MS-MALDI (m/z) 374 (M$^+$+1).

Compound 76: Pentamide 73 (850 mg, 0.68 mmol) was dissovled in DMF (15 ml) and 80% NaH (30 mg, 1 mmol) was added. The mixture was stirred under a N$_2$ atmosphere at room temperature for 0.5 h and 137 mg (0.30 mmol) of 73 dissolved in 5 ml of DMF were slowly added. The reaction mixture was heated for 2 h at 80° C., the solvent was distilled-off and the residue was dissolved in chloroform and washed twice with a saturated solution of amonium chloride, dried (NaSO$_4$) and evaporated to dryness. Flash chromatography of the residue using hexane-ethyl acetate-methanol (6:4:0.1) as eluant afforded the product 76 (590 mg, 77%). $^1$H-NMR (CDCl$_3$): δ 0.95 (t, 6H), 1.15–1.40 (m, 32H), 2.30 (s, 30H), 2.55 (s, 60H), 2.90–3.25 (m, 36H), 3.60 (d, 4H), 5.40 (t, 2H), 6.95 (s, 20H). MS-FAB 2553 (M$^+$+Na).

Compound 77 was obtained following the procedure described for compound 75. From 650 mg (0.25 mmol) of decamide 76, 225 mg (81 %) of decahydrochloride 77 was obtained; mp>270° C. (decomp). $^1$H-NMR (D$_2$O): δ 1.30 (t, 6H), 1.75 (b, 32H), 3.10 (b, 36H), 3.75 (b, 4H), 6.05 (b, 2H); $^{13}$C NMR (D$_2$O): δ 13.28, 25.57, 45.66, 49.00, 49.13, 49.64, 50.86, 131.15. MS-ESI 711 (M$^+$+1).

Compound 78 was obtained following the procedure described for compound 76. From 850 mg of 73, 360 mg (47%) of decamide 78 were obtained. $^1$H-NMR (CDCl$_3$): δ 0.95 (t, 6H), 1.15–1.45 (m, 32H), 2.30 (s, 30H), 2.55 (s, 60H), 2.90–3.20 (b, 36H), 3.65 (d, 4H), 5.40 (t, 2H), 6.90 (s, 20H). MS-FAB (m/z) 2553 (M$^+$+Na).

Compound 79 was obtained following the procedure described for compound 75. From 330 mg (0.13 mmol) of decamide 78, 127 mg (90%) of decahydrochloride 79 was obtained; mp>270° C. (decomp). $^1$H-NMR (D$_2$O): δ 1.30 (t, 6H), 1.80 (b, s, 32H), 3.10 (b, 36H), 3.85 (d, 4H), 6.0 (t, 2H). $^{13}$C NMR (D$_2$O): δ 13.31, 25.59, 45.71, 46.83, 49.05, 49.39, 49.69, 129.21. MS-ESI (m/z) 512 (M$^+$+2).

Compound 96.

Pentamide 74 (1.4 g, 1.01 mmol) was dissolved in 100 ml of ethanol and 200 mg of 10% Pd/C was added. The mixture was hydrogenated for 4 h at 50 psi. The catalyst was filtered off and and solvent evaporated to dryness. Silica-gel column chromatography using ethyl acetate/hexane 6:4 as running solvent afforded 1.0 g (80%) of desired product, as an oil. $^1$NMR (CDCl$_3$) δ: 0.95 (t, 3H), 1.30 (m, 16H), 2.30 (s, 15H), 2.55 (s, 30H), 3.10 (m, 18H), 3.25 (t, 2H), 3.60 (t, 2H), 6.95, (s, 10H), $^{13}$C NMR δ: 12.67, 20.89, 22.75, 24.52, 40.02, 44.54, 44.97, 46.83, 48.22, 60.29, 131.88, 132.78, 133.28, 139.95, 140.11, 142.33

Compound 97

Alcohol 96 (470 mg, 0.36 mmole) was dissolved in tetrahydrofuran (5 ml), Boc-Gln (97 mg, 0.39 mmole), dicyclohexylcarbodiimide (89 mg, 0.43 mmole), and dimethylaminopyridine (5 mg, 0.039 mmole) were added. The reaction mixture was stirred overnight at room temperature. The cyclohexylurea was filtered off and the filtrate evaporated to dryness. The residue was dissolved in chloroform, washed twice with 2N HCl, once with water, and twice with a saturated solution of NaHCO$_3$, then dried and evaporated. The product was purified by silica-gel column chromatography using methanol/chloroform 2% as running solvent. The amino acid-polyamine analog conjugate weighed 250 mg (45%). $^1$NMR (CDCl$_3$) δ: 0.95 (t, 3H), 1.30 (m, 18H), 1.45 (s, 9H), 1.90–2.20 (m, 211), 2.35 (s, 15H), 2.60 (s, 30H) 2.90–3.25 (m, 18H), 3.45 (m, 2H), 4.10–4.35 (m, 3H), 6.95 (s, 10H); $^{13}$C NMR (CDCl$_3$) δ: 12.57, 20.78, 22.63, 24.63, 28.19, 31.48, 39.92, 44.04, 44.43, 44.82, 45.92, 53.06, 61.96, 79.80, 131.99, 133.33, 139.80, 142.12, 156.40, 171.70, 174.25.

Compound 98

Amino acid-polyamine analog conjugate 97 (170 mg, 0.11 mmole) was treated with trifluoroacetic acid (1.25 ml) in methylene chloride (5 ml) for 30 minutes. The solvent was evaporated at room temperature, the residue was dissolved in chloroform and washed with a saturated solution of NaHCO$_3$, then dried and evaporated to dryness. After drying in vacuo, the residue weighted 158 mg (100%). The remaining protecting groups are removed following the procedure described for compound 21.

Example 2

In Vitro Activity of Polyamine- and Polyamine Analog-amino Acid Conjugates

Polyamine- and polyamine analog-amino acid conjugates of the invention were tested for their ability to inhibit growth of various cancer cell lines. The procedures used for testing activity are similar to those used in International Patent Application WO 00/66587 and U.S. Pat. No. 5,889,061 and are described below.

Cell Lines and Media

Human breast cancer cell line MCF7 was grown in Richter's Improved Modified Eagle's Medium supplemented with 10% fetal bovine serum (FBS) and 2.2 g/L sodium bicarbonate. Human brain tumor cell line U251 MG-NCI was grown in Dulbecco's Modified Eagle's Medium supplemented with 10% FBS. Human lung cancer cell line A549 was grown in Ham's F-12K medium (Cellgro, Mediatech, Inc., Va.), supplemented with 10% FBS and 2 mM L-glutamine. Human colon cancer cell line HT129 was cultured in McCoy's 5A medium (Gibco, BRL, Gaithersburg, Md.) supplemented with 10% FBS. Human prostate cancer cell lines PC-3, LNCAP and DuPro were grown in RPMI 1640 Medium (Cellgro, Mediatech, Inc., Va.) supplemented with 10% FBS. Another human prostate cancer cell line DU145 was grown in Dulbecco's Modified Eagle's Medium (Gibco, BRL, Gaithersburg, Md.) supplemented with 5% FBS. The A549, MCF7, PC3, LNCAP and DuPro cell lines were cultured in 100 units/mL penicillin and 100 µg/mL streptomycin. HT29 and U251MG cell lines were grown in 50 µg/mL gentamycin (Gibco, BRL, Gaithersburg, Md.). DU145 cell line was maintained in 1% antibitic-antimycotic solution (Sigma, St. Louis, Mo.) The cell cultures were maintained at 37° C. in 5% CO$_2$/95% humidified air. DuPro cells were obtained from M. Eileen Dolan, University of Chicago. All other cells are available from the American Type Culture Collection, Rockville, Md.

MTT assay

A conventional MTT assay was used to evaluate percent cell survival. Exponentially growing monolayer cells were plated in 96-well plates at a density of 500 cells per well and allowed to grow for 24 hours. Serial dilutions of the drugs were added to the wells. Six days after drug treatment, 25 µl of MTT solution (5 mg/ml) was added to each well and incubated for 4 hours at 37° C. Then 100 µl of lysis buffer (20% sodium dodecyl sulfate, 50% DMF, and 0.8% acetic acid, pH 4.7) was added to each well and incubated for an additional 22 hours. A microplate reader ("EMAX"-brand, Molecular Devices, Sunnyvale, Calif.) set at 570 nm was used to determine the optical density of the cultures. Results are expressed as a ratio of the optical density in drug-treated wells to the optical density in wells treated with vehicle only.

The ID$_{50}$ of two of the compounds of the invention, SL-11143 (a polyamine linked to beta-alanine) and SL-11165 (a polyamine linked to glutamine) against various cancer cell lines are listed in the table below.

| Compound | Structure | ID$_{50}$ DuPro | ID$_{50}$ PC-3 | ID$_{50}$ DU145 | ID$_{50}$ LnCap |
|---|---|---|---|---|---|
| SL-11143 | (structure) (5HCl) | 13.75 | >31.25 | 0.06 | 6.4 |
| SL-11165 | (structure) (5HCl) | >31.65 | 4.1 | | >31.25 |

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The following U.S. patent applications are hereby incorporated by reference herein in their entirety: U.S. Provisional Patent Application Ser. No. 60/131,809, U.S. Provisional Patent Application Ser. No. 60/131,779, and U.S. Provisional Patent Application Ser. No. 60/131,842, all filed on Apr. 30, 1999; and U.S. Ser. Nos. 09/561,172, 09/560,711, and 09/562,980, all filed on Apr. 27, 2000.

All references, patents, patent applications, and non-patent publications mentioned herein are hereby incorporated by reference herein in their entirety.

What is claimed is:

1. A composition comprising a polyamine or polyamine analog conjugated to at least one amino acid, wherein two amino acids are conjugated to the polyamine or polyamine analog, where each amino acid is conjugated to an exterior nitrogen of the polyamine or polyamine analog.

2. A composition comprising a polyamine or polyamine analog conjugated to at least one amino acid, wherein the polyamine- or polyamine analog-amino acid conjugates are of the formula:

(M)-N(-E)-B-A-B-NH-B-A-B-NH-B-A-B-NH-B-A-B-NH-E or (M)-N(-E)-B-A-B-NH-B-A-B-NH-B-A-B-NH-B-A-B-N(M)-E wherein each M is independently an amino acid, each A is independently selected from the group consisting of a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and any salt or stereoisomer thereof.

3. A composition comprising a polyamine or polyamine analog conjugated to at least one amino acid, wherein the polyamine- or polyamine analog-amino acid conjugates are of the formula:

(M)-N(E)B-A-B-NH-B-A-B-NH-B-A-B-NH(-B-A-B-NH)$_x$-E or (M)-N(-E)-B-A-B-NH-B-A-B-NH-

B-A-B-NH(-B-A-B-NH)$_{(x-1)}$-(-B-A-B-N(M))E wherein each M is independently an amino acid, each A is independently selected from the group consisting of: a single bond, $C_2$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and x is an integer from 2 to 16; and any salt or stereoisomer thereof.

4. A composition comprising a polyamine or polyamine analog conjugated to at least one amino acid, wherein the polyamine- or polyamine analog-amino acid conjugates are of the formula:

(M)-N(-E)-B-A-B-NH-B-A-B-NH-B-A-B-NH(-B-A-B-NH)$_x$-E or (M)-HN-B-A-B-NH-B-A-B-NH-

-continued

B-A-B-NH(-B-A-B-NH)$_{(x-1)}$-B-A-B-N(M)-E wherein each M is independently an amino acid, each A is independently selected from the group consisting of: a single bond, $C_2$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and x is an integer from 2 to 16; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and any salt or stereoisomer thereof.

5. A composition comprising a polyamine or polyamine analog conjugated to at least one amino acid, wherein the polyamine- or polyamine analog-amino acid conjugates are of the formula:

(M)E-NH-B-A-B-NH-B-A-B-NH-B-A-B-NH(-B-A-B-NH)$_x$-E(M)

or (M)E-NH-B-A-B-NH-B-A-B-NH-B-A-B-NH(-B-A-B-NH)$_x$-E wherein each M is independently an amino acid, wherein each A is independently selected from the group consisting of: a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of $C_1$–$C_6$ alkyl, $C_1$–$C_6$ alkanol, $C_3$–$C_6$ cycloalkanol, and $C_3$–$C_6$ hydroxyaryl, and the amino acid(s) is linked to the polyamine analog via an ester linkage at the B group hydroxyl(s), with the proviso that each E bearing an amino acid is selected from $C_1$–$C_6$ alkanol, $C_3$–$C_6$ cycloalkanol, and $C_3$–$C_6$ hydroxyaryl; and x is an integer from 0 to 16; and any salt or stereoisomer thereof.

6. A composition comprising a polyamine or polyamine analog conjugated to at least one amino acid, wherein the polyamine- or polyamine analog-amino acid conjugates are of the formula:

(M)E-NH-B-A-B-NH-B-A-B-NH-B-A-B-NH(-B-A-B-NH)$_x$-E(M)

or (M)E-NH-B-A-B-NH-B-A-B-NH-B-A-B-NH(-B-A-B-NH)$_x$-E wherein each M is independently an amino acid, wherein each A is independently selected from the group consisting of: a single bond, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; each E is independently selected from the group consisting of $C_1$–$C_6$ alkyl, $C_1$–$C_6$ alkanol, $C_3$–$C_6$ cycloalkanol, and $C_3$–$C_6$ hydroxyaryl, with the proviso that each E bearing an amino acid is selected from $C_1$–$C_6$ alkanol, $C_3$–$C_6$ cycloalkanol, and $C_3$–$C_6$ hydroxyaryl; and the amino acid(s) is linked to the polyamine analog via an ester linkage to at least one E group hydroxyl(s); and x is an integer from 0 to 16; and any salt or stereoisomer thereof.

7. A composition comprising a polyamine or polyamine analog conjugated to at least one amino acid, further comprising a pharmaceutically acceptable carrier, wherein the polyamine- or polyamine analog-amino acid conjugates are of the formula:

(M)-N(-E)-D-NH-B-A-B-NH-D-NH-E or (M)-N(-E)-D-NH-B-A-B-NH-D-N(M)-E wherein each M is independently an amino acid; A is selected from the group consisting of $C_2$–$C_6$ alkynyl; each B is independently selected from the group consisting of: a single bond, $C_1$–$C_6$ alkyl, and $C_2$–$C_6$ alkenyl; each D is independently selected from the group consisting of $C_1$–$C_6$ alkyl, $C_2$–$C_6$ alkenyl, $C_2$–$C_6$ alkynyl, $C_3$–$C_6$ cycloalkyl, $C_3$–$C_6$ cycloalkenyl, and $C_3$–$C_6$ cycloaryl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; and any salt or stereoisomer thereof.

8. A composition comprising a polyamine or polyamine analog conjugated to at least one amino acid, further comprising a pharmaceutically acceptable carrier, wherein the polyamine- or polyamine analog-amino acid conjugates are of the formula:

(M)-N(-E)-B-A-B-NH-F-NH-B-A-B-NH-E or (M)-N(-E)-B-A-B-NH-F-NH-B-A-B-N(M)-E wherein each M is indepedently an amino acid; wherein F is selected from the group consisting of $C_1$–$C_6$ alkyl; each A is independently selected from the group consisting of: a single bond, $C_1$–$C_6$ alkyl; $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; each B is independently selected from the group consisting of: a single bond, $C_1$–$C_6$ alkyl, and $C_2$–$C_6$ alkenyl; and each E is independently selected from the group consisting of H, $C_1$–$C_6$ alkyl, $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl; with the proviso that either at least one A moiety is selected from the group consisting of $C_2$–$C_6$ alkenyl, $C_2$–$C_6$ alkynyl, $C_3$–$C_6$ cycloalkyl, $C_3$–$C_6$ cycloaryl, and $C_3$–$C_6$ cycloalkenyl, or at least one B moiety is selected from the group consisting of $C_2$–$C_6$ alkenyl; and any salt or stereoisomer thereof.

9. A composition comprising a polyamine or polyamine analog conjugated to at least one amino acid, wherein the amino acid is chosen from D-glutamine or L-glutamine, and all salts thereof.

10. A composition according to claim 9, wherein the amino acid is chosen from L-glutamine, and all salts thereof.

11. A composition comprising a polyamine analog-amino acid conjugate of the formula: $CH_3CH_2—N(R_{100})—J—N(R_{100})—CH_2CH_3$, where each $R_{100}$ is independently chosen from H, $C_1$–$C_8$ alkyl, and an amino acid, with the proviso that at least one $R_{100}$ be an amino acid; and where J is selected from $\{C_1$–$C_8$ alkyl-$[N(R_{100})$-$(C_1$–$C_8$ alkyl$)]_k\}$, where each $R_{101}$ is independently selected from H and $C_1$–$C_8$ alkyl, and where k is an integer between 0 and 15.

12. The composition of claim 11, wherein one and only one $R_{100}$ is an amino acid.

13. The composition of claim 11, wherein one and only one $R_{100}$ is an amino acid and the other $R_{100}$ is H.

14. The composition of claim 11, where the amino acid is chosen from amino acids with either amide-containing or basic side chains, and all stereoisomers and salts thereof.

15. The composition of claim 11, where the amino acid is chosen from glutamine, asparagine, lysine, ornithine, arginine, histidine, or citrulline, and all stereoisomers and salts thereof.

16. The composition of claim 11, where the amino acid is D-glutamine or L-glutamine, and all salts thereof.

17. The composition of claim 11, where the amino acid is L-glutamine, and all salts thereof.

18. A composition comprising a polyamine analog-amino acid conjugate of the formula:

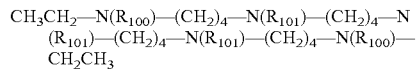

where each $R_{100}$ is independently chosen from H, $C_1$–$C_8$ alkyl, and an amino acid, with the proviso that at least one $R_{100}$ be an amino acid; and each $R_{101}$ is independently chosen from H and $C_1$–$C_8$ alkyl.

19. The composition of claim 11, further comprising a pharmaceutically acceptable carrier.

20. The composition of claim 18, further comprising a pharmaceutically acceptable carrier.

21. The composition of claim 5 wherein the polyamine analog amino acid conjugate is of the formula

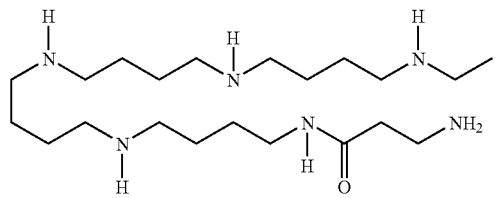

or a salt or stereoisomer thereof.

22. The composition of claim 5 wherein the polyamine analog amino acid conjugate is of the formula

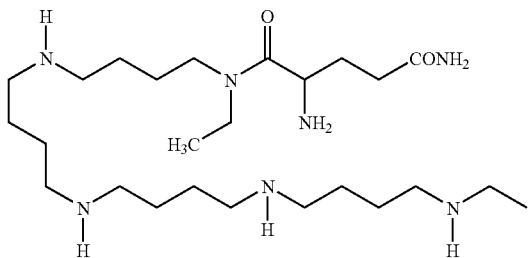

or a salt or stereoisomer thereof.

23. The composition of claim 21, further comprising a pharmaceutically acceptable carrier.

24. The composition of claim 22, further comprising a pharmaceutically acceptable carrier.

* * * * *